US009040050B2

(12) United States Patent
Van De Winkel et al.

(10) Patent No.: US 9,040,050 B2
(45) Date of Patent: May 26, 2015

(54) COMBINATION TREATMENT OF CD38-EXPRESSING TUMORS

(75) Inventors: Jan Van De Winkel, Zeist (NL); Paul Parren, Odijk (NL); Yvo Graus, Odijk (NL); Judith Oprins, Utrecht (NL); Michel De Weers, Houten (NL); Martine Van Vugt, Houten (NL); Ole Baadsgaard, Hellerup (DK); Steen Lisby, Frederiksberg (DK)

(73) Assignee: GENMAB A/S, Copenhagen (DK)

( * ) Notice: Subject to any disclaimer, the term of this patent is extended or adjusted under 35 U.S.C. 154(b) by 730 days.

(21) Appl. No.: 12/442,808

(22) PCT Filed: Sep. 26, 2007

(86) PCT No.: PCT/DK2007/000418
§ 371 (c)(1),
(2), (4) Date: May 11, 2009

(87) PCT Pub. No.: WO2008/037257
PCT Pub. Date: Apr. 3, 2008

(65) Prior Publication Data
US 2010/0092489 A1    Apr. 15, 2010

Related U.S. Application Data

(60) Provisional application No. 60/847,329, filed on Sep. 26, 2006.

(30) Foreign Application Priority Data

Sep. 26, 2006 (DK) .................................. 2006 01232

(51) Int. Cl.
A61K 39/395 (2006.01)
C07K 16/28 (2006.01)
A61K 45/06 (2006.01)
A61K 39/00 (2006.01)

(52) U.S. Cl.
CPC ....... *C07K 16/2896* (2013.01); *A61K 39/39558* (2013.01); *A61K 45/06* (2013.01); *A61K 2039/505* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 5,618,920 A * | 4/1997 | Robinson et al. | 530/387.1 |
| 6,171,586 B1 | 1/2001 | Lam et al. | |
| 6,455,043 B1 * | 9/2002 | Grillo-Lopez | 424/155.1 |
| 7,109,304 B2 * | 9/2006 | Hansen et al. | 530/387.3 |
| 7,829,673 B2 | 11/2010 | De Weers et al. | |
| 2004/0019915 A1 | 1/2004 | Challita-Eid et al. | |
| 2004/0167319 A1 | 8/2004 | Teeling et al. | |
| 2005/0037969 A1 | 2/2005 | Lu et al. | |
| 2005/0266008 A1 | 12/2005 | Graziano et al. | |
| 2006/0019303 A1 | 1/2006 | Castle et al. | |
| 2007/0218060 A1 * | 9/2007 | Long et al. | 424/142.1 |
| 2009/0076249 A1 | 3/2009 | De Weers et al. | |
| 2010/0285004 A1 * | 11/2010 | Tesar et al. | 424/133.1 |

FOREIGN PATENT DOCUMENTS

| | | |
|---|---|---|
| WO | WO-89/08114 A1 | 9/1989 |
| WO | WO-92/01049 A2 | 1/1992 |
| WO | WO-94/17184 A1 | 8/1994 |
| WO | WO-96/16990 A1 | 6/1996 |
| WO | WO-98/16245 A1 | 4/1998 |
| WO | WO-98/16254 A1 | 4/1998 |
| WO | WO-98/50435 A1 | 11/1998 |
| WO | WO-99/62526 A2 | 12/1999 |
| WO | WO-00/06194 A2 | 2/2000 |
| WO | WO-00/40265 A1 | 7/2000 |
| WO | WO-02/06347 A1 | 1/2002 |
| WO | WO-02/32288 A2 | 4/2002 |
| WO | 2004/019915 A1 | 3/2004 |
| WO | 2004/035607 A2 | 4/2004 |
| WO | 2004/045512 A2 | 6/2004 |
| WO | 2004/058288 A1 | 7/2004 |
| WO | WO-2005/042019 A1 | 5/2005 |
| WO | WO-2005/044855 A2 | 5/2005 |
| WO | WO-2005/103083 A2 | 11/2005 |
| WO | WO-2006/088951 A2 | 8/2006 |
| WO | WO-2006/099875 A1 | 9/2006 |
| WO | WO-2006/125640 A2 | 11/2006 |

OTHER PUBLICATIONS

Paul, Fundamental Immunology, 3rd Edition, 1993, pp. 292-295, under the heading Fv Structure and Diversity in Three Dimensions.*
Rudikoff et al Proc. Natl. Acad. Sci. USA, 79(6):1979-1983, Mar. 1982.*
Coleman P. M. Research in Immunology, 145:33-36, 1994.*
MacCallum et al J. Mol. Biol., 262, 732-745, 1996.*
Osterberg et al Blood, 1993, 1428-1434.*
Boccadoro et al, Cancer Cell International, 2005, 5:18.*
Wiesenthal, Human Tumor Assay Journal, on-line at (http://weisenthal.org/synergy1.htm, Mar. 29, 2012.*
Berenbaum, Clin exp Immunol, 1997, 28:1-18.*
Chou, Cancer Res, 2010, 70:440-446.*
Aarhus, Robert et al., "ADP-ribusyl Cyclase and CD38 Catalyze the Synthesis of a Calcium-mobilizing Metabolite from NADP," *The Journal of Biological Chemistry*, vol. 270(51):30327-30333 (1995).
Antonelli, Alessandro et al., "Human Anti-CD38 Autoantibodies Raise Intracellular Calcium and Stimulate Insulin Release in Human Pancreatic Islets," *Diabetes*, vol. 50:985-991 (2001).

(Continued)

*Primary Examiner* — Mark Halvorson
(74) *Attorney, Agent, or Firm* — Nelson Mullins Riley & Scarborough LLP; Jane E. Remillard, Esq.; Christopher L. Frank

(57) ABSTRACT

The invention relates to novel method for the treatment of cancer using a combination therapy comprising an antibody that binds CD38, a corticosteroid and a non-corticosteroid chemotherapeutic agent.

68 Claims, 36 Drawing Sheets

(56) References Cited

OTHER PUBLICATIONS

Ausiello, C.M. et al., "Functional topography of discrete domains of human CD38," *Tissue Antigens*, vol. 56:539-547 (2000).

Bolognesi, A. et al., "CD38 as a target of 1B4 mAb carrying saporin-S6: Design of an immunotoxin for ex vivo depletion of hematological CD38+ neoplasia," *Journal of Biological Regulators and Homeostatic Agents*, vol. 19:145-152 (2005).

Cavo, Michele et al., "Superiority of thalidomide and dexamethasone over vincristine-doxorubicin-dexamethasone (VAD) as primary therapy in preparation for autologous transplantation for multiple myeloma," *Blood*, vol. 106(1):35-39 (2005).

Cotner, Thomas et al., "Human T Cell Proteins Recognized by Rabbit Heteroantisera and Monoclonal Antibodies," *Int. J. Immunopharmac.*, vol. 3(3):255-268 (1981).

Davies, Julian et al., "Affinity improvement of single antibody VH domains: residues in all three hypervariable regions affect antigen binding," *Immunotechnology*, vol. 2:169-179 (1996).

de Weers, M. et al., "Humax-CD38, a New Human CD38 Monoclonal Antibody, Effectively Mediates Killing of Multiple Myeloma and Plasma Cell Leukemia Cells," abstract, submitted for the 16th European Congress of Immunology—ECI2006. Sep. 6-9, 2006—Paris, France.

de Weers, Michel, "HuMax-CD38," Presentation at the Regional Myeloma Group Meeting (2007).

Donovan, K.A. et al., "Binding and internalization of an antibody engineered ant-CD38 single chain variable fragment (scFv) by human myeloma cells," *Blood*, vol. 90(10):88A (1997).

Ellis, Jonathan H. et al., "Engineered Anti-CD38 Monoclonal Antibodies for Immunotherapy of Multiple Myeloma," *The Journal of Immunology*, vol. 155:925-937 (1995).

Funaro, Ada et al., "CD38 Functions Are Regulated Through an Internalization Step," *The Journal of Immunology*, vol. 160:2238-2247 (1998).

Funaro, Ada et al., "Human CD38: a versatile leukocyte molecule with emerging clinical perspectives," *Fundamental and Clinical Immunology*, vol. 3(3):101-113 (1995).

Funaro, Ada et al., "Identification and characterization of an active soluble form of human CD38 in normal and pathological fluids," *International Immunology*, vol. 8(11):1643-1650 (1996).

Funaro, Ada et al., "Involvement of the multilineage CD38 molecule in a unique pathway of cell activation and proliferation," *The Journal of Immunology*, vol. 145(8):2390-2396 (1990).

Genmab, "Humax-CD38 Effective in Preclinical Studies," retrieved online at http://findarticles.com/p/articles/mi_hb5570/is_200512/ai_n24200986 (2005).

Goldmacher, Victor S. et al., "Anti-CD38-Blocked Ricin: An Immunotoxin for the Treatment of Multiple Myeloma," *Blood*, vol. 84(9):3017-3025 (1994).

Hara-Yokoyama, Miki et al., "Alteration of enzymatic properties of cell-surface antigen CD38 by agonistic anti-CD38 antibodies that prolong B cell survival and induce activation," *International Immunopharmacology*, vol. 8:59-70 (2008).

Holt, Lucy J. et al., "Domain antibodies: proteins for therapy," *Trends in Biotechnology*, vol. 21(11):484-490 (2003).

Hoshino, Shin-ichi et al., "Mapping of the Catalytic and Epitopic Sites of Human CD38/NAD+ Glycohydrolase to a Functional Domain in the Carboxyl Terminus," *The Journal of Immunology*, vol. 158:741-747 (1997).

Howard, Maureen et al., "Formation and Hydrolysis of Cyclic ADP-Ribose Catalyzed by Lymphocyte Antigen CD38," *Science*, vol. 262:1056-1059 (1993).

Jackson, David G. et al., "Isolation of a cDNA Encoding the Human CD38 (T10) Molecule, a Cell Surface Glycoprotein with an Unusual Discontinuous Pattern of Expression During Lymphocyte Differentiation," *The Journal of Immunology*, vol. 144(7):2811-2815 (1990).

Johnson, Malisha R. et al., "Primary plasma cell leukemia: morphologic immunophenotypic, and cytogenetic featues of 4 cases treated with chemotherapy and stem cell transplantation," *Annals of Diagnostic Pathology*, vol. 10:263-268 (2006).

Konopleva, Marina et al., "CD38 in Hematopoietic Malignancies," *Human CD38 and Related Molecules.Chem Immunol.*, vol. 75:189-206 (2000).

Konopleva, Marina et al., "Ligation of Cell Surface CD38 Protein with Agonistic Monoclonal Antibody Induces a Cell Growth Signal in Myeloid Leukemia Cells," *The Journal of Immunology*, vol. 161:4702-4708 (1998).

Lande, Roberto et al., "CD38 ligation plays a direct role in the induction of IL-1β, IL-6, and IL-10 secretion in resting human monocytes," *Cellular Immunology*, vol. 220:30-38 (2002).

Malavasi, Fabio et al., "Human CD38: a glycoprotein in search of a function," *Immunology Today*, vol. 15(3):95-97 (1994).

Maloney, David G. et al., "Antibody Therapy for Treatment of Multiple Myeloma," *Seminars in Hematology*, vol. 36(1 Suppl. 3):30-33 (1999).

Mills, Charity et al., "Characterization of Monoclonal Antibodies that Inhibit CD38 ADP-Ribosyl Cyclase Activity," Poster with abstract presented at a student conference at the University of Minnesota (2007).

Parren, "HuMax-CD38," Conference Proceedings, Presentation for the CD38 metting in Torino (2006).

Parren, "HuMax-CD38," Conference Proceeding, Presentation for the 23rd International Conference on Advances in the Application of Monoclonal Antibodies in Clinical Oncology, Myconos, Greece (2006).

Parren, P.W.H.I. et al., "HuMax-CD38, a new human CD38 monoclonal antibody, effectively mediates killing of multiple myeloma and plasma cell leukemia cells," PWHI Conference Proceeding, Presentation for the CD38 meeting in Torino, Jun. 8-10, 2006.

Peipp, Matthias et al., AN PREV200600185745, "Fully human CD38 antibodies efficiently trigger ADCC of multiple myeloma cell lines and primary tumor cells," *Blood*, vol. 106(11):944A, 47th Annual Meeting of the American-Society-of-Hematology (2005).

Peipp, M. et al., "Fully Human CD38 Antibodies Efficiently Trigger ADCC and CDC of Multiple Myeloma and Plasma Cell Leukemia Cells," Conference Proceedings, Poster Presentation at the 2005 Annual Meeting of the American Society of Hematology, Dec. 12, 2005.

Peng, Kah-Whye et al., "Oncolytic measles viruses displaying a single-chain antibody against CD38, a myeloma cell marker," *Blood*, vol. 101(7):2557-2562 (2003).

Stevenson, George T., "CD38 as a Therapeutic Target," *Mol. Med.*, vol. 12(11-12):345-346 (2006).

Stevenson, Freda K. et al., "Preliminary Studies for an Immunotherapeutic Approach to the Treatment of Human Myeloma Using Chimeric Anti-CD38 Antibody," *Blood*, vol. 77(5):1071-1079 (1991).

Takasawa, Shin et al., "Synthesis and Hydrolysis of Cyclic ADP-Ribose by Human Leukocyte Antigen CD38 and Inhibition of the Hydrolysis by ATP," *The Journal of Biological Chemistry*, vol. 268(35):26052-26054 (1993).

Vooijs, W.C. et al., "Evaluation of CD38 as Target for Immunotherapy in Multiple Myeloma," *Blood*, vol. 85(8):2282-2284 (1995).

Wu, Herren et al., "Humanization of a Murine Monoclonal Antibody by Simultaneous Optimization of Framework and CDR Residues," *J. Mol. Biol.*, vol. 294:151-162 (1999).

Yamashita, Y. et al., "A monoclonal antibody against a murine CD38 homologue delivers a signal to B cells for prolongation of survival and protection against apoptosis in vitro: unresponsiveness of X-linked immunodeficient B cells," *Immunology*, vol. 85:248-255 (1995).

Zocchi, Elena et al., "A Single Protein Immunologically Identified as CD38 Displays NAD+ Glycohydrolase, ADP- Ribosyl Cyclase and Cyclic ADP-Ribose Hydrolase Activities at the Outer Surface of Human Erythrocytes," *Biochemical and Biophysical Research Communications*, vol. 196(3):1459-1465 (1993).

Zubiaur, Mercedes et al., "CD38 Ligation Results in Activation of the Raf-1/Mitogen-Activated Protein Kinase and the CD3-ζ/ζ-Associated Protein-70 Signaling Pathways in Jurkat T Lymphocytes," *The Journal of Immunology*, vol. 159:193-205 (1997).

(56) References Cited

OTHER PUBLICATIONS

International Search Report for Application No. PCT/DK2006/000166, dated Aug. 14, 2006.
Burgess, Wilson H. et al., "Possible Dissociation of the Heparin-binidng and Mitogenic Activities of Heparin-binding (Acidic Fibroblast Growth Factor-1 from Its Receptor-binding Activities by Site-directed Mutagenesis of a Single Lysine Residue," The Journal of Cell Biology, vol. 111:2129-2138 (1990).
Casset, Florence et al., "A peptide mimetic of an anti-CD4 monoclonal antibody by rational design," Biochemical and Biophysical Research Communications, vol. 307:198-205 (2003).
Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).
Holm, Patrik et al., "Functional mapping and single chain construction of the anti-cytokeratin 8 monoclonal antibody TS1," Molecular Immunology, vol. 44:1075-1084 (2007).
Lazar, Eliane et al., "Transforming Growth Factor a: Mutation of Aspartic Acid 47 and Leucine 48 Results in Different Biological Activities," Molecular and Cellular Biology, vol. 8(3):1247-1252 (1988).
Lin, Michael C. et al., "Structure-Function Relationships in Glucagon: Properties of Highly Purified Des-His-, Monoiodo-, and [Des-Asn28, Thr29](homoserine lactone27)-glucagon," Biochemistry, vol. 14(8):1559-1563 (1975).
Schwartz, Gerald P., "A superactive insulin: [B10-Aspartic acid]insulin(human)," Proc. Natl. Acad. Sci. USA, vol. 84:6408-6411 (1987).
Skolnick, Jeffrey et al., "From genes to protein structure and function: novel applications of computational approaches in the genomic era," TIBTECH, vol. 18:34-39 (2000).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Written Opinion for Application No. PCT/DK2006/000166, dated Sep. 25, 2007.
Shimazaki, Chihiro, "Advances in the Treatment of Multiple Myeloma—standard early-stage treatment," Medical Practice, vol. 22(8):1395-1398 (2005).
Terada, Hideo, "What is multiple myeloma?" Modern Physician, vol. 26(5):883-887 (2006).
Green, L.L. et al., "Antigen-specific human monoclonal antibodies from mice engineered with human Ig heavy and light chain YACs," Nature Genetics, vol. 7:13-21 (1994).
Lonberg, Nils et al., "Antigen-specific human antibodies from mice comprising four distinct genetic modifications," Nature, vol. 368:856-859 (1994).
Mukherjee, Jean et al., "Production and Characterization of Protective Human Antibodies against Shiga Toxin 1," Infection and Immunity, vol. 70(10):5896-5899 (2002).

Peipp, Matthias et al., "Fully Human CD38 Antibodies Efficiently Trigger ADCC and CDC of Multiple Myeloma Cell Lines and Primary Tumor Cells," Conference Proceedings, Poster presentation of the 2005 Annual Meeting of the American Society of Hematology, 1 page (2005).
Ferrero, Enza et al., "Characterization and phylogenetic epitope mapping of CD38 ADPR cyclase in the cynomolgus macaque," BMC Immunology, vol. 5(21):1-13 doi10.1186/1471-2172-5-21 (2004).
Boccadoro, Mario et al., "Preclinical evaluation of the proteasome inhibitor bortezomib in cancer therapy," Cancer Cell International, vol. 5(18):1-9 doi:10.1186/1475-2867-5-18 (2005).
Field-Smith, Antonia et al., "Bortezomib (Velcade) in the treatment of multiple myeloma," Therapeutics and Clinical Risk Management, vol. 2(3):271-279 (2006).
Jagannath, Sundar, "Multiple Myeloma Update from the American Society of Clinical Oncology (ASCO) 41st Annual Meeting," Update from the American Society of Clinical Oncology (ASCO) 41st Annual Meeting: Poster Sessions, 3 pages (May 20, 2005).
Kropff, Martin H. et al., "Bortezomib in combination with dexamethasone for relapsed multiple myeloma," Leukemia Research, vol. 29:587-590 (2005).
De Weers, M. et al., "HuMax-CD38, a new human CD38 monoclonal antibody, effectively mediates killing of multiple myeloma and plasma cell leukemia cells," Poster presented at the 1st Joint Meeting of European National Societies of Immunology under auspices of EFIS, Sep. 6-9, 2006.
Abebanjo, Olugbenga A. et al., "A new function for CD38/ADP-ribosyl cyclase in nuclear ca2+ homeostasis," Nature Cell Biology, vol. 1:409-414 (1999).
Franco, Luisa et al., "The transmembrane glycoprotein CD38 is a catalytically active transporter responsible for generation and influx of the second messenger cyclic ADP-ribose across membranes," FASEB J., vol. 12:1507-1520 (1998).
Ikehata, Fumiko et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," J. Clin. Invest., vol. 102(2):395-401 (1998).
Graeff, Richard M. et al., "Enzymatic Synthesis and Characterizations of Cyclic GDP-ribose. A Procedure for Distinguishing Enzymes with ADP-Ribosyl Cyclase Activity," The Journal of Biological Chemistry, vol. 269 (48):30260-30267 (1994).
Adams, Julian et al., "Proteasome inhibition: a new strategy in cancer treatment," Investigational New Drugs, vol. 18:109-121 (2000).
Orlowski, Robert Z., "The Ubiquitin Proteasome Pathway from Bench to Bedside," American Society of Hematology, pp. 220-225 (2005).
Carter, Paul J., "Potent Antibody Therapeutics by Design," Nature Reviews Immunology, Vo. 6:343-357(2006).
Shubinsky, George et al., "The CD38 Lymphocyte Differentiation Marker: New Insight Into Its Ectoenzymatic Activity and Its Role as a Signal Transducer," Immunity, vol. 7:315-324(1997).

* cited by examiner

FIGURE 1
A:
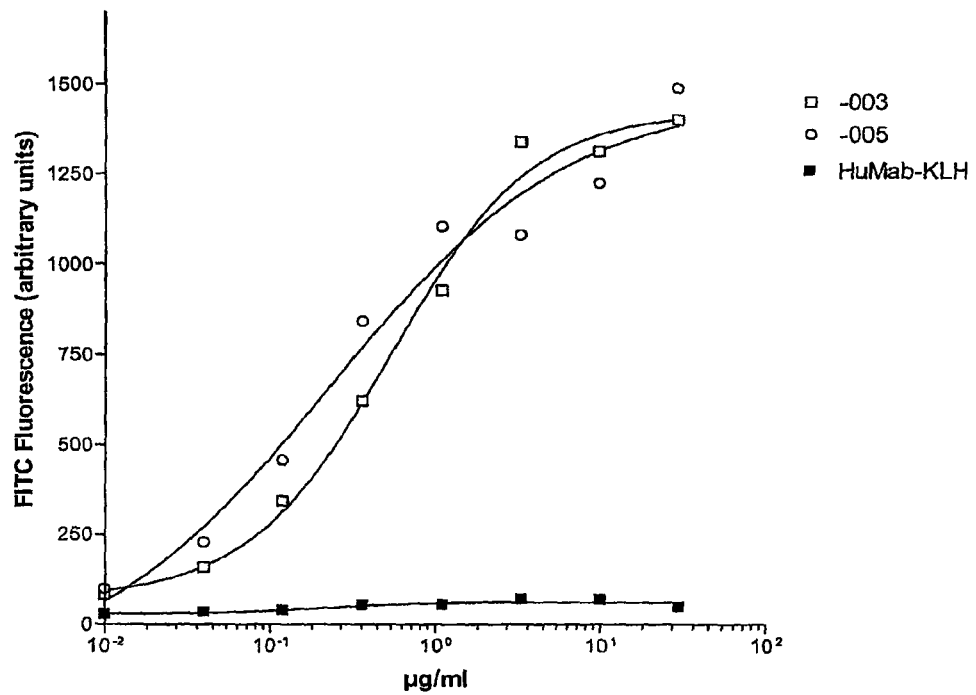
B:
Binding of -024 on CHO-CD38 cells.
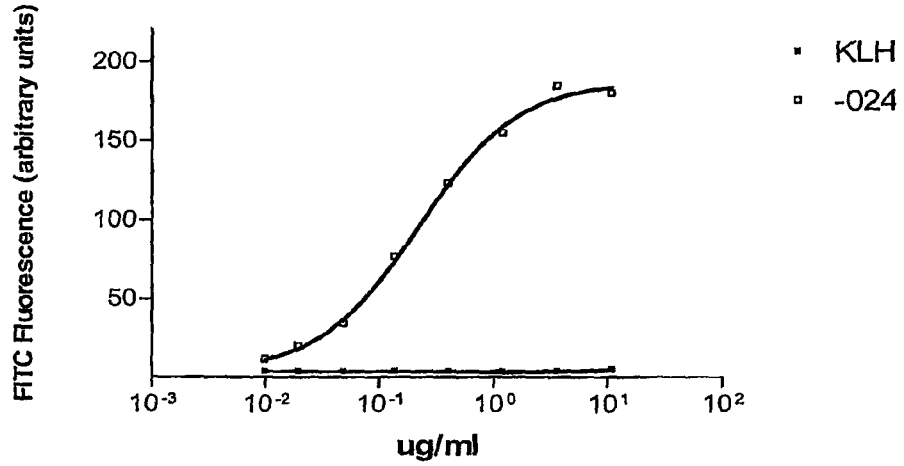

FIGURE 2
A:
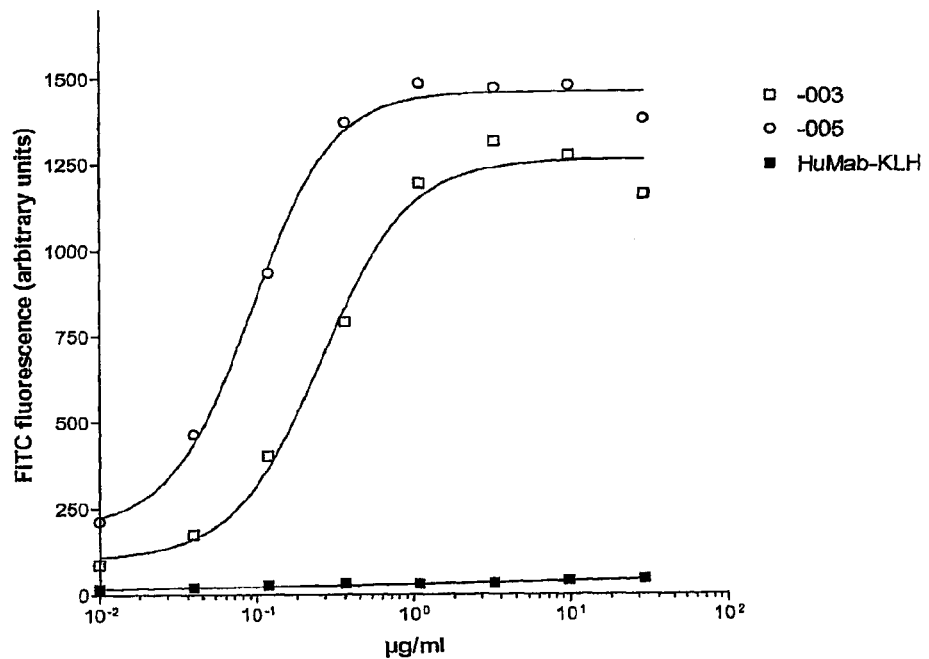
B:
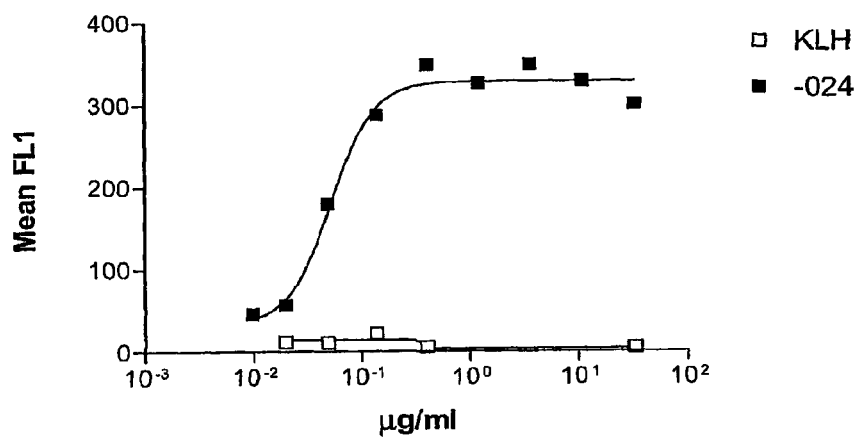

FIGURE 4
A:
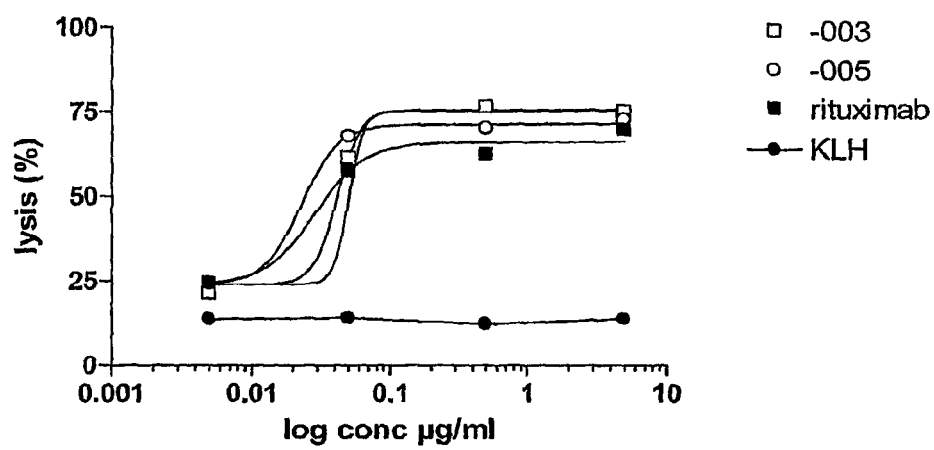
B:
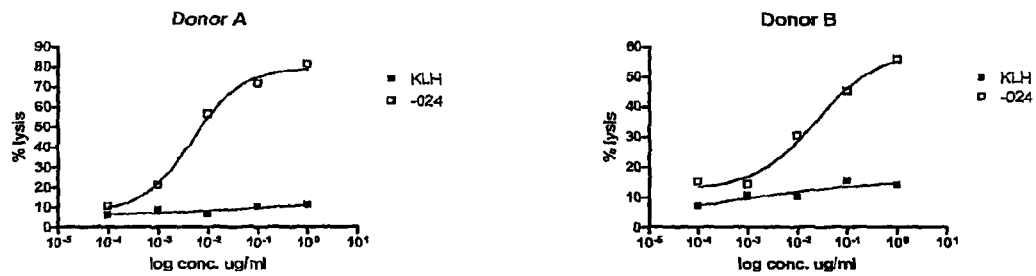

FIGURE 5
A:
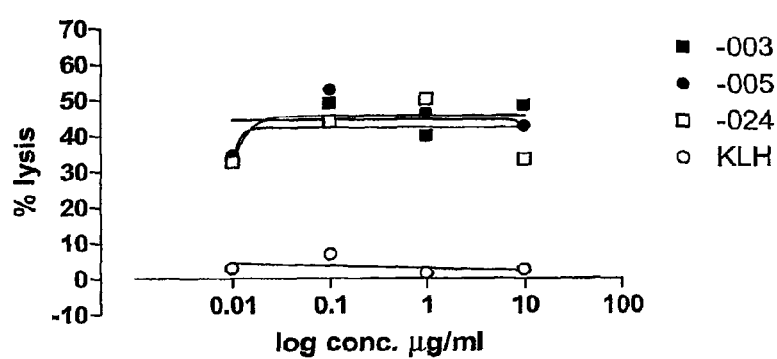
B:
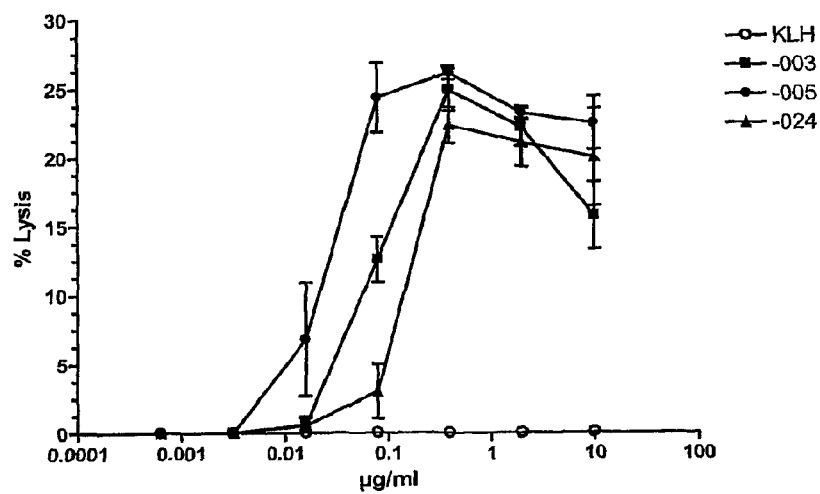

FIGURE 9
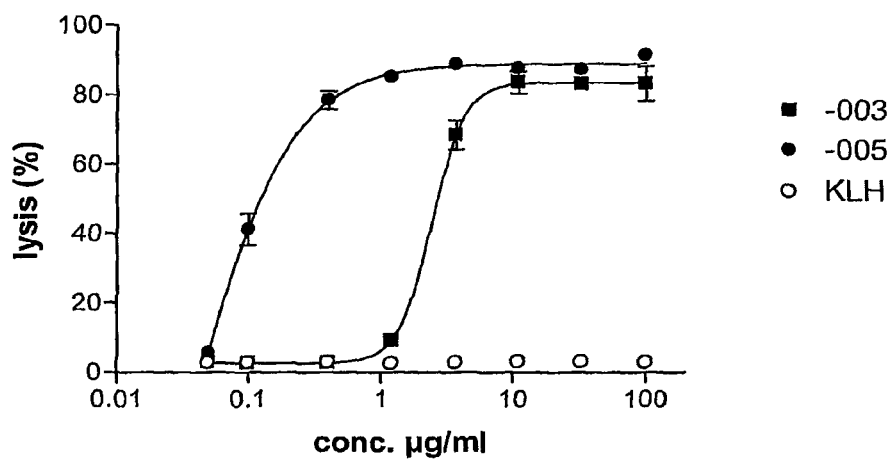
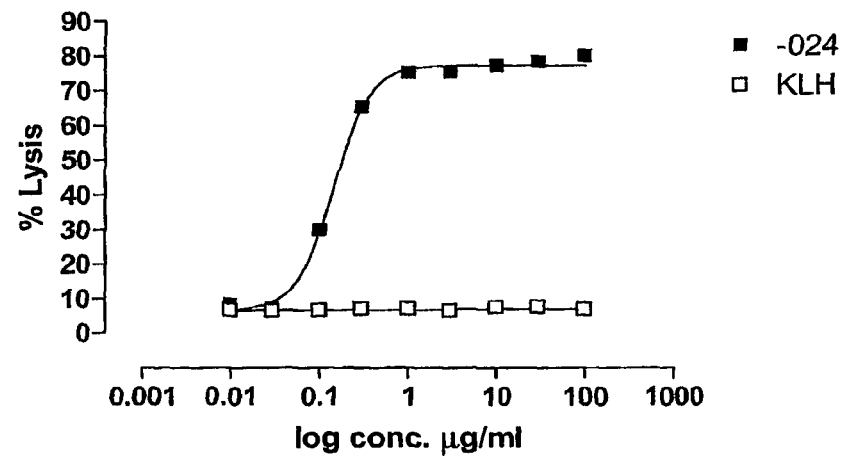

FIGURE 10 (1/3)
A:
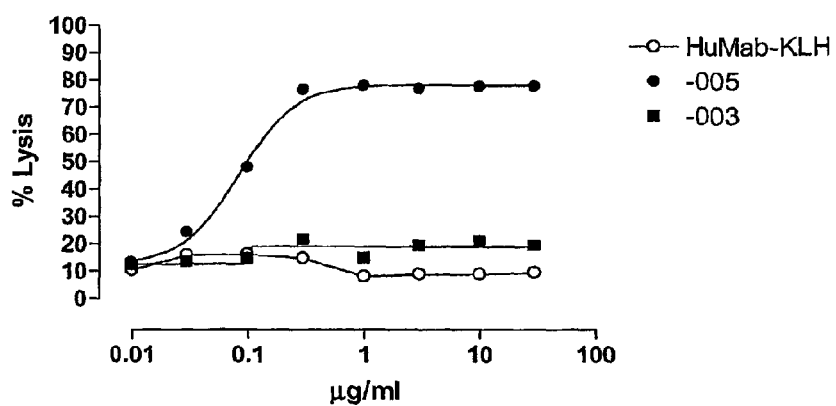
B:
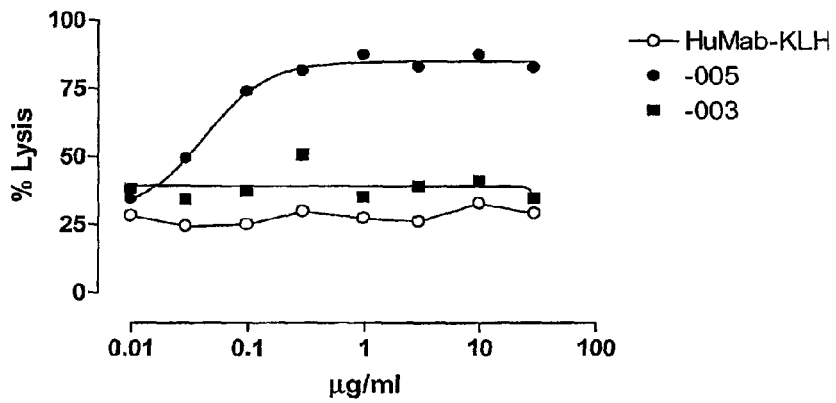

FIGURE 10 (2/3)
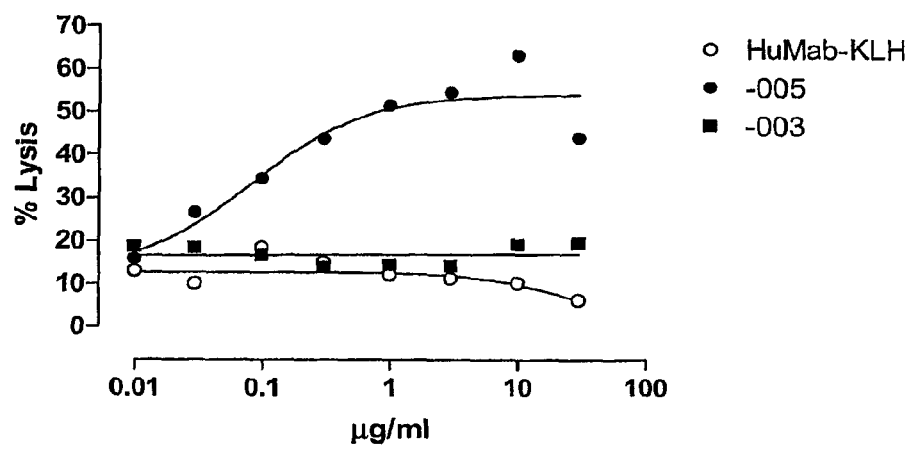
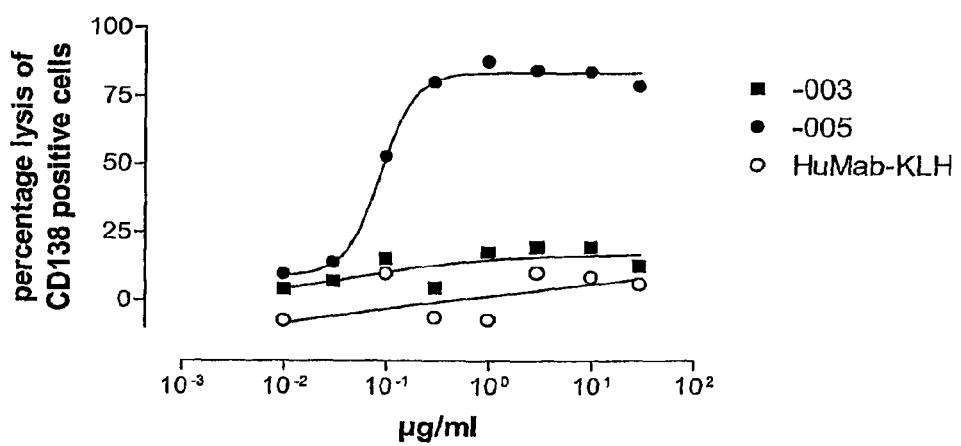

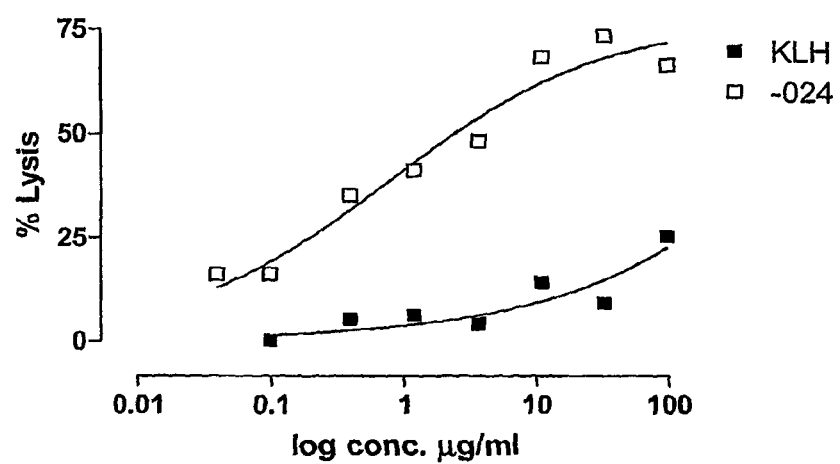
FIGURE 10 (3/3)

FIGURE 12
FIGURE 12A
FIGURE 12B
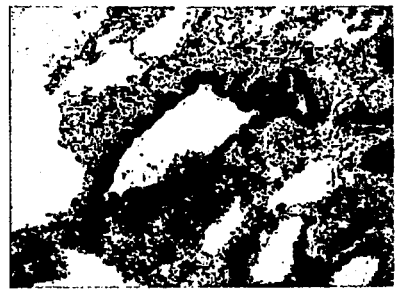
FIGURE 12C
FIGURE 12D

FIGURE 13
FIGURE 13A
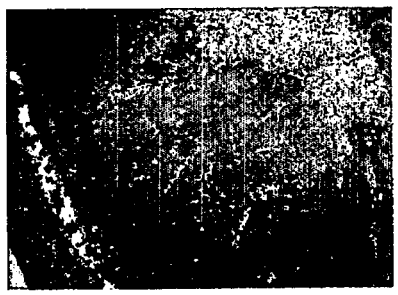
FIGURE 13B
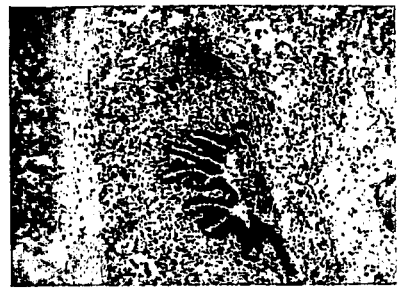
FIGURE 13C
FIGURE 13D

FIGURE 14
14A
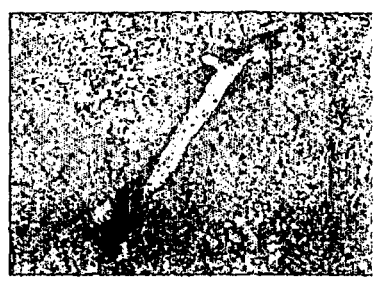
14B
14C
14D
14E
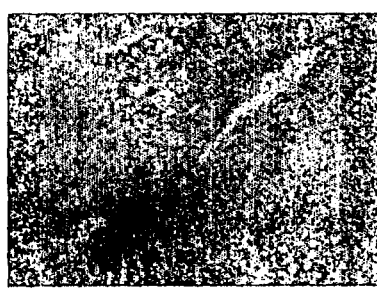

FIGURE 16
FIGURE 16A
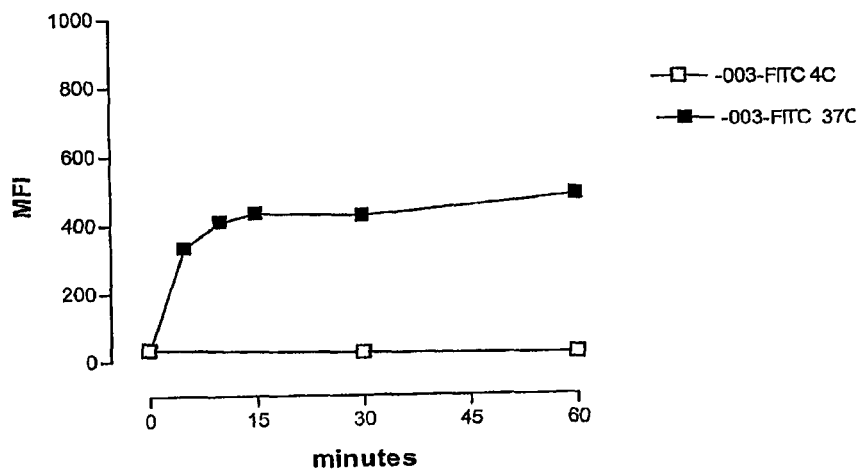
FIGURE 16B
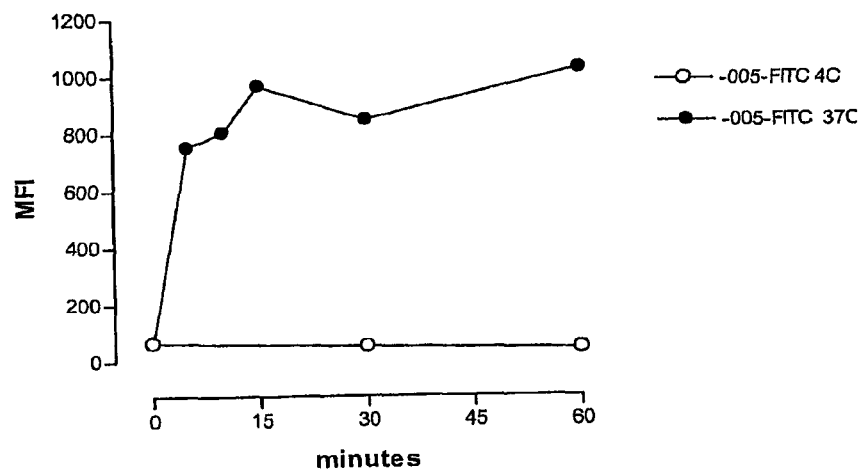

FIGURE 21
A
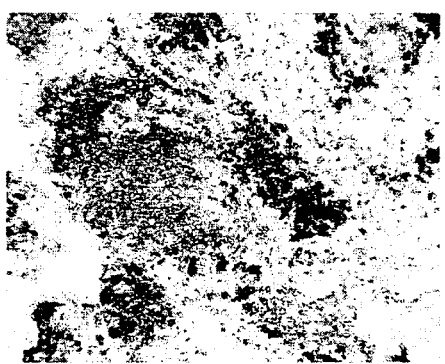
B
C
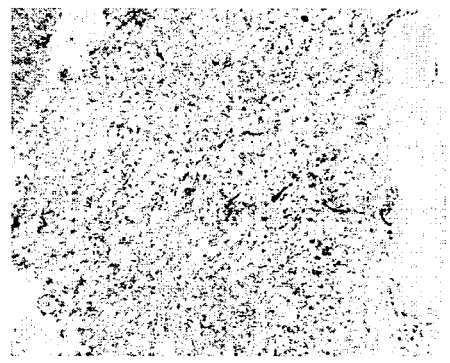

FIGURE 22
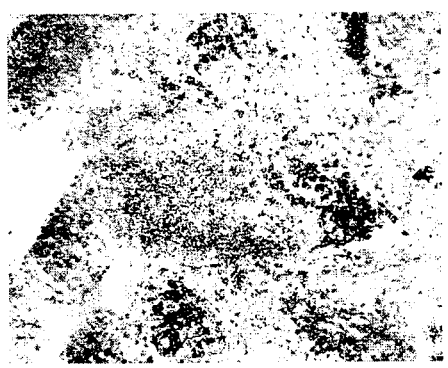

FIGURE 23 (1/3)
A:
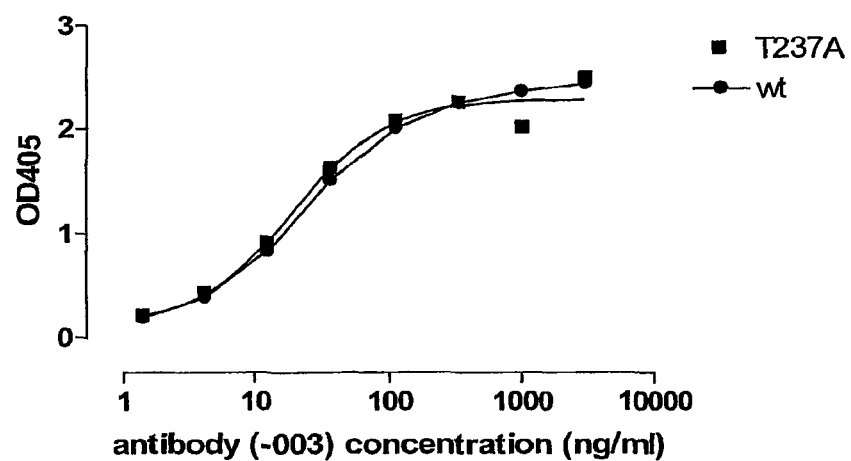
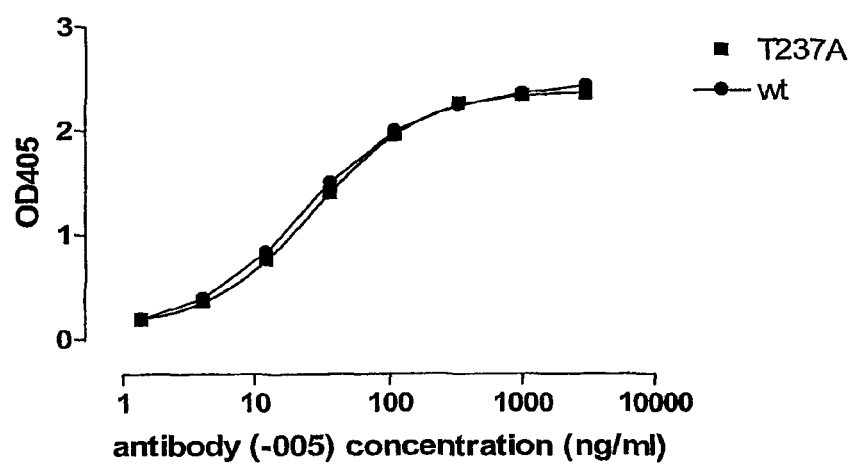

FIGURE 23 (2/3)
B:
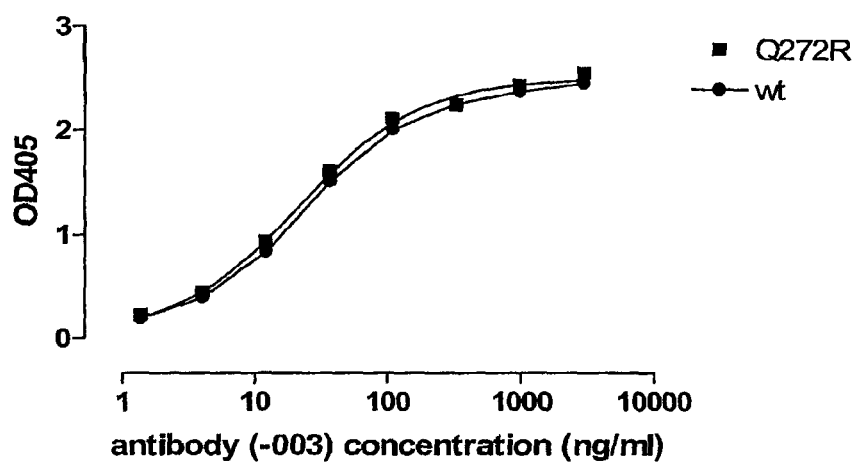
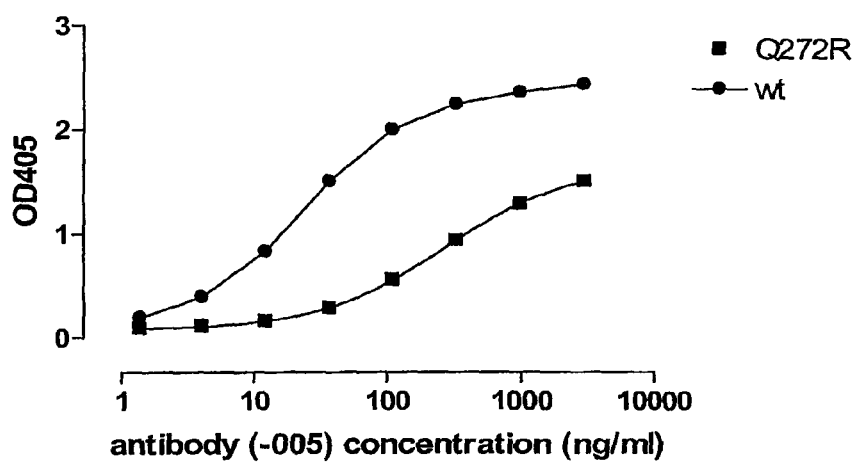

FIGURE 23 (3/3)
C:
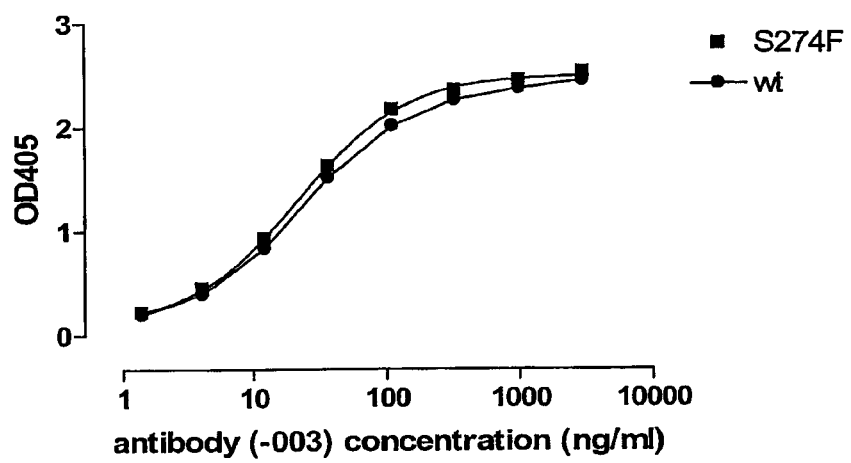
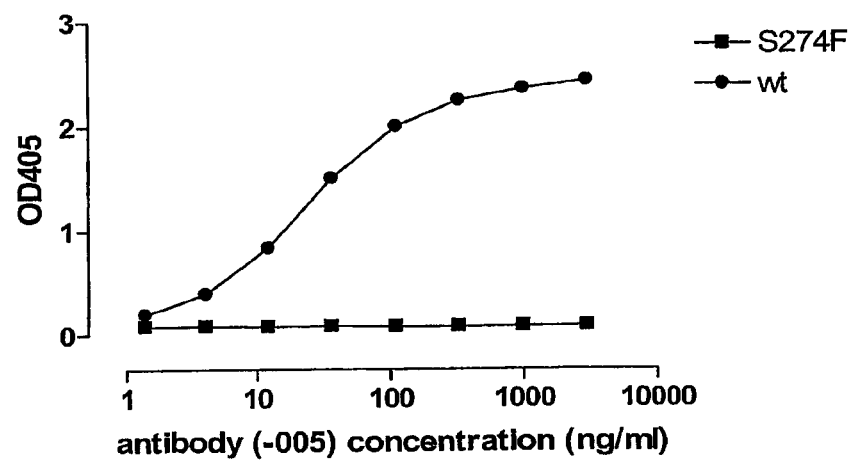

FIGURE 24
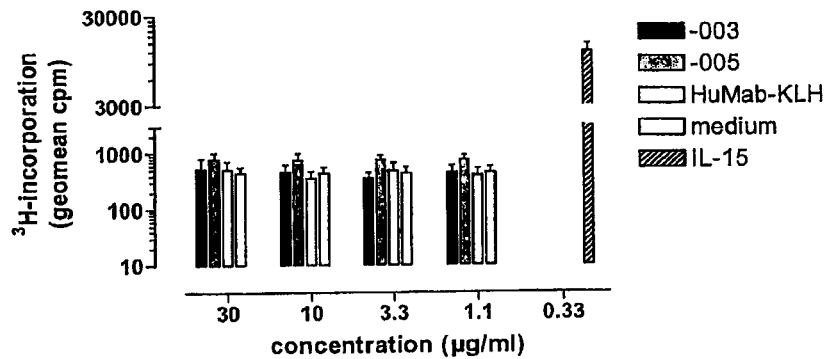
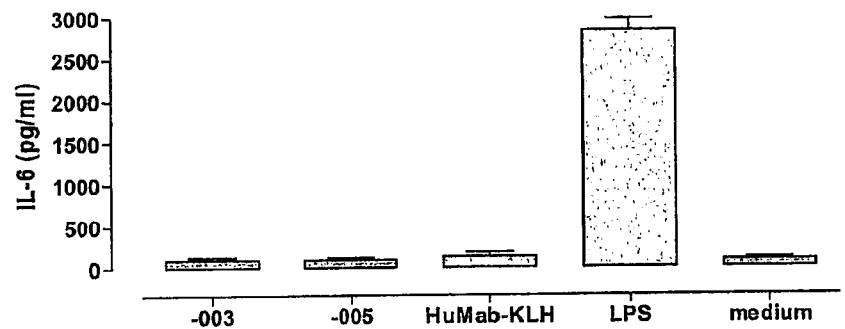

FIGURE 25 (1/2)
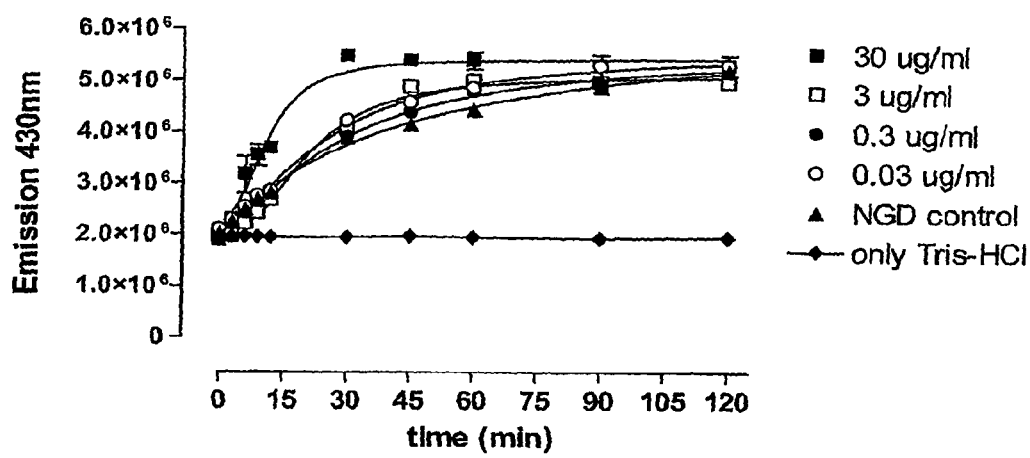
A
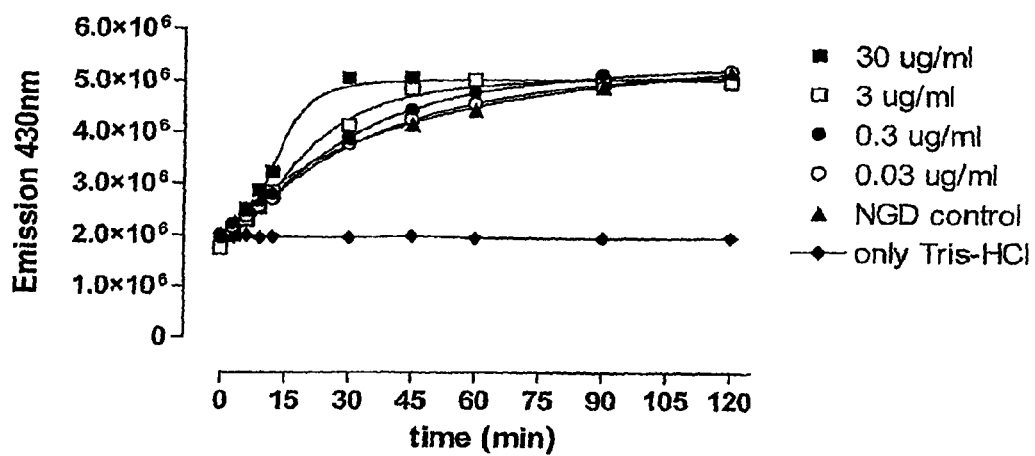
B

FIGURE 25 (2/2)
C
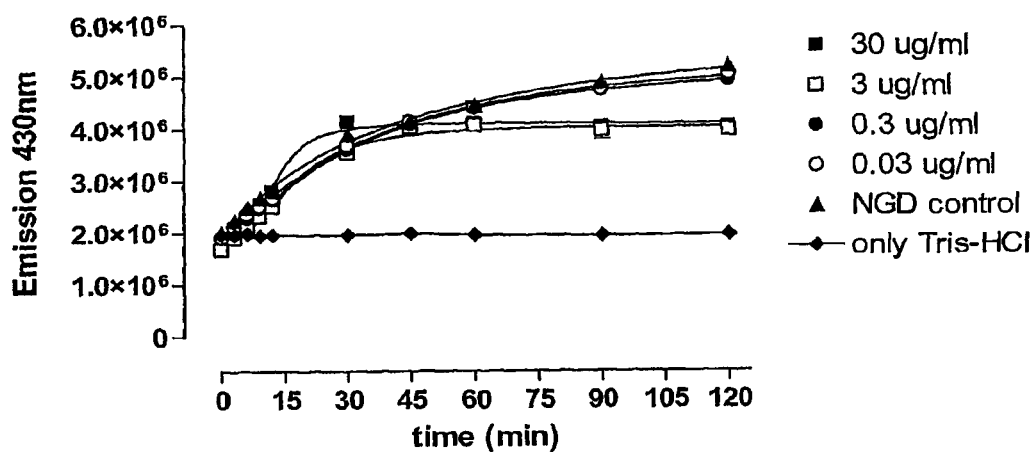
D
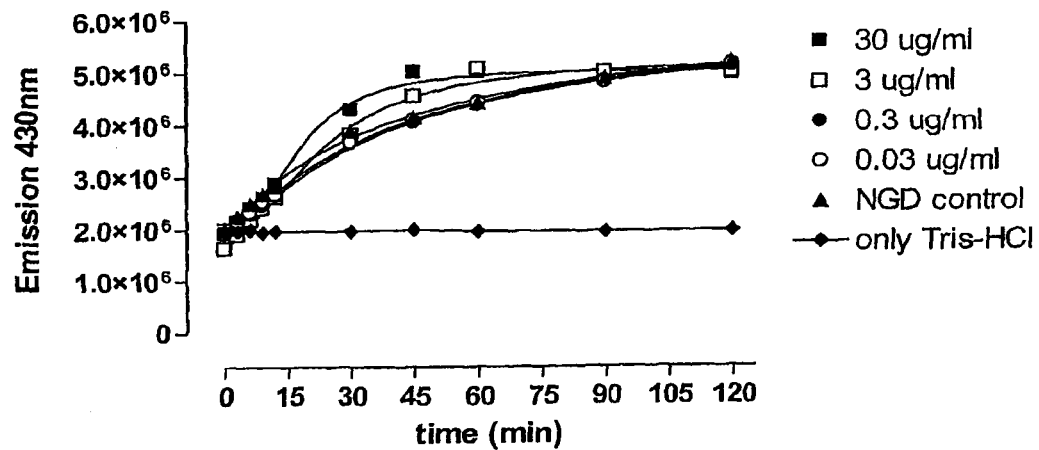

FIGURE 26 (1/2)
A
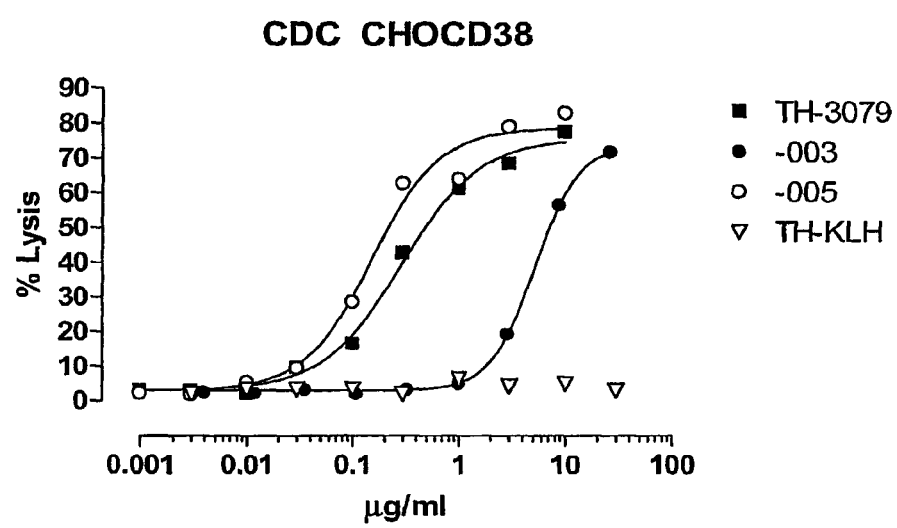
B
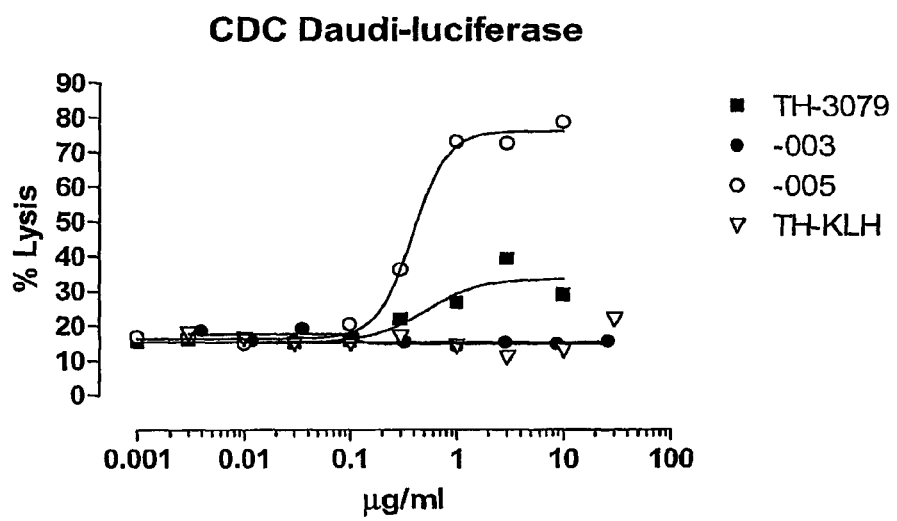

FIGURE 26 (2/2)
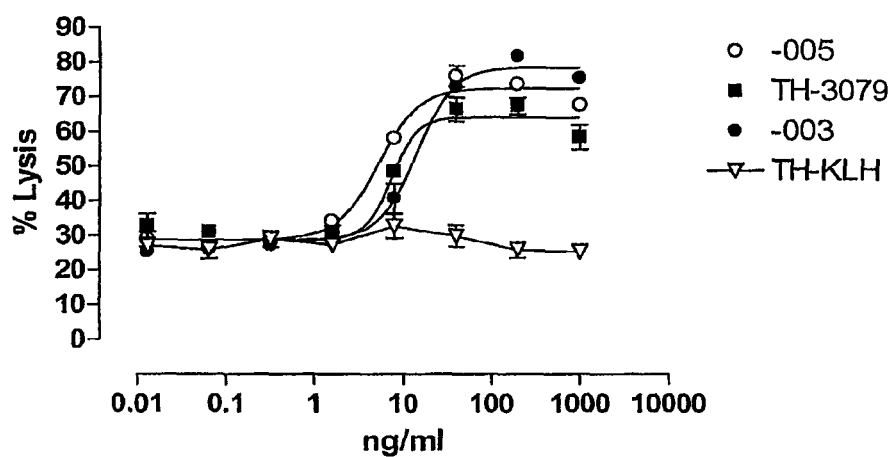

COMBINATION TREATMENT OF CD38-EXPRESSING TUMORS

FIELD OF THE INVENTION

The present invention relates to the treatment of cancer using a combination therapy comprising an antibody that binds CD38, a corticosteroid and a non-corticosteroid chemotherapeutic agent.

BACKGROUND

Multiple myeloma is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system.

Approximately 1% of all cancers, and slightly more than 10% of all hematologic malignancies, can be attributed to multiple myeloma (MM). Incidence of MM increases in the aging population, with the median age at time of diagnosis being about 61 years.

Currently available therapies for multiple myeloma include chemotherapy, stem cell transplantation, Thalomid® (thalidomide), Velcade® (bortezomib), Aredia® (pamidronate), and Zometa® (zoledronic acid). Current treatment protocols, which include a combination of chemotherapeutic agents such as vincristine, BCNU, melphalan, cyclophosphamide, adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Yet overall survival has only been slightly prolonged, and no evidence for a cure has been obtained. Ultimately, all MM patients relapse, even under maintenance therapy with interferon-alpha (IFN-α) alone or in combination with steroids.

If a patient is candidate or possible candidate for autologous transplant, induction therapy often involve non-alkylating chemotherapy, in that alkylating agents interfere with harvesting (stem cell collection). The preferred regimen is VAD, which allows for subsequent harvest (Wu K L, Clin Lymphoma Myeloma 2005; 6:96). Another treatment modality, tested in induction setting before transplant, includes Thalidomide combined with dexamethasone (Cavo M Blood 2005; 106:35).

Efficacy of the available chemotherapeutic treatment regimens for MM is limited by the low cell proliferation rate and development of multi-drug resistance. For more than 90% of MM patients, the disease becomes chemoresistant. As a result, alternative treatment regimens aimed at adoptive immunotherapy targeting surface antigens on plasma cells are being sought.

CD38 is an example of an antigen expressed on such malignant plasma cells, and is expressed in a variety of malignant hematological diseases, including but not restricted to, multiple myeloma, B-cell chronic lymphocytic leukemia, B-cell acute lymphocytic leukemia, Waldenström macroglobulinemia, primary systemic amyloidosis, mantle-cell lymphoma, pro-lymphocytic/myelocytic leukemia, acute myeloid leukemia, chronic myeloid leukemia, follicular lymphoma, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Diseases where CD38 expression could be involved, include but are not restricted to broncho-epithelial carcinomas of the lung, breast cancer (evolving from malignant proliferation of epithelial lining in ducts and lobules of the breast), pancreatic tumors, evolving from the b-cells (insulinomas), tumors evolving from epithelium in the gut (e.g. adenocarcinoma and squamous cell carcinoma) In CNS, neuroblastomas express CD38. Other such diseases include carcinoma in the prostate gland, seminomas in testis and ovarian cancers.

Normally, CD38 is expressed by hemopoietic cells, and in solid tissues. With regard to hemopoietic cells, the majority of medullary thymocytes are $CD38^+$, resting and circulating T- and B-cells are $CD38^-$, and activated cells are $CD38^+$. CD38 is also expressed on approximately 80% of resting NK cells and monocytes, and on lymph node germinal center lymphoblasts, plasma B cells and some intrafollicular cells. CD38 can also be expressed by dendritic cells. A significant proportion of normal bone marrow cells, particular precursor cells, express CD38. In addition to lymphoid precursor cells, CD38 is also expressed on erythrocytes and on platelets.

With regard to solid tissues, CD38 is expressed in the gut by intra-epithelial cells and lamina propria lymphocytes, by Purkinje cells and neurofibrillary tangles in the brain, by epithelial cells in the prostate, β-cells in the pancreas, osteoclasts in the bone, retinal cells in the eye, and sarcolemma of smooth and striated muscle.

Functions ascribed to CD38 include both receptor mediation in adhesion and signaling events and (ecto-) enzymatic activity. As an ectoenzyme, CD38 uses $NAD^+$ as substrate for the formation of cyclic ADP-ribose (cADPR) and ADPR, but also of nicotinamide and nicotinic acid-adenine dinucleotide phosphate (NAADP). cADPR and NAADP have been shown to act as second messengers for $Ca^{2+}$ mobilization. By converting NAD+ to cADPR, CD38 regulates the extracellular NAD+ concentration and hence cell survival by modulation of NAD-induced cell death (NCID). In addition to signaling via $Ca^{2+}$, CD38 signaling occurs via cross-talk with antigen-receptor complexes on T and B cells or other types of receptor complexes, e.g. MHC molecules, and is in this way involved in several cellular responses, but also in switching and secretion of IgG1.

Anti-CD38 antibodies are described in the literature, for instance in Lande R, et al., Cell Immunol. 220(1), 30-8 (2002), Ausiello C M, et al., Tissue Antigens. 56(6), 539-47 (2000), and Cotner T, et al., Int J Immunopharmacol. 3(3), 255-68 (1981) and in WO2005/103083 (Morphosys). CD38 has a number of functions, which may or may not be activated by a molecule binding to CD38. For instance the mouse anti-CD38 antibody IB4 has agonistic properties in relation to CD38. IB4 is shown to induce T cell activation as indicated by $Ca^{2+}$ mobilization in Jurkat cells (Zubiaur M, et al., J Immunol. 159(1), 193-205 (1997), to induce significant proliferation of peripheral blood mononuclear cells (PBMCs), to induce release of significant IL-6 levels and to induce release of detectable IFN-γ levels (Lande, Zubiaur Morra, Ansiello supra).

It is clear that in spite of the recent progress in the discovery and development of anti-cancer agents, many forms of cancer involving CD38-expressing tumors still have a poor prognosis. Thus, there is a need for improved methods for treating such forms of cancer.

SUMMARY OF THE INVENTION

It is an object of the invention to provide improved methods for the treatment of CD38-expressing tumors that result in increased efficacy and/or prolonged survival.

Thus, in a first main aspect, the invention relates to a method for inhibiting growth and/or proliferation of tumor cells expressing CD38 in an individual in need thereof, which method comprises administration to the said individual of i) a non-agonistic antibody which binds to CD38,
ii) at least one corticosteroid, and
iii) at least one non-corticosteroid chemotherapeutic agent.

The three types of medicaments may be administered simultaneously or sequentially in any order. Furthermore, they may be administered separately or in one or two pharmaceutical compositions.

The triple therapy may, in some embodiments, allow administration of lower amounts of a medicament than when used as mono- or in duplex therapy. Such lower amounts may generate fewer side-effects, allowing more effective treatment of patients that cannot be treated with high doses, such as elderly or hypersensitive patients.

In one embodiment, the non-agonistic antibody which binds to CD38 used in the invention is antibody -005, -003 or -024, described herein. These antibodies have previously been described in patent application PCT/DK2006/000166 (WO 2006099875) (Genmab).

In some embodiments, said at least one non-corticosteroid chemotherapeutic agent comprises an alkylating agent, such as melphalan, and/or
a glutamic acid derivative, such as thalidomide or lenalidomide and/or
a proteasome inhibitor, such as bortezomib.

In a similar aspect, the invention relates to a method of treating cancer involving cells expressing CD38 in an individual, wherein said method comprises the features of the method described above.

In a further aspect, the invention relates to a method for treating cancer involving tumor cells expressing CD38 in an individual in need thereof, which method comprises administration to the said individual of:

i) a non-agonistic antibody which binds to CD38,
ii) optionally at least one corticosteroid, and
iii) optionally at least one non-corticosteroid chemotherapeutic agent, followed by autologous peripheral stem cell or bone marrow transplantation.

Thus, in this method, the anti-CD38 antibody is used in induction therapy preceding autologous peripheral stem cell or bone marrow transplantation. Without being bound by any specific theory, it is believed that anti-CD38 antibodies are particularly suitable for such induction therapy, because they do not have many undesired side-effects, thus keeping the patient in good condition before the transplant.

In an even further aspect, the invention relates to a therapeutic combination for inhibiting growth and/or proliferation of tumor cells expressing CD38, comprising i) a non-agonistic antibody which binds to CD38,
ii) at least one corticosteroid, and
iii) at least one non-corticosteroid chemotherapeutic agent, wherein the combination is suitable for separate, sequential and/or simultaneous administration.

BRIEF DESCRIPTION OF THE FIGURES

FIG. 1A shows the binding of -003, -005 and the isotype control antibody HuMab-KLH to CD38-transfected CHO (CHO-CD38) cells as measured by flow cytometry. The experimental setup is described in Example 4.

FIG. 1B shows the binding of -024 and HuMab-KLH to CD38-transfected CHO (CHO-CD38) cells as measured by flow cytometry. The experimental setup is described in Example 4.

FIG. 2A shows the binding of -003, -005 and HuMab-KLH to Daudi cells as measured by flow cytometry. The experimental setup is described in Example 4.

FIG. 2B shows the binding of -024 and HuMab-KLH to Daudi cells as measured by flow cytometry. The experimental setup is described in Example 4.

FIG. 4A shows the ability of -003 and -005 to induce lysis of Daudi cells by ADCC as compared to rituximab and HuMab-KLH. The experimental setup is described in Example 5.

FIG. 4B shows the ability of -024 to induce lysis of Daudi cells by ADCC as compared to HuMab-KLH. The experimental setup is described in Example 5.

FIG. 5A shows the ability of -003, -005 and -024 to induce lysis of fresh multiple myeloma tumor cells by ADCC as compared to HuMab-KLH. The experimental setup is described in Example 5.

FIG. 5B shows the ability of -003, -005 and -024 to induce lysis of fresh plasma cell leukemia tumor cells by ADCC as compared to HuMab-KLH. The experimental setup is described in Example 5.

FIG. 9A shows the CDC-mediated lysis of CHO-CD38 cells induced by -003 and -005 compared to HuMab-KLH. The experimental setup is described in Example 6.

FIG. 9B shows the CDC-mediated lysis of CHO-CD38 cells induced by -024 compared with HuMab-KLH. The experimental setup is described in Example 6.

FIG. 10A shows the CDC-mediated lysis of 3% refractory tumor cells in the presence of -003, -005 and HuMab-KLH. The experimental setup is described in Example 6.

FIG. 10B shows the CDC-mediated lysis of 9% refractory tumor cells in the presence of -003, -005 and HuMab-KLH. The experimental setup is described in Example 6.

FIG. 10C shows the CDC-mediated lysis of 30-40% tumor cells in the presence of -003, -005 and HuMab-KLH. The experimental setup is described in Example 6.

FIG. 10D shows the CDC-mediated lysis of 70% tumor cells in the presence of -003, -005 and HuMab-KLH. The experimental setup is described in Example 6.

FIG. 10E shows the CDC-mediated lysis of multiple myeloma cells in the presence of -024 and HuMab-KLH. The experimental setup is described in Example 6.

FIG. 12A shows the immunohistological staining of macrophages, lymphocytes and plasma B cells with -003. The experimental setup is described in Example 10.

FIG. 12B shows the immunohistological staining of bronchial epithelium with -003. The experimental setup is described in Example 10.

FIG. 12C shows the immunohistological staining of myocytes with -003. The experimental setup is described in Example 10.

FIG. 12D shows the immunohistological staining of cynomolgus lymphoid tissue with -003. The experimental setup is described in Example 10.

FIG. 13A shows the immunohistological staining of macrophages, lymphocytes and plasma B cells with -005. The experimental setup is described in Example 10.

FIG. 13B shows the immunohistological staining of bronchial epithelium with -005. The experimental setup is described in Example 10.

FIG. 13C shows the immunohistological staining of myocytes with -005. The experimental setup is described in Example 10.

FIG. 13D shows the immunohistological staining of cynomolgus lymphoid tissue with -005. The experimental setup is described in Example 10.

FIG. 14A shows immunohistological staining of liver endothelium with CD31. The experimental setup is described in Example 10.

FIG. 14B shows immunohistological staining of liver endothelium with vWF. The experimental setup is described in Example 10.

FIG. 14C shows immunohistological staining of liver endothelium with anti-KLH. The experimental setup is described in Example 10.

FIG. 14D shows immunohistological staining of liver endothelium with -003. The experimental setup is described in Example 10.

FIG. 14E shows immunohistological staining of liver endothelium with -005. The experimental setup is described in Example 10.

FIG. 16A shows the internalization of -003 as measured by EtBr-quenching. The experimental setup is described in Example 12.

FIG. 16B shows the internalization of -005 as measured by EtBr-quenching. The experimental setup is described in Example 12.

FIG. 21 shows CD38 staining of B cells in xenografts before implantation (A), or after treatment with anti-KLH (B), or -005 (C). Methods are described in Example 15.

FIG. 22 shows CD138 staining of B cells in xenografts before implantation (A), or after treatment with anti-KLH (B), or -005 (C). Methods are described in Example 15.

FIG. 23 shows the binding of -003 and -005 to wild type and mutant human CD38 as measured by ELISA. 23A: Binding of -003 and -005 to T237A mutant human CD38. 23B: Binding of -003 and -005 to Q272R mutant human CD38. 23C: Binding of -003 and -005 to S274F mutant human CD38. Methods are described in Example 17.

FIG. 24 shows the effect of -003 and -005 compared to HuMab-KLH on proliferation (A), IL-6 production (B) and IFN-γ production (C) of human PBMCs. Methods are described in Examples 18, 19 and 20, respectively.

FIG. 25 shows the enzymatic production of cGDPribose in the presence of various concentrations of -003 (B), -005 (C), -024 (D) or anti-KLH (A). Methods are described in Example 23.

FIG. 26 shows the comparison between -003, -005 and Morphosys antibody TH-3079 in CDC of CHO-CD38 cells (26A), CDC of Daudi cells (26B), and ADCC of Daudi cells (26C). Methods are described in Example 24.

DETAILED DESCRIPTION OF THE INVENTION

Definitions

Figure 3:
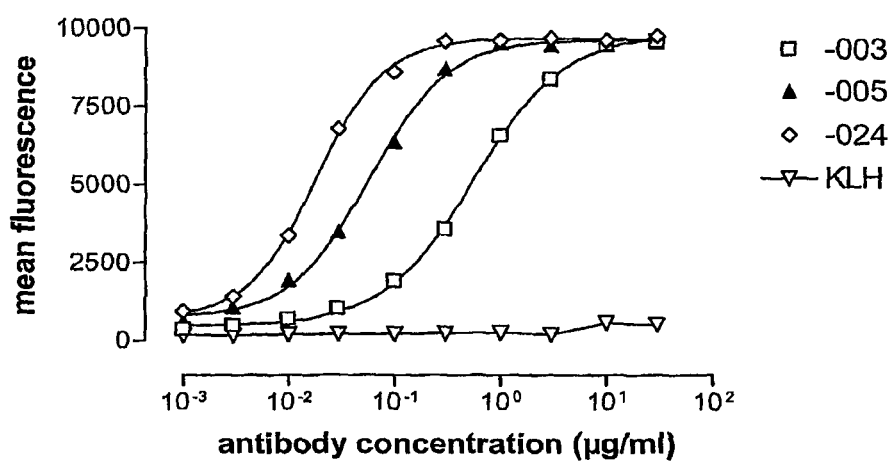
FIG. 3 shows the binding of -003, -005, -024 and HuMab-KLH to multiple myeloma cells. The experimental setup is described in Example 4.

A "non-agonistic antibody which binds to CD38" or "anti-CD38 antibody" when used herein refer to an antibody which upon binding to CD38 does not induce significant proliferation of peripheral blood mononuclear cells when compared to the proliferation induced by an isotype control antibody or medium alone (as assayed e.g. as described herein below in Example 18). In one embodiment, an anti-CD38 antibody used in the invention is not only a non-agonist, but even an antagonist of CD38.

The terms "CD38" and "CD38 antigen" are used interchangeably herein, and include any variants, isoforms and species homologs of human CD38, which are naturally expressed by cells or are expressed on cells transfected with the CD38 gene. Synonyms of CD38, as recognized in the art, include ADP ribosyl cyclase 1, cADPr hydrolase 1, Cd38-rs1, Cyclic ADP-ribose hydrolase 1, I-19, NIM-R5 antigen. The term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions can be further subdivided into regions of hypervariability (or hypervariable regions which can be hypervariable in sequence and/or form of structurally defined loops), also termed complementarity determining regions (CDRs), interspersed with regions that are more conserved, termed framework regions (FRs).

Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions for significant periods of time such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen).

The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and the first component (Clq) of the classical complement system.

An anti-CD38 antibody may be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of CD38.

As indicated above, the term antibody herein, unless otherwise stated or clearly contradicted by context, includes fragments of an antibody that retain the ability to specifically bind to an antigen. It has been shown that the antigen-binding function of an antibody can be performed by fragments of a full-length antibody. Examples of binding fragments encompassed within the term "antibody" include (i) a Fab fragment, a monovalent fragment consisting of the $V_L$, $V_H$, $C_L$ and $C_H1$ domains; (ii) F(ab)$_2$ and F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Other forms of single chain antibodies, such as diabodies are included within the term antibody. Although such fragments are generally included within the meaning of antibody, they collectively and each independently are unique features of the present invention, exhibiting different biological properties and utility. These and other useful antibody fragments in the context of the present invention are discussed further herein.

It also should be understood that the term antibody also generally includes polyclonal antibodies, monoclonal antibodies (mAbs), antibody-like polypeptides, such as chimeric antibodies and humanized antibodies, anti-idiotypic (anti-Id) antibodies to antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The term "bispecific molecule" is intended to include any agent, such as a protein, peptide, or protein or peptide complex, which has two different binding specificities. For example, the molecule may bind to, or interact with, (a) a cell surface antigen and (b) an Fc receptor on the surface of an effector cell. The term "multispecific molecule" is intended to include any agent, for instance a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the present invention includes, but is not limited to, bispecific, trispecific, tetraspecific, and other multispecific molecules which are directed to CD38, and to other cell surface antigens or targets, such as Fc receptors on effector cells.

The term "bispecific antibodies" is intended to include any anti-CD38 antibody, which is a bispecific molecule. The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see for instance Holliger, P. et al., PNAS USA 90, 6444-6448 (1993), Poljak, R. J. et al., Structure 2, 1121-1123 (1994)).

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, neutronphils, polymorphonuclear cells, granulocytes, mast cells, and basophils. Some effector cells express specific Fc receptors and carry out specific immune functions. In some embodiments, an effector cell is capable of inducing antibody-dependent cellular cytotoxicity (ADCC), such as a neutrophil capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen, target cell, or microorganism. The expression of a particular FcR on an effector cell can be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

The term "human antibody", as used herein, is intended to include antibodies having variable and constant regions derived from human germline immunoglobulin sequences. The human antibodies of the present invention may include amino acid residues not encoded by human germline immunoglobulin sequences (for instance mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline VH or VL variable region gene segment. Typically, a human antibody derived from a particular human germline VH or VL variable region gene segment sequence will display no more than 10 amino acid differences, such as no more than 5, for instance no more than 4, 3, 2, or 1 amino acid difference from the amino acid sequence encoded by the germline immunoglobulin gene.

A "chimeric" antibody is an antibody that contains one or more regions from one antibody and one or more regions from one or more other antibodies derived from another species. A monovalent chimeric antibody is a dimer (HL)) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody may also be produced, for example, by employing a CH region that oligomerizes (for instance from an IgM H chain, or p chain). Typically, a chimeric antibody refers to an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for instance U.S. Pat. No. 4,816,567 and Morrison et al., PNAS USA 81, 6851-6855 (1984)). Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

A "humanized" antibody is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired antigen-binding characteristics such as specificity, and affinity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further optimize antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody optionally also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell. A monoclonal antibody may be abbreviated as mAb.

As used herein, "specific binding" refers to an antibody binding to a predetermined antigen. Typically, the antibody, binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by surface plasmon resonance (SPR) technology in a BIAcore 3000 instrument using recombinant CD38 as the ligand and the antibody as the analyte. The antibody may bind to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term specificity herein refers to the ability of a CD38 binding peptide, such as an anti-CD38 antibody, to recognize an epitope within CD38, while only having little or no detectable reactivity with other portions of CD38 (including other epitopes that are bound by other anti-CD38 antibodies). Specificity can be relatively determined by competition assays as described herein. Specificity can more particularly be determined by any of the epitope identification/characterization techniques described herein or their equivalents known in the art.

An antibody specific for a particular antigenic determinant may nonetheless cross-react with other biomolecules that may be present in some biological context with CD38. More typically, an anti-CD38 antibody, may cross-react with CD38 homologues from other species. In either or both contexts, typically such cross-reactive antibodies are selective for human CD38 with respect to relevant structure and/or environmental factors.

The term "selectivity" herein refers to the preferential binding of an anti-CD38 antibody, for a particular region, target, or peptide; typically a region or epitope in CD38, as opposed to one or more other biological molecules, structures, cells, tissues, etc. In one embodiment, an anti-CD38 antibody used in the present invention is selective for a portion of CD38 in the context of colon cancer cells (i.e., the anti-CD38 antibody will selectively bind to the portion of CD38 over other components of a colon cancer cell).

The term "$k_d$" (sec$^{-1}$), as used herein, is intended to refer to the dissociation equilibrium rate constant of a particular antibody-antigen interaction. Said value is also referred to as the $k_{off}$ value.

The term "$k_a$" (M$^{-1}$×sec$^{-1}$), as used herein, is intended to refer to the association equilibrium rate constant of a particular antibody-antigen interaction.

The term "$K_D$" (M), as used herein, is intended to refer to the dissociation equilibrium constant of a particular antibody-antigen interaction.

The term "$K_A$" (M$^{-1}$), as used herein, is intended to refer to the association equilibrium constant of a particular antibody-antigen interaction and is obtained by dividing the $k_a$ by the $k_d$.

As used herein, "isotype" refers to the antibody class (for instance IgG1, IgG2, IgG3, IgG4, IgD, IgA, IgE, or IgM) that is encoded by heavy chain constant region genes.

"Target cell" shall mean any undesirable cell in an individual. In some embodiments, the target cell is a cell expressing or overexpressing CD38. Cells expressing CD38 typically include hemopoietic cells, such as medullary thymocytes, activated T and B cells, 80% of resting NK cells and monocytes, lymph node germinal center lymphoblasts, plasma B cells and some intrafollicular cells, dendritic cells, normal bone marrow cells, particular precursor cells, 50-80% of umbilical cord blood cells, erythrocytes and platelets. CD38 can also be expressed by non-hemopoietic cells, such as intra-epithelial cells and lamina propria lymphocytes in the gut, by Purkinje cells and neurofibrillary tangles in the brain, by epithelial cells in the prostate, 13-cells in the pancreas, osteoclasts in the bone, retinal cells in the eye, and sarcolemma of smooth and striated muscle. On malignant cells, CD38 is expressed in a variety of malignant hematological diseases, including but not restricted to multiple myeloma, primary or secondary plasma cell leukemia, B-cell chronic lymphocytic leukemia, B-cell acute lymphocytic leukemia, Waldenström macroglobulinemia, primary systemic amyloidosis, mantle-cell lymphoma, pro-lymphocytic/myelocytic leukemia, acute myeloid leukemia, chronic myeloid leukemia, follicular lymphoma, and NK-cell leukemia.

As used herein, the term "individual" includes any human or non-human animal. The term "non-human animal" includes all vertebrates, for instance mammals and non-mammals, such as non-human primates, sheep, dog, cow, chickens, amphibians, reptiles, etc.

"Treatment" means the administration of an effective amount of a therapeutically active compound of the present invention with the purpose of easing, ameliorating, or eradicating (curing) symptoms or disease states.

Aspects and Embodiments of the Invention

In a first main aspect, the invention relates to a method for inhibiting growth and/or proliferation of tumor cells expressing CD38 in an individual in need thereof, which method comprises administration to the said individual of
  i) a non-agonistic antibody which binds to, i.e. binds specifically to, CD38,
  ii) at least one corticosteroid, and
  iii) at least one non-corticosteroid chemotherapeutic agent.

In a further main aspect, the invention relates to a method for treating cancer involving tumor cells expressing CD38 in an individual in need thereof, which method comprises administration to the said individual of:

i) a non-agonistic antibody which binds to, i.e. binds specifically to, CD38,
ii) optionally at least one corticosteroid, and
iii) optionally at least one non-corticosteroid chemotherapeutic agent, such as a non-alkylating non-corticosteroid chemotherapeutic agent, followed by autologous peripheral stem cell or bone marrow transplantation.

In one embodiment of the above methods of the invention, said at least one non-corticosteroid chemotherapeutic agent comprises a cytotoxic agent and/or an angiogenesis inhibitor. In a further embodiment, said at least one non-corticosteroid chemotherapeutic agent comprises an alkylating agent.

In an even further embodiment, said at least one non-corticosteroid chemotherapeutic agent comprises one or more agents selected from the group consisting of: melphalan, mechlorethamine, thioepa, chlorambucil, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In a further embodiment, said at least one non-corticosteroid chemotherapeutic agent comprises a glutamic acid derivative, such as thalidomide (Thalomid®) or a thalidomide analog, e.g. CC-5013 (lenalidomide, Revlimid™) or CC4047 (Actimid™).

In an even further embodiment, said at least one non-corticosteroid chemotherapeutic agent comprises a proteasome inhibitor, such as bortezomib (Velcade®) or vinca alkaloid, such as vincristine or an anthracycline, such as doxorubicin.

In one embodiment of the methods of the invention, said at least one corticosteroid comprises a glucocorticoid. In a further embodiment, said at least one corticosteroid comprises prednisone or dexamethasone.

In further embodiments of the invention, said at least one corticosteroid comprises prednisone and said at least one non-corticosteroid chemotherapeutic agent comprises melphalan.

In even further embodiments of the invention, said at least one corticosteroid comprises prednisone and said at least one non-corticosteroid chemotherapeutic agent comprises thalidomide.

In even further embodiments of the invention, said at least one corticosteroid comprises prednisone and said at least one non-corticosteroid chemotherapeutic agent comprises melphalan and thalidomide.

In even further embodiments of the invention, said at least one corticosteroid comprises dexamethasone and said at least one non-corticosteroid chemotherapeutic agent comprises thalidomide and/or lenalidomide.

In even further embodiments of the invention, said at least one corticosteroid comprises dexamethasone and said at least one non-corticosteroid chemotherapeutic agent comprises vincristine and/or doxorubicin.

In one embodiment of the methods of the invention, said non-agonistic antibody which binds to CD38 is a monoclonal antibody, such as a human monoclonal antibody.

In a further embodiment of the invention, said antibody is an antagonist of CD38.

In further embodiment of the invention, said antibody is:
an antibody that does not induce release of significant IL-6 by human monocytes or peripheral blood mononuclear cells as determined by the method described in Example 19 of the specification
and/or
an antibody that does not induce release of detectable IFN-γ by human T cells or peripheral blood mononuclear cells as determined by the method described in Example 20 of the specification
and/or
an antibody that is internalized by CD38 expressing cells; such as internalized by CHO-CD38 cells within 5 to 15 minutes at 37° C. by the method as described in Example 12 of the specification
and/or
an antibody that induces ADCC; such as with an $EC_{50}$ value of below 15 ng/ml, such as below 10 ng/ml in Daudi-luc cells and with an $EC_{50}$ value of below 75 ng/ml, such as below 50 ng/ml, 30 ng/ml or 10 ng/ml in MM cells as determined by the method described in Example 5 of the specification
and/or
an antibody that induces CDC in the presence of complement; such as with an $EC_{50}$ value of below 5 µg/ml, such as below 1 µg/ml in daudi-luc or CD38-CHO cells by the method described in Example 6 of the specification
and/or
an antibody that inhibits the synthesis of cGDPR
and/or
an antibody that inhibits the synthesis of cADPR
and/or
an antibody that binds to human CD38 with an affinity ($K_D$) of below $10^{-8}$ M, such as in the range of from $10^{-8}$ M to $10^{-11}$ M, for example in the range of from $7\times10^{-9}$ M to $10^{-10}$ M, as determined by surface plasmon resonance as described in Example 20 of the specification
and/or
an antibody that inhibits the synthesis of cGDPR by at least 25%, such as at least 30% after 90 minutes at a concentration of 3 µg/ml as determined by spectophotometric method described in Example 24 of the specification
and/or
an antibody that inhibits the synthesis of cADPR by at least 25%, such as at least 30% after 90 minutes at a concentration of 3 µg/ml as determined by the HPLC method described in Munshi et al., J. Biol. Chem. 275, 21566-21571 (2000).

In one embodiment, the non-agonistic CD38 antibody used in the invention is the antibody -003. -003 is a human monoclonal IgG1 antibody having a $V_L$ region consisting of the sequence of SEQ ID No:2 and a $V_H$ region consisting of the sequence of SEQ ID No:7.

In another embodiment, the non-agonistic CD38 antibody used in the invention is the antibody -005. -005 is a human monoclonal IgG1 antibody having a $V_L$ region consisting of the sequence of SEQ ID No:12 and a $V_H$ region consisting of the sequence of SEQ ID No:17.

In a further embodiment, the non-agonistic CD38 antibody used in the invention is the antibody -024. -024 is a human monoclonal IgG1 antibody having a $V_L$ region consisting of the sequence of SEQ ID No:22 and a $V_H$ region consisting of the sequence of SEQ ID No:27.

In one embodiment, the non-agonistic CD38 antibody used in the invention is an antibody binding to human CD38 encoded by human light chain and human heavy chain nucleic acids comprising nucleotide sequences in their variable regions as set forth in SEQ ID No:1 and SEQ ID No:6, respectively.

In one embodiment, the non-agonistic CD38 antibody used in the invention is an antibody binding to human CD38 encoded by human light chain and human heavy chain nucleic acids comprising nucleotide sequences in their variable regions as set forth in SEQ ID No:11 and SEQ ID No:16, respectively.

In one embodiment, the non-agonistic CD38 antibody used in the invention is an antibody binding to human CD38 encoded by human light chain and human heavy chain nucleic acids comprising nucleotide sequences in their variable regions as set forth in SEQ ID No:21 and SEQ ID No:26, respectively.

In a yet further embodiment, the non-agonistic CD38 antibody used in the invention is one of the antibodies described in WO2005/103083 (Morphosys), in particular an antibody comprising one or more of the sequences given in FIG. 1b and/or the sequences given in FIG. 2B of WO 2005/103083.

Antibodies interact with target antigens primarily through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see for instance Riechmann, L. et al., Nature 332, 323-327 (1998), Jones, P. et al., Nature 321, 522-525 (1986) and Queen, C. et al., PNAS USA 86, 10029-10033 (1989)).

Since it is well known in the art that antibody heavy chain CDR3 domains play a particularly important role in the binding specificity/affinity of an antibody for an antigen (Ditzel H J, et al., J Immunol. 157(2), 739-49 (1996), Barbas S M et al., J. Am. Chem. Soc. 116, 2161-2162 (1994), and Barbas S M et al., Proc Natl Acad Sci USA 92(7), 2529-33 (1995), the antibodies used in the invention may comprise the heavy chain CDR3s of -003 or -005 or -024. The antibodies used in the invention may also comprise the heavy and light chain CDR3s of -003 or -005 or -024.

Thus, in a further embodiment of the methods of the invention, said antibody is an antibody comprising a $V_H$ CDR3 having the sequence as set forth in SEQ ID No:10 or an antibody which competes for CD38 binding with said antibody, e.g. by binding the same epitope as said antibody.

In one embodiment, the competition is determined by use of an ELISA as described in the Examples section.

In another embodiment, the competition is determined by use of a FACS as described in the Examples section.

In another embodiment, said antibody is an antibody comprising a $V_L$ CDR3 having the sequence as set forth in SEQ ID No:5 and a $V_H$ CDR3 having the sequence as set forth in SEQ ID No:10.

In another embodiment, said antibody is an antibody comprising human light chain and human heavy variable regions, wherein the light chain variable region comprises a $V_L$ CDR1 having the sequence as set forth in SEQ ID No:3, a $V_L$ CDR2 having the sequence as set forth in SEQ ID No:4 and a $V_L$ CDR3 having the sequence as set forth in SEQ ID No:5, and the heavy chain variable region comprises a $V_H$ CDR1 having the sequence as set forth in SEQ ID No:8, a $V_H$ CDR2 having the sequence as set forth in SEQ ID No:9 and a $V_H$ CDR3 having the sequence as set forth in SEQ ID No:10.

In another embodiment, said antibody is an antibody comprising a $V_L$ region having the amino acid sequence as set forth in SEQ ID No:2 or a $V_L$ region having at least about 90%, such as at least about 95% amino acid sequence identity to the sequence as set forth in SEQ ID No:2.

In another embodiment, said antibody is an antibody comprising a $V_H$ region having the amino acid sequence as set forth in SEQ ID No:7 or a $V_H$ region having at least about 90%, such as at least about 95% amino acid sequence identity to the sequence as set forth in SEQ ID No:7 or a $V_H$ region having 1-5, such as 1-3 amino acid substitutions, deletions or additions compared to the sequence as set forth in SEQ ID No:7.

In another embodiment, said antibody is an antibody comprising a $V_H$ CDR3 having the sequence as set forth in SEQ ID No:20 or an antibody which competes for CD38 binding with said antibody, e.g. by binding the same epitope as said antibody.

In another embodiment, said antibody is an antibody comprising a $V_L$ CDR3 having the sequence as set forth in SEQ ID No:15 and a $V_H$ CDR3 having the sequence as set forth in SEQ ID No:20.

In another embodiment, said antibody is an antibody comprising human light chain and human heavy variable regions, wherein the light chain variable region comprises a $V_L$ CDR1 having the sequence as set forth in SEQ ID No:13, a $V_L$ CDR2 having the sequence as set forth in SEQ ID No:14 and a $V_L$ CDR3 having the sequence as set forth in SEQ ID No:15, and the heavy chain variable region comprises a $V_H$ CDR1 having the sequence as set forth in SEQ ID No:18, a $V_H$ CDR2 having the sequence as set forth in SEQ ID No:19 and a $V_H$ CDR3 having the sequence as set forth in SEQ ID No:20.

In another embodiment, said antibody is an antibody comprising a $V_L$ region having the amino acid sequence as set forth in SEQ ID No:12 or a $V_L$ region having at least about 90%, such as at least about 95% amino acid sequence identity to the sequence according to SEQ ID No:12.

In another embodiment, said antibody is an antibody comprising a $V_H$ region having the amino acid sequence as set forth in SEQ ID No:17 or a $V_H$ region having at least about 90%, such as at least about 95% amino acid sequence identity to the sequence as set forth in SEQ ID No:17 or a $V_H$ region having 1-5, such as 1-3 amino acid substitutions, deletions or additions compared to the sequence as set forth in SEQ ID No:17.

In another embodiment, said antibody is an antibody comprising a $V_H$ CDR3 having the sequence as set forth in SEQ ID No:30 or an antibody which competes for CD38 binding with said antibody, e.g. by binding the same epitope as said antibody.

In another embodiment, said antibody is an antibody comprising a $V_L$ CDR3 having the sequence as set forth in SEQ ID No:25 and a $V_H$ CDR3 having the sequence as set forth in SEQ ID No:30.

In another embodiment, said antibody is an antibody comprising human light chain and human heavy variable regions, wherein the light chain variable region comprises a $V_L$ CDR1 having the sequence as set forth in SEQ ID No:23, a $V_L$ CDR2 having the sequence as set forth in SEQ ID No:24 and a $V_L$ CDR3 having the sequence as set forth in SEQ ID No:25, and the heavy chain variable region comprises a $V_H$ CDR1 having the sequence as set forth in SEQ ID No:28, a $V_H$ CDR2 having the sequence as set forth in SEQ ID No:29 and a $V_H$ CDR3 having the sequence as set forth in SEQ ID No:30.

In another embodiment, wherein said antibody is an antibody comprising a $V_L$ region having the amino acid sequence as set forth in SEQ ID No:22 or a $V_L$ region having at least about 90%, such as at least about 95% amino acid sequence identity to the sequence according to SEQ ID No:22.

In another embodiment, said antibody is an antibody comprising a $V_H$ region having the amino acid sequence as set forth in SEQ ID No:27 or a $V_H$ region having at least about 90%, such as at least about 95% amino acid sequence identity to the sequence according to SEQ ID No:27 or a $V_H$ region having 1-5, such as 1-3 amino acid substitutions, deletions or additions compared to the sequence as set forth in SEQ ID No:27.

In one embodiment of the methods of the invention, said at least one non-corticosteroid chemotherapeutic agent comprises one or more agents selected from the group consisting of: melphalan, mechlorethamine, thioepa, chlorambucil, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In one embodiment of the methods of the invention, said at least one non-corticosteroid chemotherapeutic agent comprises melphalan, and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In another embodiment, said at least one non-corticosteroid chemotherapeutic agent comprises a glutamic acid derivative, such as thalidomide (Thalomid®) or a thalidomide analog, e.g. CC-5013 (lenalidomide, Revlimid™) or CC4047 (Actimid™), and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In another embodiment, said at least one non-corticosteroid chemotherapeutic agent comprises a glutamic acid derivative, such as thalidomide (Thalomid®) or a thalidomide analog, e.g. CC-5013 (lenalidomide, Revlimid™) or CC4047 (Actimid™), and said antibody is a human monoclonal IgG1 antibody having a $V_L$ region consisting of the sequence of SEQ ID No:12 and a $V_H$ region consisting of the sequence of SEQ ID No:17.

In another embodiment, said at least one non-corticosteroid chemotherapeutic agent comprises a proteasome inhibitor, such as bortezomib (Velcade®), and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises dexamethasone, said at least one non-corticosteroid chemotherapeutic agent comprises a proteasome inhibitor, such as bortezomib (Velcade®), and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In another embodiment, said at least one non-corticosteroid chemotherapeutic agent comprises a vinca alkaloid, such as vincristine, and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In another embodiment, said at least one non-corticosteroid chemotherapeutic agent comprises an anthracycline, such as doxorubicin, and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises a glucocorticoid, and said antibody is selected from the group consisting of:
- a human monoclonal IgG1 antibody having a $V_L$ region consisting of the sequence of SEQ ID No:2 and a $V_H$ region consisting of the sequence of SEQ ID No:7,
- a human monoclonal IgG1 antibody having a $V_L$ region consisting of the sequence of SEQ ID No:12 and a $V_H$ region consisting of the sequence of SEQ ID No:17, and
- a human monoclonal IgG1 antibody having a $V_L$ region consisting of the sequence of SEQ ID No:22 and a $V_A$ region consisting of the sequence of SEQ ID No:27.

In another embodiment, said at least one corticosteroid comprises prednisone, and said antibody is selected from the group consisting of:
- a human monoclonal IgG1 antibody having a $V_L$ region consisting of the sequence of SEQ ID No:2 and a $V_H$ region consisting of the sequence of SEQ ID No:7, a human monoclonal IgG1 antibody having a $V_L$ region consisting of the sequence of SEQ ID No:12 and a $V_A$ region consisting of the sequence of SEQ ID No:17, and a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises prednisone and said at least one non-corticosteroid chemotherapeutic agent comprises melphalan, and said antibody is selected from the group consisting of:

a human monoclonal IgG1 antibody having a $V_L$ region consisting of the sequence of
SEQ ID No:2 and a $V_A$ region consisting of the sequence of SEQ ID No:7, a human monoclonal IgG1 antibody having a $V_L$ region consisting of the sequence of SEQ ID No:12 and a $V_H$ region consisting of the sequence of SEQ ID No:17, and a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises prednisone and said at least one non-corticosteroid chemotherapeutic agent comprises thalidomide, and said antibody is selected from the group consisting of:

a human monoclonal IgG1 antibody having a $V_L$ region consisting of the sequence of SEQ ID No:2 and a $V_H$ region consisting of the sequence of SEQ ID No:7, a human monoclonal IgG1 antibody having a $V_L$ region consisting of the sequence of SEQ ID No:12 and a $V_A$ region consisting of the sequence of SEQ ID No:17, and a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises prednisone and said at least one non-corticosteroid chemotherapeutic agent comprises melphalan and thalidomide, and said antibody is selected from the group consisting of: a human monoclonal IgG1 antibody having a $V_L$ region consisting of the sequence of SEQ ID No:2 and a $V_H$ region consisting of the sequence of SEQ ID No:7, a human monoclonal IgG1 antibody having a $V_L$ region consisting of the sequence of SEQ ID No:12 and a $V_H$ region consisting of the sequence of SEQ ID No:17, and a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises dexamethasone, and said antibody is selected from the group consisting of:

a human monoclonal IgG1 antibody having a $V_L$ region consisting of the sequence of SEQ ID No:2 and a $V_H$ region consisting of the sequence of SEQ ID No:7, a human monoclonal IgG1 antibody having a $V_L$ region consisting of the sequence of SEQ ID No:12 and a $V_H$ region consisting of the sequence of SEQ ID No:17, and a human monoclonal IgG1 antibody having a $V_L$ region consisting of the sequence of SEQ ID No:22 and a $V_H$ region consisting of the sequence of SEQ ID No:27.

In another embodiment, said at least one corticosteroid comprises dexamethasone and said at least one non-corticosteroid chemotherapeutic agent comprises thalidomide and/or lenalidomide, and said antibody is selected from the group consisting of:

a human monoclonal IgG1 antibody having a $V_L$ region consisting of the sequence of SEQ ID No:2 and a $V_H$ region consisting of the sequence of SEQ ID No:7, a human monoclonal IgG1 antibody having a $V_L$ region consisting of the sequence of SEQ ID No:12 and a $V_H$ region consisting of the sequence of SEQ ID No:17, and a human monoclonal IgG1 antibody having a $V_L$ region consisting of the sequence of
SEQ ID No:22 and a $V_H$ region consisting of the sequence of SEQ ID No:27.

In another embodiment, said at least one corticosteroid comprises dexamethasone and said at least one non-corticosteroid chemotherapeutic agent comprises vincristine and/or doxorubicin, and said antibody is selected from the group consisting of:

a human monoclonal IgG1 antibody having a $V_L$ region consisting of the sequence of SEQ ID No:2 and a $V_H$ region consisting of the sequence of SEQ ID No:7, a human monoclonal IgG1 antibody having a $V_L$ region consisting of the sequence of SEQ ID No:12 and a $V_H$ region consisting of the sequence of SEQ ID No:17, and a human monoclonal IgG1 antibody having a $V_L$ region consisting of the sequence of SEQ ID No:22 and a $V_H$ region consisting of the sequence of SEQ ID No:27.

Antibodies suitable for use in the present invention also include variants of the antibodies of the Examples. A functional variant of a $V_L$, $V_H$, or CDR used in the context of a CD38 antibody still allows the antibody to retain at least a substantial proportion (at least about 50%, 60%, 70%, 80%, 90%, 95% or more) of the affinity/avidity and/or specificity/selectivity of the parent antibody and in some cases such an antibody may be associated with greater affinity, selectivity, and/or specificity than the parent antibody.

A "variant" anti-CD38 antibody is an antibody that differs from a parent antibody (typically generated by immunization) by one or more suitable amino acid residue alterations, that is substitutions, deletions, insertions, or terminal sequence additions, in the CDRs or other $V_H$ and/or $V_L$ sequences (provided that at least a substantial amount of the epitope binding characteristics of the parent antibody are retained, if not improved upon, by such changes).

Thus, for example, in an antibody variant one or more amino acid residues may be introduced or inserted in or adjacent to one or more of the hypervariable regions of a parent antibody, such as in one or more CDRs. An anti-CD38 antibody variant may comprise any number of inserted amino acid residues, provided again that at least a substantial amount of the epitope binding characteristics of the parent antibody are retained. An anti-CD38 antibody variant of the present invention may for example comprise from about 1-30 inserted amino acid residues, for instance from about 1-10, such as for instance from about 2-10, for instance from 2-5 or such as from about 1-5 inserted amino acid residues. Likewise, an anti-CD38 antibody variant of the present invention may for example comprise from about 1-30 deleted amino acid residues, for instance from about 1-10, such as for instance from about 2-10, for instance from 2-5 or such as from about 1-5 deleted amino acid residues. Likewise, an anti-CD38 antibody variant of the present invention may for example comprise from about 1-30 substituted amino acid residues, for instance from about 1-10, such as for instance from about 2-10, for instance from 2-5 or such as from about 1-5 substituted amino acid residues. Likewise, an anti-CD38 antibody variant useful for the present invention may for example comprise from about 1-30 terminal sequence amino acid residue additions, for instance from about 1-10, such as for instance from about 2-10, for instance from 2-5 or such as from about 1-5 terminal sequence amino acid residue additions. A antibody variant of the present invention may also comprise a combination of two or more of such insertions, deletions, substitutions and terminal sequence amino acid residue additions, provided that the variant possesses at least a substantial proportion of the parent antibodies affinity, specificity, and/or selectivity with respect to one or more CD38 epitopes.

In one embodiment, the antibody used in the invention comprises a variant $V_H$ CDR3 consisting essentially of a sequence having at least about 80%, such as at least about 85%, for instance at least about 90%, such as at least about 95% amino acid sequence identity to a sequence according to any one of SEQ ID No:10 or SEQ ID No:20 or SEQ ID No:30, wherein the antibody has at least a substantial proportion (at least about 50%, 60%, 70%, 80%, 90%, 95% or more) of the epitope binding characteristics of an antibody having a variant $V_H$ CDR3 sequence of SEQ ID No:10 or SEQ ID No:20 or SEQ ID No:30, respectively, such as an antibody having a $V_H$ sequence of SEQ ID No:7 or SEQ ID No:17 or SEQ ID No:27, respectively, such as an antibody having a $V_H$ sequence of SEQ ID No:7 and a $V_L$ sequence of SEQ ID No:2, or an antibody having a $V_H$ sequence of SEQ ID No:17 and a $V_L$ sequence of SEQ ID No:12, or an antibody having a $V_H$ sequence of SEQ ID No:27 and a $V_L$ sequence of SEQ ID No:22, respectively.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at www.gcg.com), using a NWS-gapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci 4, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of the present invention, conservative substitutions may be defined by substitutions within the classes of amino acids reflected in one or more of the following three tables:

| Amino acid residue classes for conservative substitutions | |
|---|---|
| Acidic Residues | Asp and Glu |
| Basic Residues | Lys, Arg, and His |
| Hydrophilic Uncharged Residues | Ser, Thr, Asn, and Gln |
| Aliphatic Uncharged Residues | Gly, Ala, Val, Leu, and Ile |
| Non-polar Uncharged Residues | Cys, Met, and Pro |
| Aromatic Residues | Phe, Tyr, and Trp |

| Alternative conservative amino acid residue substitution classes | | | |
|---|---|---|---|
| 1 | Ala (A) | Ser (S) | Thr (T) |
| 2 | Asp (D) | Glu (E) | |
| 3 | Asp (N) | Gln (Q) | |
| 4 | Arg (R) | Lys (K) | |
| 5 | Ile (I) | Leu (L) | Met (M) |
| 6 | Phe (F) | Tyr (Y) | Trp (W) |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine. Additional groups of amino acids may also be formulated using the principles described in, e.g., Creighton (1984) Proteins: Structure and Molecular Properties (2d Ed. 1993), W.H. Freeman and Company.

Where hypervariable region insertions are made to generate a variant antibody, the typical range of lengths of the hypervariable region in question in known antibodies should be taken into consideration. For example, for the first hypervariable region of a light chain variable domain, insertions may be introduced into the $V_L$ CDR1 sequence of a parent antibody while retaining a substantially similar and thereby expected appropriate size, which according to Kabat et al., supra, e.g., typically has an overall of about 9-20 (e.g., about 10-17) residues. Similarly, $V_L$ CDR2 typically has an overall length from about 5-10 residues; $V_L$ CDR3 typically has a length of about 7-20 residues; $V_H$ CDR1 typically has a length of about 10-15 residues; $V_H$ CDR2 typically has a length of about 15-20 residues; and $V_H$ CDR3 typically has a length of about 6-30 residues (e.g., 3-25 residues). Insertions in the $V_H$ region typically are made in $V_H$ CDR3 and typically near the C-terminal of the domain, such as about residues 97-102 of the parent $V_H$ CDR3 (for instance adjacent to, or C-terminal in sequence to, residue number 100 of the parent $V_H$ CDR3 sequence) using the alignment and numbering as described in Kabat. Antibody variants with inserted amino acid residue(s) in a hypervariable region thereof may be prepared randomly, especially where the starting binding affinity of the parent antibody for the target antigen is such that randomly produced antibody variants may be readily screened. For example, phage display provides a convenient method of screening such random variants.

In a further embodiment, the non-agonistic CD38 antibody used in the invention is an antibody which is characterized with respect to its ability to compete (competitively inhibit) or cross-compete (i.e., relatively partially inhibit epitope binding) with an antibody having a $V_L$ sequence of SEQ ID No:2 and a $V_H$ sequence of SEQ ID No:7 (such as antibody -003), or an antibody having a $V_L$ sequence of SEQ ID No:12 and a $V_H$ sequence of SEQ ID No:17 (such as antibody -005) or an antibody having a $V_L$ sequence of SEQ ID No:22 and a $V_H$ sequence of SEQ ID No:27, (such as antibody -024), for binding to CD38. Such an antibody may be, for instance, a Fab fragment, derived from an antibody that binds to an epitope identical to or overlapping with an epitope bound by an antibody having a $V_L$ sequence of SEQ ID No:2 and a $V_H$ sequence of SEQ ID No:7, or an antibody having a $V_L$ sequence of SEQ ID No:12 and a $V_H$ sequence of SEQ ID No:17 or an antibody having a $V_L$ sequence of SEQ ID No:22 and a $V_H$ sequence of SEQ ID No:27. Competition for binding to CD38 or a portion of CD38 by two or more antibodies may be determined by any suitable technique. In one embodiment, competition is determined for example as described in Example 7, 8 and 9.

Often competition is marked by a significantly greater relative inhibition than about 5% as determined by ELISA and/or FACS analysis. It may be desirable to set a higher threshold of relative inhibition as a criteria/determinant of what is a suitable level of competition in a particular context (e.g., where the competition analysis is used to select or screen for new antibodies designed with the intended function of blocking the binding of another peptide or molecule binding to CD38 (e.g., the natural binding partners of CD38 such as CD31, also called CD31 antigen, EndoCAM, GPIIA', PECAM-1, platelet/endothelial cell adhesion molecule or naturally occurring anti-CD38 antibody)). Thus, for example, it is possible to set a criteria for competitiveness wherein at least about 10% relative inhibition is detected; at least about 15% relative inhibition is detected; or at least about 20% relative inhibition is detected before an antibody is considered sufficiently competitive. In cases where epitopes belonging to competing antibodies are closely located in an antigen, competition may be marked by greater than about 40% relative inhibition of CD38 binding (e.g., at least about 45% inhibition, such as at least about 50% inhibition, for instance at least about 55% inhibition, such as at least about 60% inhibition, for instance at least about 65% inhibition, such as at least about 70% inhibition, for instance at least about 75% inhibition, such as at least about 80% inhibition, for instance at least about 85% inhibition, such as at least about 90% inhibition, for instance at least about 95% inhibition, or higher level of relative inhibition).

In a further embodiment, the non-agonistic CD38 antibody used in the invention is an antibody that specifically binds to a CD38 epitope that also is specifically bound by an antibody having a $V_L$ sequence of SEQ ID No:2 and a $V_H$ sequence of SEQ ID No:7 (such as antibody -003), or an antibody having a $V_L$ sequence of SEQ ID No:12 and a $V_H$ sequence of SEQ ID No:17 (such as antibody -005) or an antibody having a $V_L$ sequence of SEQ ID No:22 and a $V_H$ sequence of SEQ ID No:27 (such as antibody -024).

A CD38 epitope bound by an antibody having a $V_L$ sequence of SEQ ID No:2 and a $V_H$ sequence of SEQ ID No:7 (such as the antibody -003), or an antibody having a $V_L$ sequence of SEQ ID No:12 and a $V_H$ sequence of SEQ ID No:17 (such as the antibody -005) or an antibody having a $V_L$ sequence of SEQ ID No:22 and a $V_H$ sequence of SEQ ID No:27 (such as antibody -024), may be identified via standard mapping and characterization techniques, further refinement of which may be identified by any suitable technique, numerous examples of which are available to the skilled artisan. These techniques may also be used to identify and/or characterize epitopes for anti-CD38 antibodies generally. As one example of such mapping/characterization methods, an epitope for an anti-CD38 antibody may be determined by epitope "foot-printing" using chemical modification of the exposed amines/carboxyls in the CD38 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry. See, e.g., Ehring H, Analytical Biochemistry, 267(2) 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding may be identified that way. See for instance Ernst Schering Res Found Workshop. (44), 149-67 (2004), Huang et al., Journal of Molecular Biology 281(1), 61-67 (1998) and Saito and Patterson, Methods. 9(3), 516-24 (1996).

Epitope mapping/characterization may also be performed using mass spectrometry methods. See for instance Downward, J Mass Spectrom. 35(4), 493-503 (2000) and Kiselar and Downard, Anal Chem. 71(9), 1792-801 (1999).

Protease digestion techniques may also be useful in the context of epitope mapping and identification. Antigenic determinant-relevant regions/sequences may be determined by protease digestion, e.g. by using trypsin in a ratio of about 1:50 to CD38 overnight (O/N) digestion at 37° C. and pH 7-8, followed by mass spectrometry (MS) analysis for peptide identification. The peptides protected from trypsin cleavage by the antibody may subsequently be identified by comparison of samples subjected to trypsin digestion and samples incubated with antibody and then subjected to digestion by e.g. trypsin (thereby revealing a foot print for the binder). Other enzymes like chymotrypsin, pepsin, etc. may also or alternatively be used in a similar epitope characterization method. An antibody which gives the significantly same result as an antibody having a $V_L$ sequence of SEQ ID No:2 and a $V_H$ sequence of SEQ ID No:7 (such as the antibody -003), or an antibody having a $V_L$ sequence of SEQ ID No:12 and a $V_H$ sequence of SEQ ID No:17 (such as the antibody -005) or an antibody having a $V_L$ sequence of SEQ ID No:22 and a $V_H$ sequence of SEQ ID No:27 (such as antibody -024) in these measurements are deemed to be an antibody that bind the same epitope as an antibody having a $V_L$ sequence of SEQ ID No:2 and a $V_H$ sequence of SEQ ID No:7 (such as the antibody -003), or an antibody having a $V_L$ sequence of SEQ ID No:12 and a $V_H$ sequence of SEQ ID No:17 (such as the antibody -005) or an antibody having a $V_L$ sequence of SEQ ID No:22 and a $V_H$ sequence of SEQ ID No:27 (such as antibody -024), respectively. See for instance Manca, Ann Ist Super Sanita. 27(1), 15-9 (1991) for a discussion of similar techniques.

Other methods potentially helpful in mapping epitopes include crystallography techniques, X-ray diffraction techniques (such as the X-ray diffraction/sequence study techniques developed by Poljak and others in the 1970s-1980s), and the application of Multipin Peptide Synthesis Technology. Computer-based methods such as sequence analysis and three dimensional structure analysis and docking may also be used to identify antigenic determinants. For example, an epitope may also be determined by molecular modeling using a structure of CD38 with docking of the structure of the Fab fragment of the individual monoclonal antibody. These and other mapping methods are discussed in Epitope Mapping A Practical Approach (Westwood and Hay Eds.) 2001 Oxford University Press.

An antibody used in the present invention may have any suitable affinity and/or avidity for one or more epitopes contained at least partially in CD38. Affinity refers to the strength of binding of the antibody to such an epitope. Typically, affinity is measured by dissociation constant $K_d$, defined as [Ab]×[Ag]/[Ab−Ag] where [Ab−Ag] is the molar concentration of the antibody-antigen complex (or the antibody-antigen complex), [Ab] is the molar concentration of the unbound antibody and [Ag] is the molar concentration of the unbound antigen. The affinity constant $K_a$ is defined by $1/K_d$. Suitable methods for determining specificity and affinity by competitive inhibition can be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993) and Muller, Meth. Enzymol. 92, 589-601 (1983).

Anti-CD38 antibodies used in the present invention may have an affinity for at least one epitope at least partially comprised in CD38 in the range of about $10^4$ to about $10^{10}$ $M^{-1}$. Such an antibody may have an affinity that is at least as great for CD38 as -003 and -005 and -024, and in some embodiments have an affinity that is at least about as great as -003 and -005 and -024. Affinity may be determined by any of the methods described elsewhere herein or their known equivalents in the art. An example of one method that may be used to determine affinity is provided in Scatchard analysis of Munson & Pollard, Anal. Biochem. 107, 220 (1980). Binding affinity also may be determined by equilibrium methods (for instance enzyme-linked immunoabsorbent assay (ELISA) or radioimmunoassay (RIA)) or kinetics analysis (for instance BIACORE™ analysis).

Typically, the disassociation constant for anti-CD38 antibodies used in the present invention is less than about 100 nM, less than about 50 nM, less than about 10 nM, about 5 nM or less, about 1 nM or less, about 0.5 nM or less, about 0.1 nM or less, about 0.01 nM or less, or even about 0.001 nM or less.

Non-limiting examples of anti-CD38 antibodies suitable for use in the present invention include (a) a complete functional, immunoglobulin molecule comprising: (i) two identical chimeric heavy chains comprising a variable region with a human B cell surface antigen specificity and human constant region and (ii) two identical all (i.e. non-chimeric) human light chains; (b) a complete, functional, immunoglobulin molecule comprising: (i) two identical chimeric heavy chains comprising a variable region as indicated, and a human constant region, and (ii) two identical all (i.e. non-chimeric) non-human light chains; (c) a monovalent antibody, i.e., a complete, functional immunoglobulin molecule comprising: (i) two identical chimeric heavy chains comprising a variable region as indicated, and a human constant region, and (ii) two different light chains, only one of which has the same specificity as the variable region of the heavy chains. The resulting antibody molecule binds only to one end thereof and is therefore incapable of divalent binding. As another illustration, immunoglobulin-related peptides provided by the present invention may be said to include the following: (a) a whole immunoglobulin molecule; (b) an scFv; (c) a monoclonal antibody; (d) a human antibody; (e) a chimeric antibody; (f) a humanized antibody; (g) a Fab fragment; (h) an Fab' fragment; (i) an $F(ab')_2$ fragment; (j) an Fv molecule; and (k) a disulfide-linked Fv molecule.

In one embodiment, the antibody used in the present invention is a polyclonal antibody. In one embodiment, the antibody used in of the present invention is an monoclonal antibody. In a further embodiment, the antibody used in of the present invention is a human monoclonal antibody. In another further embodiment, the antibody used in of the present invention is a humanized antibody. In another further embodiment, the antibody used in of the present invention is a chimeric antibody. In another further embodiment, the antibody used in of the present invention is a monoclonal antibody originating entirely from a mammalian species different from humans. In a further embodiment, the antibody used in of the present invention is a fully murine monoclonal antibody.

In one embodiment, the antibody used in the invention is glycosylated in a eukaryotic cell. In another embodiment, the antibody used in the invention further comprises a chelator linker for attaching a radioisotope. In a further embodiment, the antibody used in the invention is in a substantially isolated form.

A monoclonal antibody refers to a composition comprising a homogeneous antibody population having a uniform structure and specificity. Typically a monoclonal antibody is an antibody obtained from a population of substantially homogeneous antibodies, i.e., the individual antibodies comprising the population are identical except for possible naturally occurring mutations that may be present in minor amounts. Monoclonal antibodies are highly specific and each monoclonal antibody is typically directed against a single epitope, which is in contrast to polyclonal antibody preparations which typically include different antibodies directed against different epitopes. That an antibody is monoclonal is not to be construed as requiring production of the antibody by any particular method. For example, the monoclonal antibodies of the present invention may be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991).

Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Alternatively, the cloned antibody genes can be expressed in other expression systems, including prokaryotic cells, such as microorganisms, such as *E. coli*, for the production of single chain Fv antibodies, algi, as well as insect cells. Furthermore, the antibodies can be produced in transgenic non-human animals, such as in milk from sheep and rabbits or in eggs from hens, or in transgenic plants. See for instance Verma, R., et al., J. Immunol. Meth. 216, 165-181 (1998); Pollock, et al., J. Immunol. Meth. 231, 147-157 (1999); and Fischer, R., et al., Biol. Chem. 380, 825-839 (1999).

In one embodiment, human monoclonal antibodies directed against CD38 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice". A human monoclonal antibody generated in such mice may be abbreviated as HuMab.

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569, 825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424). In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.Splenocytes from these transgenic mice may be used to generate hybridomas that secrete human monoclonal antibodies according to well known techniques.

Human monoclonal or polyclonal antibodies used in the present invention, or antibodies used in the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

Further, human antibodies used in the present invention or antibodies used in the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hoogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized, for instance as described elsewhere herein.

Examples of how to make humanized antibodies may be found in for instance U.S. Pat. Nos. 6,054,297, 5,886,152 and U.S. Pat. No. 5,877,293. Also, the use of Ig cDNA for construction of chimeric immunoglobulin genes is known in the art (see for instance Liu et al., PNAS USA 84, 3439 (1987) and J. Immunol. 139, 3521 (1987

Anti-CD38 antibodies may be recovered from recombinant combinatorial antibody libraries, such as a scFv phage display library, which may be made with human $V_L$ and $V_H$ cDNAs prepared from mRNA derived from human lymphocytes. Methods for preparing and screening such libraries are known in the art. There are a number of commercially available kits for generating phage display libraries. There are also other methods and reagents that may be used in generating and screening antibody display libraries (see for instance U.S. Pat. No. 5,223,409, WO 92/18619, WO 91/17271, WO 92/20791, WO 92/15679, WO 93/01288, WO 92/01047, WO 92/09690, Fuchs et al., Bio/Technology 9,1370-1372 (1991), Hay et al., Hum. Antibod. Hybridomas 3, 81-85 (1992), Huse et al., Science 246,1275-1281 (1989), McCafferty et al., Nature 348, 552-554 (1990), Griffiths et al., EMBO J 12, 725-734 (1993), Hawkins et al., J. Mol. Biol. 226, 889-896 (1992), Clackson et al., Nature 352, 624-628 (1991), Gram et al., PNAS USA 89, 3576-3580 (1992), Garrad et al., Bio/Technology 9, 1373-1377 (1991), Hoogenboom et al., Nuc Acid Res 19, 4133-4137 (1991) and Barbas et al., PNAS USA 88, 7978-7982 (1991)). Suitable $V_L$ and $V_H$ nucleic acid sequences may be selected using any appropriate method. For example, $V_L$ and $V_H$ nucleic acids may be selected by employing the epitope imprinting methods described in WO 93/06213. Antibody libraries, such as scFv libraries may be prepared and screened using known and suitable methods (with human CD38-containing peptides as antigen(s)), such as those described in for instance WO92/01047, McCafferty et al., Nature 348, 552-554 (1990) and Griffiths et al., EMBO J 12, 725-734 (1993). Such antibody libraries are features of the present invention that may be used therapeutically to provide a more comprehensive immune response; as tools in screening methods for immunogenic peptides, small molecules, other anti-CD38 antibodies (e.g., by way of competition assays), and the like; and/or in diagnostic methods and compositions (e.g., an immunoassay chip comprising a panel of such antibodies optionally in association with other antibodies may be prepared by standard techniques). Once initial human $V_L$ and $V_H$ segments are selected, "mix and match" experiments, in which different pairs of the initially selected $V_L$ and $V_H$ segments are screened for CD38-containing peptide binding, may be performed to select desirable $V_L$/$V_H$ pair combinations. For example, reactivity of the peptides may be determined by ELISA or other suitable epitope analysis methods (see for instance Scott, J. K. and Smith, G. P. Science 249, 386-390 (1990), Cwirla et al., PNAS USA 87, 6378-6382 (1990), Felici et al., J. Mol. Biol. 222, 301-310 (1991) and Kuwabara et al., Nature Biotechnology 15, 74-78 (1997) for discussion of such techniques and principles). Antibodies may be selected by their affinity for antigen and/or by their kinetics of dissociation (off-rate) from antigen (see for instance Hawkins et al., J. Mol. Biol. 226, 889-896 (1992)).

High-affinity antibody peptides, such as human single-chain Fv (scFv) and Fab antibody fragments, may also be isolated from such libraries using a panning technique in which the antigen of interest is immobilized on a solid surface, such as microtiter plates or beads (see for instance Barbas and Burton, Trends. Biotechnol. 14, 230-234 (1996) and Aujame et al., Hum. Antibodies 8, 155-68 (1997). Phage display of large naïve libraries also makes it possible to isolate human antibodies directly without immunization (see for instance de Haard et al., J. Biol. Chem. 274(26), 18218-18230 (1999)).

Antibodies suitable for use in the present invention may be selected based on their ability to provide the ability of complement fixation, or not. There are a number of isotypes of antibodies that are capable of complement fixation and CDC, including, without limitation, the following: murine IgM, murine IgG2a, murine IgG2b, murine IgG3, human IgM, human IgG1, and human IgG3. Those isotypes that do not include, without limitation, human IgG2 and human IgG4. Isotype determination and other methods for modifying the complement fixation and CDC functional characteristics of antibodies are known in the art.

Anti-CD38 antibodies used in the present invention may be prepared by recombinant expression in any suitable type of cells or animals. Suitable methods for antibody production are known in the art and include those described in for instance Harlow et al., Antibodies: A Laboratory Manual, Cold Spring Harbor Laboratory Press, Cold Spring Harbor, N.Y., (1988), Harlow and Lane: Using Antibodies: A Laboratory Manual (Cold Spring Harbor Laboratory Press (1999)), U.S. Pat. No. 4,376,110 and Ausubel et al., eds., Current Protocols In Molecular Biology, Greene Publishing Assoc. and Wiley InterScience N.Y., (1987, 1992). Monoclonal antibodies may be made using the hybridoma method first described by Kohler et al., Nature 256, 495 (1975), or by other well-known, subsequently-developed methods (see, e.g., Goding, Monoclonal Antibodies: Principles and Practice, pp. 59-103 (Academic Press, 1986)). Hybridomas useful in the production of anti-CD38 antibodies of the present invention are also provided by the present invention. Such hybridomas may be formed by chemical fusion, electrical fusion, or any other suitable technique, with any suitable type of myeloma, heteromyeloma, phoblastoid cell, plasmacytoma or other equivalent thereof and any suitable type of antibody-expressing cell. Transformed immortalized B cells may also be used to efficiently produce antibodies of the present invention and are also provided by the present invention. Such cells may be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al., in Monoclonal Antibodies, ed. by Kennett R. H. et al., Plenum Press, N.Y. 1980, pp 19-33.).

Recombinant cells comprising exogenous nucleic acids encoding anti-CD38 antibodies may be prepared by any suitable technique (e.g., transfection/transformation with a naked DNA plasmid vector, viral vector, invasive bacterial cell vector or other whole cell vector, etc., comprising a antibody-encoding sequence (or sequences) delivered into the cell by calcium phosphate-precipitation facilitated transfection, receptor-mediated targeting and transfection, biolistic delivery, electroporation, dextran-mediated transfection, liposome-mediated transformation, protoplast fusion, direct microinjection, etc.). Methods of transforming/transfecting cells are well known in the art (see, e.g., Sambrook et al., Molecular Cloning: A Laboratory Manual, Cold Spring Harbor Laboratory Press (2d Edition, 1989 and 3rd Edition, 2001) and F. Ausubel et al., ed. Current Protocols in Molecular Biology, Greene Publishing and Wiley InterScience New York (1987). Such recombinant cells are a feature of the present invention.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding proteins, such as anti-CD38 antibodies), are introduced into mammalian host cells, proteins may be produced by culturing the host cells for a period of time sufficient to allow for expression of the protein in the host cells or by secretion of the protein into the culture medium in which the host cells are grown. Antibodies may be recovered from the culture medium using standard protein purification methods. Antibodies may also be recovered from host cell lysates when directly expressed without a secretory signal.

When recombinant expression vectors encoding anti-CD38 antibody genes are introduced into mammalian host cells, the antibodies are produced by culturing the host cells for a period of time sufficient to allow for expression of the antibody in the host cells or for secretion of the antibody into the culture medium in which the host cells are grown. The purification of antibodies from cell cultures, cell lysates, and animals (e.g., from the ascites fluid of a transgenic animal producing anti-CD38 antibodies) may be achieved by application of any number of suitable techniques known in the art including, e.g., immunoaffinity column purification; sulfate precipitation; chromatofocusing; preparative SDS-PAGE, and the like.

Human monoclonal antibodies of the present invention may also be produced by a variety of other techniques, including conventional monoclonal antibody methodology, e.g., the standard somatic cell hybridization technique of Kohler and Milstein, Nature 256, 495 (1975). Other techniques for producing monoclonal antibody may also be employed, e.g. phage display techniques using libraries of human antibody genes. In one embodiment, anti-CD38 antibodies of the present invention produced by use of hybridomas generated in a murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

To generate fully human monoclonal antibodies to CD38, transgenic or transchromosomal mice containing human immunoglobulin genes (e.g., HCo12, HCo7 or KM mice) may be immunized with an enriched preparation of CD38 antigen and/or cells expressing CD38, as described, for example, by Lonberg et al., (1994), supra, Fishwild et al., (1996), supra, and WO 98/24884. Alternatively, mice may be immunized with DNA encoding human CD38. The mice may be 6-16 weeks of age upon the first infusion. For example, an enriched preparation (5-50 µg) of the CD38 antigen may be used to immunize the HuMAb mice intraperitoneally. In the event that immunizations using a purified or enriched preparation of the CD38 antigen do not result in antibodies, mice may also be immunized with cells expressing CD38, e.g., a cell line, to promote immune responses.

Cumulative experience with various antigens has shown that the HuMAb transgenic mice respond best when initially immunized intraperitoneally (i.p.) or subcutaneously (s.c.) with CD38 expressing cells in complete Freund's adjuvant, followed by every other week i.p. immunizations (up to a total of 10) with CD38 expressing cells in PBS. The immune response may be monitored over the course of the immunization protocol with plasma samples being obtained by retroorbital bleeds. The plasma may be screened by FACS analysis, and mice with sufficient titers of anti-CD38 human immunoglobulin may be used for fusions. Mice may be boosted intravenously with CD38 expressing cells for Examples 4 and 3 days before sacrifice and removal of the spleen.

To generate hybridomas producing human monoclonal antibodies to human CD38, splenocytes and lymph node cells from immunized mice may be isolated and fused to an appropriate immortalized cell line, such as a mouse myeloma cell line. The resulting hybridomas may then be screened for the production of antigen-specific antibodies. For example, single cell suspensions of splenic lymphocytes from immunized mice may be fused to SP2/0 nonsecreting mouse myeloma cells (ATCC, CRL 1581) with 50% PEG (w/v). Cells may be plated at approximately 1×105 per well in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells may be cultured in medium in which the HAT is replaced with HT. Individual wells may then be screened by ELISA for human kappa-light chain containing antibodies and by FACS analysis using CD38 expressing cells for CD38 specificity. Once extensive hybridoma growth occurs, medium may be observed usually after 10-14 days. The antibody secreting hybridomas may be replated, screened again, and if still positive for human IgG, anti-CD38 monoclonal antibodies may be subcloned at least twice by limiting dilution. The stable subclones may then be cultured in vitro to generate antibody in tissue culture medium for characterization.

Human antibodies of the present invention may also be produced in a host cell transfectoma using, for example, a combination of recombinant DNA techniques and gene transfection methods as is well known in the art, see for instance Morrison, S., Science 229, 1202 (1985).

For example, to express the antibodies, or antibody fragments thereof, DNAs encoding partial or full-length light and heavy chains, may be obtained by standard molecular biology techniques (for instance PCR amplification, site directed mutagenesis) and may be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene may be inserted into separate vectors or, more typically, both genes are inserted into the same expression vector. The antibody genes may be inserted into the expression vector by standard methods (e.g., ligation of complementary restriction sites on the antibody gene fragment and vector, or blunt end ligation if no restriction sites are present). The light and heavy chain variable regions of the antibodies described herein may be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector may encode a signal peptide that facilitates secretion of the antibody chain from a host cell. The antibody chain gene may be cloned into the vector such that the signal peptide is linked in-frame to the amino terminus of the antibody chain gene. The signal peptide may be an immunoglobulin signal peptide or a heterologous signal peptide (i.e., a signal peptide from a non-immunoglobulin protein).

In addition to the antibody chain genes, the recombinant expression vectors carry regulatory sequences that allows and control the expression of the antibody chain genes in a host cell. Furthermore, the recombinant expression vectors may carry additional sequences, such as sequences that regulate replication of the vector in host cells (e.g., origins of replication) and selectable marker genes. The selectable marker gene facilitates selection of host cells into which the vector has been introduced (see for instance U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The host cells may be prokaryotic or eukaryotic, such as mammalian, host cells. For instance antigen binding fragments may be expressed in prokaryotic host cells and full-length antibodies may be expressed in eukaryotic host cells.

In one embodiment the antibodies are expressed in eukaryotic cells, such as mammalian host cells. Examples of mammalian host cells for expressing the recombinant antibodies of the present invention include CHO cells (including dhfr-CHO cells, described in Urlaub and Chasin, PNAS USA 77, 4216-4220 (1980), used with a DHFR selectable marker, for instance as described in R. J. Kaufman and P. A. Sharp, Mol. Biol. 159, 601-621 (1982)), NS/0 myeloma cells, COS cells, HEK293 cells and SP2.0 cells. In particular for use with NS/0 myeloma cells, another example of a expression system is the GS (glutamine synthetase) gene expression system disclosed in WO87/04462, WO89/01036 and EP338 841.

The antibody genes may be expressed in other expression systems, including prokaryotic cells, such as microorganisms, e.g. *E. coli* for the production of scFv antibodies, algi, as well as insect cells. Furthermore, the antibodies may be produced in transgenic non-human animals, such as in milk from sheep and rabbits or eggs from hens, or in transgenic plants. See for instance Verma, R. et al., J. Immunol. Meth. 216, 165-181 (1998), Pollock et al., J. Immunol. Meth. 231, 147-157 (1999) and Fischer, R. et al., Biol. Chem. 380, 825-839 (1999).

Bispecific and Multispecific Antibodies

In one embodiment of the present invention, the antibody used may be derivatized or linked to another functional molecule, for instance another peptide or protein (such as a Fab' fragment) to generate a bispecific or multispecific molecule which binds to multiple binding sites or target epitopes. For example, an antibody used in the present invention may be functionally linked (for instance by chemical coupling, genetic fusion, noncovalent association or otherwise) to one or more other binding molecules, such as another antibody, peptide or binding mimetic.

Accordingly, the present invention includes the use of bispecific and multispecific molecules comprising at least one first binding specificity for CD38 and a second binding specificity for a second target epitope. In one embodiment of the present invention, the second target epitope is an Fc receptor, e.g., human FcγRI (CD64) or a human Fcα receptor (CD89), or a T cell receptor, e.g., CD3. In one embodiment, the present invention provides bispecific and multispecific molecules capable of binding both to FcγR, FcαR or FcεR expressing effector cells (e.g., monocytes, macrophages or polymorphonuclear cells (PMNs)), and to target cells expressing CD38. These bispecific and multispecific molecules target CD38 expressing cells to effector cell and trigger Fc receptor-mediated effector cell activities, such as phagocytosis of CD38 expressing cells, antibody dependent cellular cytotoxicity (ADCC), cytokine release, or generation of superoxide anion.

In one embodiment, the bispecific and multispecific molecules used in the present invention comprise as a binding specificity at least one further antibody, including, e.g., an Fab, Fab', F(ab')2, Fv, or a scFv. The further antibody may also be a light chain or heavy chain dimer, or any minimal fragment thereof such as a Fv or a single chain construct as described in Ladner et al., in U.S. Pat. No. 4,946,778. The antibody may also be a binding-domain immunoglobulin fusion protein as disclosed in US 2003/0118592 and US 2003/0133939.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fc* receptor classes: FcγRI (CD64), FcγRII (CD32), and FcγRIII (CD16). In one embodiment, the Fcγ receptor is a human high affinity FcγRI. The production and characterization of these monoclonal antibodies are described by Fanger et al., in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in the present invention are mAb 22, mAb 32, mAb 44, mAb 62 and mAb 197. In other embodiments, the anti-Fcγ receptor antibody is a humanized form of mAb 22 (H22). The production and characterization of the H22 antibody is described in Graziano, R. F. et al., J. Immunol. 155(10), 4996-5002 (1995) and WO 94/10332. The H22 antibody producing cell line was deposited at the American Type Culture Collection on Nov. 4, 1992 under the designation HA022CL1 and has the accession No. CRL 11177.

In one embodiment, the binding specificity for an Fc receptor is provided by an antibody that binds to a human IgA receptor, e.g., an Fcα receptor (FcαI (CD89)), the binding of which in one embodiment is not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al., Critical Reviews in Immunology 16, 423-440 (1996)). Four FcαRI-specific monoclonal antibodies, identified as A3, A59, A62 and A77, which bind FcαRI outside the IgA ligand binding domain, have been described (Monteiro, R. C. et al., J. Immunol. 148, 1764 (1992)).

FcαRI, FcγRI, FcγRII and FcγRIII, especially FcγRII and FcγRIII, are examples of trigger receptors for use in the present invention because they (1) are expressed primarily on immune effector cells, e.g., monocytes, PMNs, macrophages and dendritic cells; (2) are expressed at high levels (for instance 5,000-100,000 per cell); (3) are mediators of cytotoxic activities (for instance ADCC, phagocytosis); and (4) mediate enhanced antigen presentation of antigens, including self-antigens, targeted to them.

Exemplary bispecific antibody molecules comprise (i) two antibodies one with a specificity to CD38 and another to a second target that are conjugated together, (ii) a single antibody that has one chain specific to CD38 and a second chain specific to a second molecule, and (iii) a single chain antibody that has specificity to CD38 and a second molecule. Typically, the second target/second molecule is a molecule other than CD38. In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, C-myc, Mart1, MelanA, MUM-1, MUM-2, MUM-3, HLA-B7, and Ep-CAM. In one embodiment, the second molecule is a cancer-associated integrin, such as α5β3 integrin. In one embodiment, the second molecule is an angiogenic factor or other cancer-associated growth factor, such as a vascular endothelial growth factor (VEGF), a fibroblast growth factor (FGF), epidermal growth factor (EGF), epidermal growth factor receptor (EGFR), angiogenin, and receptors thereof, particularly receptors associated with cancer progression (for instance one of the HER1-HER4 receptors). Other cancer progression-associated proteins discussed herein may also be suitable second molecules. In one embodiment, the second molecule is a molecule expressed on the surface of multiple myeloma cells such as CD138.

In one embodiment, a bispecific antibody used in the present invention is a diabody.

Bispecific and multispecific antibodies used in the present invention may be made using chemical techniques (see for instance D. M. Kranz et al., PNAS USA 78, 5807 (1981)), "polydoma" techniques (See U.S. Pat. No. 4,474,893) or recombinant DNA techniques.

Conjugates

In one embodiment, the present invention uses a CD38 antibody conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates useful for the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, actinomycin D, 1-dehydro-testosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, calicheamicin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, and enomycin toxins. Therapeutic agents, which may be administered in combination with an antibody as described elsewhere herein, may also be candidates for therapeutic moieties useful for conjugation to an antibody used in the present invention. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ, or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors and apoptoic inducing protein isolated from mitochondria.

Conjugates of antibodies, and such cytotoxic moieties may be made using a variety of bifunctional protein coupling agents. Examples of such reagents include SPDP, IT, bifunctional derivatives of imidoesters such a dimethyl adipimidate HCl, active esters such as disuccinimidyl suberate, aldehydes such as glutaraldehyde, bis-azido compounds such as bis(p-azidobenzoyl)hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene and anti-mitotic agents (e.g., vincristine, vinblastine, docetaxel, paclitaxel and vinorelbin).

In one embodiment, the present invention uses an anti-CD38 antibody that is conjugated to an immunomodulator, such as an immunomodulating cytokine, stem cell growth factor, lymphotoxin (such as a TNF such as TNFα), or a hematopoietic factor. Examples of such molecules that may be useful as conjugates include IL-1, IL-2, IL-3, IL-6, IL-10, IL-12, IL-18, and IL-21, colony stimulating factors (such as granulocyte-colony stimulating factor (G-CSF) and granulocyte macrophage-colony stimulating factor (GM-CSF)), interferons (such as IFNα, IFNβ, and IFNγ) the stem cell growth factor designated "S1 factor," erythropoietin, and thrombopoietin, active fragments thereof, derivatives thereof, variants thereof, or a combination of any thereof.

Techniques for conjugating such therapeutic moieties to antibodies, are well known, see for instance Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985), Hellstrom et al., "Antibodies For Drug Delivery", in Controlled Drug Delivery (2nd Ed.), Robinson et al., (eds.), pp. 623-53 (Marcel Dekker, Inc. 1987), Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985), "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985) and Thorpe et al., "The Preparation And Cytotoxic Properties Of Antibody-Toxin Conjugates", Immunol. Rev. 62, 119-58 (1982).

Additionally useful conjugate substituents include anti-cancer retinoids. Taxane conjugates (see for instance Jaime et al., Anticancer Res. 21(2A), 1119-28 (2001), cisplatin conjugates, thapsigargin conjugates, linoleic acid conjugates, calicheamicin conjugates (see for instance Damle et al., Curr Opin Pharmacol. 3(4), 386-90 (2003), doxorubicin conjugates, geldanamycin conjugates, and the like, also may be useful in promoting the treatment of cancer (see, generally, Trail et al., Cancer Immunol Immunother. 52(5), 328-37 (2003)).

Formulation and Mode-of-administration

The agents used in the present invention may be formulated as a pharmaceutical composition with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen compound used in the present invention and the chosen mode of administration. Suitability for carriers and other components of pharmaceutical compositions is determined based on the lack of significant negative impact on the desired biological properties of the chosen compound or pharmaceutical composition (e.g., less than a substantial impact (10% or less relative inhibition, 5% or less relative inhibition, etc.) on antigen binding.

A pharmaceutical composition used in the present invention may also include diluents, fillers, salts, buffers, detergents (e. g., a nonionic detergent, such as Tween-80), stabilizers, stabilizers (e. g., sugars or protein-free amino acids), preservatives, tissue fixatives, solubilizers, and/or other materials suitable for inclusion in a pharmaceutical composition.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and can be selected by those of ordinary skill in the art.

The compounds used in the present invention may be administered via any suitable route, such as an oral, nasal, inhalable, topical (including buccal, transdermal and sublingual), rectal, vaginal and/or parenteral route In one embodiment, one or more of the compounds used in the present invention is administered orally, for example, with an inert diluent or an assimilable edible carrier. The active ingredient may be enclosed in a hard or soft shell gelatin capsule, compressed into tablets, or incorporated directly into the subject's diet. Pharmaceutical compositions which are suitable for oral administration include ingestible tablets, buccal tablets, troches, capsules, elixirs, suspensions, syrups, wafers, and the like containing such carriers as are known in the art to be appropriate. To allow oral administration, it may be necessary to coat the compound with, or co-administer the compound with, a material to prevent its inactivation.

In one embodiment, one or more of the compounds used in the present invention are administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment, the compound is administered by intravenous or subcutaneous injection or infusion.

In one embodiment the compounds used in the present invention are administered in crystalline form by subcutaneous injection, cf. Yang et al., PNAS USA 100(12), 6934-6939 (2003).

Pharmaceutical compositions used in the present invention may be formulated for particular routes of administration, such as oral, nasal, topical (including buccal, transdermal and sublingual), rectal, vaginal and/or parenteral administration. The pharmaceutical compositions may conveniently be presented in unit dosage form and may be prepared by any methods known in the art of pharmacy. The amount of active ingredient which may be combined with a carrier material to produce a single dosage form will vary depending upon the subject being treated, and the particular mode of administration. The amount of active ingredient which may be combined with a carrier material to produce a single dosage form will generally be that amount of the composition which produces a therapeutic effect. Generally, out of one hundred per cent, this amount will range from about 0.01% to about 99% of active ingredient, such as from about 0.1% to about 70%, for instance from about 1% to about 30%.

Regardless of the route of administration selected, the compounds used in the present invention, which may be used in the form of a pharmaceutically acceptable salt or in a suitable hydrated form, and/or the pharmaceutical compositions are formulated into pharmaceutically acceptable dosage forms by conventional methods known to those of skill in the art. A "pharmaceutically acceptable salt" refers to a salt that retains the desired biological activity of the parent compound and does not impart any undesired toxicological effects (see for instance Berge, S. M. et al., J. Pharm. Sci. 66, 1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound used in the present invention.

Examples of suitable aqueous and nonaqueous carriers which may be employed in the pharmaceutical compositions include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions is contemplated.

Proper fluidity may be maintained, for example, by the use of coating materials, such as lecithin, by the maintenance of the required particle size in the case of dispersions, and by the use of surfactants.

Pharmaceutical compositions comprises agents used in the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions may also comprise isotonicity agents, such as sugars, polyalcohols such as mannitol, sorbitol, glycerol or sodium chloride in the compositions Pharmaceutically acceptable diluents include saline and aqueous buffer solutions.

The pharmaceutical compositions used in the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. Compounds of the present invention may for instance be admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. Other examples of adjuvants are QS21, GM-CSF, SRL-172, histamine dihydrochloride, thymocartin, Tio-TEPA, monophosphoryl-lipid A/micobacteria compositions, alum, incomplete Freund's adjuvant, montanide ISA, ribi adjuvant system, TiterMax adjuvant, syntex adjuvant formulations, immune-stimulating complexes (ISCOMs), gerbu adjuvant, CpG oligodeoxynucleotides, lipopolysaccharide, and polyinosinic:polycytidylic acid.

Prevention of presence of microorganisms may be ensured both by sterilization procedures and by the inclusion of various antibacterial and antifungal agents, for example, paraben, chlorobutanol, phenol, sorbic acid, and the like. In addition, prolonged absorption of the injectable pharmaceutical form may be brought about by the inclusion of agents which delay absorption such as aluminum monostearate and gelatin.

Pharmaceutical compositions comprising a compound of the present invention may also include a suitable salt therefore. Any suitable salt, such as an alkaline earth metal salt in any suitable form (e.g., a buffer salt), may be used in the stabilization of the compound used in the present invention. Suitable salts typically include sodium chloride, sodium succinate, sodium sulfate, potassium chloride, magnesium chloride, magnesium sulfate, and calcium chloride. In one embodiment, an aluminum salt is used to stabilize a compound used in the present invention in a pharmaceutical composition, which aluminum salt also may serve as an adjuvant when such a composition is administered to a patient.

The compounds used in the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

To administer compositions by certain routes of administration, it may be necessary to coat the compound with, or co-administer the compound with, a material to prevent its inactivation. For example, the compound used in the method of the invention may be administered to a subject in an appropriate carrier, for example, liposomes, or a diluent. Liposomes include water-in-oil-in-water CGF emulsions as well as conventional liposomes (Strejan et al., J. Neuroimmunol. 7, 27 (1984)).

Depending on the route of administration, the active compound may be coated in a material to protect the compound from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strejan et al., J. Neuroimmunol. 7, 27 (1984)).

In one embodiment of the present invention, the compounds of the present invention are formulated in liposomes. In a further embodiment, the liposomes include a targeting moiety. In a further embodiment, the compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

In one embodiment, the compounds used in the present invention may be formulated to prevent or reduce their transport across the placenta. This may be done by methods known in the art, e.g., by PEGylation of the compounds or by use of F(ab')$_2$ fragments. Further references can be made to Cunningham-Rundles C et al., J Immunol Methods. 152, 177-190 (1992) and to Landor M., Ann Allergy Asthma Immunol 74, 279-283 (1995).

Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

In one embodiment of the methods of the invention, said at least one non-corticosteroid chemotherapeutic agent comprises melphalan, wherein melphalan is administered intravenously or perorally.

In another embodiment of the methods of the invention, said at least one non-corticosteroid chemotherapeutic agent comprises a glutamic acid derivative, such as thalidomide (Thalomid®) or a thalidomide analog, e.g. CC-5013 (lenalidomide, Revlimid™) or CC4047 (Actimid™), wherein said glutamic acid derivative is administered perorally.

In another embodiment of the methods of the invention, said at least one non-corticosteroid chemotherapeutic agent comprises a proteasome inhibitor, such as bortezomib (Velcade®), wherein bortezomib is administered intravenously.

In another embodiment of the methods of the invention, said at least one non-corticosteroid chemotherapeutic agent comprises a vinca alkaloid, such as vincristine, wherein vincristine is administered intravenously.

In another embodiment of the methods of the invention, said at least one non-corticosteroid chemotherapeutic agent comprises an anthracycline, such as doxorubicin, wherein doxorubicin is administered intravenously In another embodiment of the methods of the invention, said at least one corticosteroid comprises prednisone, wherein said prednisone is administered perorally.

In another embodiment of the methods of the invention, said at least one corticosteroid comprises prednisone, wherein said prednisone is administered perorally.

Patients and Diseases to be Treated

Individuals that may be treated with the combination therapy of the invention may for instance include human patients having disorders that may be corrected or ameliorated by inhibiting CD38 function, such as enzymatic activity, signal transduction, induction of cytokine expression, induction of proliferation or differentiation, and/or induction of lysis and/or eliminating/reducing the number of CD38 expressing cells.

For example, the anti-CD38 antibodies may be used to elicit in vivo or in vitro one or more of the following biological activities: inhibition CD38 function (such as enzymatic activity, signal transduction, induction of cytokine expression, induction of proliferation or differentiation, and/or induction of lysis), killing a cell expressing CD38, mediating phagocytosis or ADCC of a cell expressing CD38 in the presence of human effector cells, and by mediating CDC of a cell expressing CD38 in the presence of complement. or by killing CD38 expressing cells by apoptosis.

In one embodiment, immunoconjugates described herein may be used to target compounds (e.g., therapeutic agents, labels, cytotoxins, immunosuppressants, etc.) to cells which have CD38 bound to their surface by using such target compounds as the therapeutic moieties in immunoconjugates of the present invention.

In one embodiment, the present invention provides methods for killing cells which have CD38 bound to their surface by administering immunoconjugates of the present invention.

The present invention provides methods for treating a disorder involving cells expressing CD38 in a subject, which method comprises administration of a therapeutically effective amount of i) a non-agonistic antibody which binds to CD38, ii) at least one corticosteroid, and iii) at least one non-corticosteroid chemotherapeutic agent, to a subject in need thereof. Anti-CD38 antibodies are used to inhibit CD38 induced activities associated with certain disorders or to eliminate or reduce the number of cells expressing CD38.

In one embodiment of the present invention, the disorder involving cells expressing CD38 is a tumorigenic disorder, such as a disorder characterized by the presence of tumor cells expressing CD38 including, for example, B cell lymphoma, plasma cell malignancies, T/NK cell lymphoma and myeloid malignancies.

Examples of such tumorigenic diseases include B cell lymphoma/leukemias including precursor B cell lymphoblastic leukemia/lymphoma and B cell non-Hodgkin's lymphomas; acute promyelocytic leukemia acute lymphoblastic leukemia and mature B cell neoplasms, such as B cell chronic lymhocytic leukemia(CLL)/small lymphocytic lymphoma (SLL), B cell acute lymphocytic leukemia, B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, plasma cell leukemia, post-transplant lymphoproliferative disorder, Waldenström's macroglobulinemia, plasma cell leukemias and anaplastic large-cell lymphoma (ALCL).

In one embodiment, the disorder involving cells expressing CD38 is multiple myeloma.

Examples of B cell non-Hodgkin's lymphomas are lymphomatoid granulomatosis, primary effusion lymphoma, intravascular large B cell lymphoma, mediastinal large B cell lymphoma, heavy chain diseases (including $\gamma$, $\mu$, and $\alpha$ disease), lymphomas induced by therapy with immunosuppressive agents, such as cyclosporine-induced lymphoma, and methotrexate-induced lymphoma.

In one embodiment of the present invention, the disorder involving cells expressing CD38 may be Hodgkin's lymphoma.

Examples of a disorder involving cells expressing CD38 may be a malignancy derived from T and NK cells including: mature T cell and NK cell neoplasms including T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, subcutaneous panniculitis-like T cell lymphoma, blastic NK cell lymphoma, Mycosis Fungoides/Sézary Syndrome, primary cutaneous CD30 positive T cell lymphoproliferative disorders (primary cutaneous anaplastic large cell lymphoma C-ALCL, lymphomatoid papulosis, borderline lesions), angioimmunoblastic T cell lymphoma, peripheral T cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

Dosages and Treatment Regimens

Treatment according to the present invention includes a "therapeutically effective amount" of the medicaments used. A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects. In the context of the present combination therapy, a therapeutic amount includes amounts that are therapeutically effective only in combination with the other compounds, e.g. amounts that would be too low to be effective in monotherapy.

A "therapeutically effective amount" for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-CD38 antibodies used in the present invention depend on the disease or condition to be treated and may be determined by the persons skilled in the art. An exemplary, non-limiting range for a therapeutically effective amount of an anti-CD38 antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, he antibody is administered in a dose of 1 mg/kg or more, such as a dose of from 1 to 20 mg/kg, e.g. a dose of from 5 to 20 mg/kg, e.g. a dose of 8 mg/kg.

A physician or veterinarian having ordinary skill in the art may readily determine and prescribe the effective amount of the pharmaceutical composition required. For example, the physician or veterinarian could start doses of the medicament employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

In one embodiment, the anti-CD38 antibody is administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the anti-CD38 antibody is administered by slow continuous infusion over a long period, such as more than 24 hours, in order to reduce toxic side effects.

In one embodiment the anti-CD38 antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-CD38 antibody.

In a further embodiment, the anti-CD38 antibody is administered once weekly for 2 to 12 weeks, such as for 3 to 10 weeks, such as for 4 to 8 weeks.

In one embodiment, the anti-CD38 antibody is administered by maintenance therapy, such as, e.g., once a week for a period of 6 months or more.

In one embodiment, the anti-CD38 antibody is administered by a regimen including one infusion of an anti-CD38 antibody followed by an infusion of an anti-CD38 antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In one embodiment of the methods of the invention, said at least one non-corticosteroid chemotherapeutic agent comprises melphalan, and said at least one corticosteroid comprises prednisone. Typically, melphalan is dosed intravenously (IV), but it can be used perorally (PO), e.g. in the range of 0.2-0.25 mg/kg per day or e.g. 7-9 mg/m2). Prednisone may e.g. be dosed at 2 mg/kg for 4 days every 4-6 weeks (Alexanian et al., J Am Med Assoc 1969; 208:1680). In other embodiments, melphalan can be used in high dose regimen in single doses up to 140 mg/m2 (IV) or intermediate doses in range of 25 to 75 mg/m2 (IV), one example is 40 mg/d administered days 1-4, 9-12 and 17-20 every 5 week cycle (Tsakanikas et al., Oncology 1991; 48:369, Richardson P G Am J Oncol 2005; 4:737).

In another embodiment of the methods of the invention, said at least one non-corticosteroid chemotherapeutic agent comprises thalidomide (Thalomid®), and said at least one corticosteroid comprises dexamethasone. Thalidomide can e.g. be used a in dose of 200 mg/d (PO), or e.g. in a range from 50 to 400 mg/d together with e.g. a dose of dexamethasone of 40 mg/d either administered daily or administered sequentially, e.g. day 1-4, 9-12 and 17-20 of each 28-day cycle. (Rajkumar S V J Clin Oncol 2006; 24:431).

In another embodiment of the methods of the invention, said at least one non-corticosteroid chemotherapeutic agent comprises lenalidomide, and said at least one corticosteroid comprises dexamethasone. Lenalidomide can e.g. be administered in doses of 25 mg/d administered daily (PO) and dexamethasone e.g. in a range of 40 mg/d administered (PO) e.g. on day 1-4, 9-12 and 17-20 of 28-day cycle optionally later only on day 1-4 of each cycle (Rajkumar S V, ASH 2004).

In another embodiment of the methods of the invention, said at least one non-corticosteroid chemotherapeutic agent comprises bortezomib (Velcade®). Bortezomib can e.g. be used combination with dexamethasone. This combination can be used both in induction and maintenance setting. One example is bortezomib 1.3 mg/m2 on days 1,4,8 and 11 every 21 day cycle (induction phase, normally up to 8 cycles) followed by days 1,8,11,15 and 22 every 5 week cycle for maintenance (Richardson P G N Engl J Med 2005; 352:2487).

In another embodiment of the methods of the invention, said at least one non-corticosteroid chemotherapeutic agent comprises vincristine and doxorubicin, and said at least one corticosteroid comprises dexamethasone. Vincristine may e.g. be administered by continuous IV infusion, 0.4 mg per day (days 1-4 on every 4 week cycle) and doxorubicin e.g. in a dose of 9 mg/m2/d continuous IV infusions on days 1-4 in every 4 week cycle. Dexametasone can e.g. be dosed 40 mg on days 1-4, 9-12 and 17-21 every 4 week cycle. Alternatively pegylated liposomal doxorubicin (e.g. in a dose of 40 mg/m2 on day 1 in a week cycle) can be used (Rifkin Cancer 2006; 106:848).

Further Combinations

The combination therapy of the invention may be further combined with other medicaments, i.e., combined with further therapeutic agents relevant for the disease or condition to be treated. Such administration may be simultaneous, separate or sequential. For simultaneous administration the agents may be administered as one compositions or as separate compositions, as appropriate.

Accordingly, the present invention provides methods for treating a disorder involving cells expressing CD38 as described above, which methods comprise the triple therapy of the present invention combined with one or more additional therapeutic agents as described below.

In one embodiment, the combination therapy of the invention further includes administration of at least one chemotherapeutic agent, at least one anti-inflammatory agent, or at least one immunosuppressive and/or immunomodulatory agent.

In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents.

In one embodiment, such a chemotherapeutic agent may be selected from an antibiotic, such as dactinomycin (formerly actinomycin), bleomycin, daunorubicin (formerly daunomycin), idarubicin, mithramycin, mitomycin, mitoxantrone, plicamycin, anthramycin (AMC) and similar agents.

In one embodiment, such a chemotherapeutic agent may be selected from an anti-mitotic agent, such as taxanes, for instance docetaxel, and paclitaxel.

In one embodiment, such a chemotherapeutic agent may be selected from a topoisomerase inhibitor, such as topotecan.

In one embodiment, such a chemotherapeutic agent may be selected from a growth factor inhibitor, such as an inhibitor of ErbB1 (EGFR) (such as gefitinib (Iressa®), cetuximab (Erbitux®), erlotinib (Tarceva®), 2F8 (disclosed in WO 2002/100348) and similar agents), an inhibitor of ErbB2 (Her2/neu) (such as trastuzumab (Herceptin®) and similar agents) and similar agents. In one embodiment, such a growth factor inhibitor may be a farnesyl transferase inhibitor, such as SCH-66336 and R115777. In one, embodiment, such a growth factor inhibitor may be a vascular endothelial growth factor (VEGF) inhibitor, such as bevacizumab (Avastin®).

In one embodiment, such a chemotherapeutic agent may be a tyrosine kinase inhibitor, such as imatinib (Glivec, Gleevec STI571), lapatinib, PTK787/ZK222584 and similar agents.

In one embodiment, such a chemotherapeutic agent may be a histone deacetylase inhibitor. Examples of such histone deacetylase inhibitors include hydroxamic acid-based hybrid polar compounds, such as SAHA (suberoylanilide hydroxamic acid).

In one embodiment, such a chemotherapeutic agent may be a P38a MAP kinase inhibitor, such as SCIO-469.

In a further embodiment, the combination therapy of the invention further includes administration of at least one inhibitor of angiogenesis, neovascularization, and/or other vascularization to a subject in need thereof Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In a further embodiment, the combination therapy of the invention further includes administration of an anti-cancer immunogen, such as a cancer antigen/tumor-associated antigen (e.g., epithelial cell adhesion molecule (EpCAM/TAC-STD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J Immunol. 137(5), 1743-9 (1986), Pohl et al., Int J Cancer. 50(6), 958-67 (1992), Bohlen et al., Cytokines Mol Ther. 2(4), 231-8 (1996) and Maruyama, J Immunol Methods. 264(1-2), 121-33 (2002)). Such anti-idiotypic Abs may optionally be conjugated to a carrier, which may be a synthetic (typically inert) molecule carrier, a protein (for instance keyhole limpet hemocyanin (KLH) (see for instance Ochi et al., Eur J Immunol. 17(11), 1645-8 (1987)), or a cell (for instance a red blood cell—see for instance Wi et al., J Immunol Methods. 122(2), 227-34 (1989)).

In a further embodiment, the combination therapy of the invention further includes administration of a bisphosphonate. Examples of potentially suitable biphosphonates are pamidronate (Aredia®), zoledronic acid (Zometa®), clodronate (Bonefos®), risendronate (Actonel®), ibandronate (Boniva®), etidronate (Didronel®), alendronate (Fosamax®), tiludronate (Skelid®), incadronate (Yamanouchi Pharmaceutical) and minodronate (YM529, Yamanouchi).

In a further embodiment, the combination therapy of the invention further includes administration of a colony stimulating factor. Examples of suitable colony stimulating factors are granulocyte-colony stimulating factors (G-CSF), such as filgrastim (Neupogen®) and pegfilgrastim (Neulasta®), and granulocyte macrophage-colony stimulating factors (GM-CSF) such as sargramostim (Leukine®).

In a further embodiment, the combination therapy of the invention further includes administration of an erythropoietic agent. Examples of suitable erythropoietic agents are erythropoietin (EPO), such as epoetin alfa (for instance Procrit®, Epogen®, and Eprex®) and epoetin beta (for instance Neo-Recormon®) and erythropoiesis-stimulating proteins (for instance Aranesp®).

In a further embodiment, the combination therapy of the invention further includes administration of an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C—C chemokine families. Suitable cytokines include cytokine derivatives, cytokine variants, cytokine fragments, and cytokine fusion proteins.

In a further embodiment, the combination therapy of the invention further includes administration of an agent that modulates, e.g., enhances or inhibits, the expression or activity of Fcα or Fcγ receptors. Examples of agents suitable for this use include interleukin-1 (IL-1), interleukin-2 (IL-2), interleukin-6 (IL-6), granulocyte colony-stimulating factor (G-CSF), such as filgrastim (Neupogen®) and pegfilgrastim (Neulasta®), and granulocyte macrophage-colony stimulating factors (GM-CSF) such as sargramostim (Leukine®), interferon-γ (IFN-γ), and tumor necrosis factor (TNF).

In a further embodiment, the combination therapy of the invention further includes administration of a cell cycle control/apoptosis regulator (or "regulating agent"). A cell cycle control/apoptosis regulator may include molecules (i) that target and modulate cell cycle control/apoptosis regulators such as cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No 6,713,055). Non-limiting examples of molecules that interfere with apoptotic pathways include TNF-related apoptdsis-inducing ligand (TRAIL)/apoptosis-2 ligand (Apo-2L), agents inducing NF-κB blockade leading to inhibition of IL-6 production, antibodies that activate TRAIL receptors, IFNs, anti-sense Bcl-2, and $As_2O_3$ (arsenic trioxide, Trisenox®).

In a further embodiment, the combination therapy of the invention further includes administration of a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/-sandostatin) and similar agents.

In a further embodiment, the combination therapy of the invention further includes administration of an anti-anergic agent (for instance small molecule compounds, proteins, glycoproteins, or antibodies that break tolerance to tumor and cancer antigens). Examples of such compounds are molecules that block the activity of CTLA-4, such as MDX-010 (Phan et al., PNAS USA 100, 8372 (2003)).

In a further embodiment, the combination therapy of the invention further includes administration of a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In a further embodiment, the combination therapy of the invention further includes administration of an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2h.

In a further embodiment, the combination therapy of the invention further includes administration of an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J Oncol. 4(1), 97-105 (2004), Collis et al., Int J Radiat Oncol Biol Phys. 57(2 Suppl), S144 (2003), Yang et al., Oncogene. 22(36), 5694-701 (2003) and Zhang et al., Biochem Biophys Res Commun. 303(4), 1169-78 (2003)).

In a further embodiment, the combination therapy of the invention further includes administration of a virus, viral proteins, and the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions (see for instance Shah et al., J Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J Oncol. 24(4), 919-23 (2004) and Zwiebel et al., Semin Oncol. 28(4), 336-43 (2001).

In a further embodiment, the combination therapy of the invention may further involve "whole cell" and "adoptive" immunotherapy methods. For instance, such methods may comprise infusion or re-infusion of immune system cells (for instance tumor-infiltrating lymphocytes (TILs), such as $CD4^+$ and/or $CD8^+$ T cells (for instance T cells expanded with tumor-specific antigens and/or genetic enhancements), antibody-expressing B cells or other antibody producing/presenting cells, dendritic cells (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In a further embodiment, the combination therapy of the invention further includes the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof).

In a further embodiment, the combination therapy of the invention further includes administration of complement. Accordingly, the use of compositions comprising anti-CD38 antibodies with serum or complement is also within the scope of the present invention. In these compositions the complement is located in close proximity to the anti-CD38 antibody, for instance by conjugation or may be suited for simultaneous administration. Alternatively, the anti-CD38 antibodies and the complement or serum may be administered separately.

In a further embodiment, the combination therapy of the invention further includes administration of differentiation inducing agents, retinoic acid and retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

In a further embodiment, the combination therapy of the invention further includes administration of a cathepsin B, modulators of cathepsin D dehydrogenase activity, glutathione-S-transferase (such as glutacylcysteine synthetase and lactate dehydrogenase), or similar agents.

In a further embodiment, the combination therapy of the invention further includes administration of estramustine or epirubicin.

In a further embodiment, the combination therapy of the invention further includes administration of a HSP90 inhibitor like 17-allyl amino geld-anamycin, antibodies directed against a tumor antigen such as PSA, CA125, KSA, etc., integrins like integrin β1, inhibitors of VCAM or similar agents In a further embodiment, the combination therapy of the invention further includes administration of calcineurin-inhibitors (such as valspodar, PSC 833 and other MDR-1 or p-glycoprotein inhibitors), TOR-inhibitors (such as sirolimus, everolimus and rapamycin). and inhibitors of "lymphocyte homing" mechanisms (such as FTY720), and agents with effects on cell signaling such as adhesion molecule inhibitors (for instance anti-LFA, etc.).

In a further embodiment, the combination therapy of the invention further includes radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT), brachytherapy (BT) or skeletal targeted radiotherapy). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the combination therapy of the invention further includes autologous peripheral stem cell or bone marrow transplantation.

In a further embodiment, the combination therapy of the invention further includes orthopedic intervention.

Orthopedic interventions may be used in the treatment of a disorder involving cells expressing CD38, such as multiple myeloma, to help control pain or retain function or mobility. Such interventions may include physical therapy, splinting of bones to prevent or treat fractures, or surgical procedures (minor or major) to repair fractures.

In a further embodiment, the combination therapy of the invention further includes delivery of one or more agents that promote access of the CD38 antibody or combination composition to the interior of a tumor. Such methods may for example be performed in association with the delivery of a relaxin, which is capable of relaxing a tumor (see for instance U.S. Pat. No. 6,719,977). In one embodiment, the anti-CD38 antibody used in the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., J Cancer Res Clin Oncol. 129 (12), 669-75 (2003), Pooga et al., FASEB J. 12(1), 67-77 (1998) and Tseng et al., Mol Pharmacol. 62(4), 864-72 (2002).

In a further embodiment, the combination therapy of the invention further includes administration of at least one anti-inflammatory agent.

In one embodiment such an anti-inflammatory agent may be selected from a steroidal drug and a NSAID (nonsteroidal anti-inflammatory drug).

In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies (e.g. 10F8 described in WO2004/058797), anti-IL15 antibodies, anti-IL15R antibodies, anti-CD4 antibodies, anti-CD11a antibodies (e.g., efalizumab), anti-alpha-4/beta-1 integrin ($V_LA4$) antibodies (e.g natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In a further embodiment, the combination therapy of the invention further includes administration of at least one immunosuppressive and/or immunomodulatory agent to a subject in need thereof.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, or antibodies binding to for instance MHC, CD2, CD3, CD4, CD7, CD28, B7, CD40, CD45, IFNγ, TNF-α, IL-4, IL-5, IL-6R, IL-6; IGF, IGFR1, IL-7, IL-8, IL-10, CD11a, or CD58, or antibodies binding to their ligands.

In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents.

In a further embodiment, the combination therapy of the invention further includes administration of an anti-C3b(i) antibody.

In a further embodiment, the combination therapy of the invention further includes administration of histone deacetylase inhibitors (for instance phenylbutyrate) and/or DNA repair agents (for instance DNA repair enzymes and related compositions such as dimericine).

In a further embodiment, the combination therapy of the invention further includes anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004).

All methods described herein can be performed in any suitable order unless otherwise indicated herein or otherwise clearly contradicted by context.

All patents, pending patent applications and other publications cited herein are hereby incorporated by reference in their entirety.

The present invention is further illustrated by the following examples which should not be construed as further limiting.

EXAMPLES

Example 1

Manufacturing Luciferase-transfected (Daudi-luc) Cells

Culture of Daudi cells (originating from Burkitt's lymphoma) was cultured in RPMI 1640 culture medium supplemented with 10% FCS (Optimum C241, Wisent Inc., St. Bruno, QC, Canada), 2 mM L-glutamine, 100 IU/ml penicillin, 100 mg/ml streptomycin, 1 mM sodium pyruvate (all derived from Gibco BRL, Life Technologies, Paisley, Scotland). Medium was refreshed twice a week. Before transfection, cells were split and seeded out at 1-1.5×10⁶ cells/ml to ensure viability and optimal growth.

Luciferase Transfection 8.2×10⁶ CD38⁺ Daudi cells were taken up in 350 µl RPMI (supplemented with 10% dFCS, Gibco BRL) and transferred to an electroporation cuvet (Biorad, Hemel Hempstead, Herts, UK). Then, 40 µg gWIZ luciferase from GTS (Aldevron, Fargo, N. Dak., USA) and 10 µg pPur vector (BD Biosciences, Alphen a/d Rijn, The Netherlands), which confers puromycin resistance, were added. After resting cells on ice for 10 minutes, cells were electroporated (250 V, 950 µF; Gene Pulser II, Biorad Laboratories GmbH, München, Germany). Cells were again rested on ice, and taken up in 40 ml RPMI (supplemented with 10% FCS). Then, cells were plated out in 96-well tissue culture plates (100 µl per well). After 48 hours, puromycin (final concentration: 1 µg/ml; Sigma-Aldrich Chemie B V, Zwijndrecht, The Netherlands) was added. Puromycin-resistant clones were further grown in 24-well tissue culture plates.

Determination of Luciferase Activity

Luciferase activity of cells was determined using the Luciferase Assay System (#E4030, Promega, Madison, Wis., USA). 1×10⁵ cells were centrifuged (13.500 rpm, 1 min) in an eppendorf centrifuge, and the pellet was washed in 100 µl PBS. After centrifugation (13.500 rpm, 1 min), pellet was lysed with 20 µl Reporter Lysis Buffer (Promega), frozen and thawed. After centrifugation (13,500 rpm, 1 min), 20 µl supernatant was discarded, and 100 µl luciferase assay reagent was added (in special luminometer tubes, Promega). Luminescence was measured (10 sec) in a luminometer (LB9507, Berthold, Vilvoorde, Belgium).

Example 2

Immunization of Mice and Generation of Hybridomas

Immunization Protocol for -003

HCo12 mice were immunized every fortnight with 20 µg purified HA-CD38. The first immunization was performed i.p. in the presence of 100 µl PBS, mixed with 100 µl Complete Freund's Adjuvant (CFA). After this first immunization, subsequent boosts (13×) with purified HA-CD38 were performed in the presence of 100 µl PBS, mixed with 100 µl Incomplete Freund's Adjuvant (IFA) alternating s.c. and i.p. After titer development, mice were boosted with 20 µg HA-CD38 in PBS, i.v.

Immunization Protocol for -005 and -024

HCo12 mice were immunized every fortnight with 20 µg purified HA-CD38 alternating with NIH-3T3-CD38 transfected cells. The first immunization was performed with 5×10⁶ cells in 100 µl PBS, mixed with 100 µl CFA, i.p., the second and following immunizations with HA-CD38 s.c., in the presence of 100 µl PBS, mixed with 100 µl IFA. The following immunizations with transfected cells were performed in the presence of 200 µl PBS. After titer development, mice were boosted with 20 µg HA-CD38 in PBS, i.v.

Generation of Hybridomas Producing Human Monoclonal Antibodies to CD38

The mouse splenocytes were isolated from HCo12 mice and fused with PEG to a mouse myeloma cell line based upon standard protocols. The resulting hybridomas were then screened for human antibody production by ELISA and for CD38 specificity using human CD38-transfected NS/0 cells by FACS analysis and recombinant HA-CD38 protein binding by ELISA. Three hybridoma cell lines were selected expressing the human monoclonal anti-CD38 antibodies, -003, -005 and -024, respectively.

Example 3

Transfection of NIH Cells with CD38

The vector (pclpuroCD38) for producing NIH-3T3-CD38 cells was obtained from Prof. M. Glennie (Tenovus Research Laboratory, Southampton General Hospital, Southampton, UK). NIH-3T3 cells (DSMZ, ACC 59; 150,000 cells/well; 0.5 ml; 96-well flat-bottom plates, Greiner) were cultured in DMEM (supplemented with glucose [4.5 g/l], 10% FCS, L-glutamine, Na-pyruvate; BioWhittaker) for 24 h. Then, DNA (0.8 µg) and lipofectamine (Invitrogen, Breda, The Netherlands) were diluted in DMEM, and mixed (20 min, RT). Thereafter, the mixture (100 µl) was added to each well and incubated (ON, 37° C.).

Screening for CD38 Expression

NIH-3T3-CD38 cells were washed (in 1 ml PBS) and trypsinized (200 µl, trypsin-EDTA, BioWhittaker). Then, 1 ml of DMEM was added and the mixture pipetted into FACS tubes. After centrifugation (1200 rpm, 5 min), cells were washed in FACS Buffer (FB; PBS, 0.05% BSA, 0.02% NaN₃) and resuspended in 1 ml FB. After centrifugation (1200 rpm, 5 min), supernatant was removed and mouse anti-human CD38-PE was added (1/50 dilution, Sanquin, Amsterdam, The Netherlands). After washing the cells twice in FB, cells were resuspended in FB for acquisition by flow cytometry.

Expansion and Selection

After trypsine treatment, cells were transferred to T25 flasks (Greiner) in DMEM (supplemented with glucose 4.5 g/l, 2 mM L-glutamine, and puromycin (2 µg/ml) BioWhittaker). Puromycin-resistant cells were tested for stable CD38 expression by flow cytometry after two weeks on puromycin-containing medium. NIH-3T3-CD38 selected cells were subcloned by limiting dilution. After expanding these cells, all 15 NIH-3T3-CD38 clones were screened for CD38 expression. CD38high NIH-3T3-CD38 cells were frozen in liquid nitrogen (−80° C.) until use.

Culture of NIH-3T3-CD38 Cells

Cells are cultured in DMEM (supplemented with glucose (4.5 g/l), 10% FCS, 2 mM L-glutamine, Na-pyruvate, penicillin, streptomycin). Cells are passaged twice a week by use of trypsin/EDTA and seeded in a concentration of 1×10⁶ cells/T75 flask. CD38high NIH-3T3-CD38 cells were frozen in liquid nitrogen (−80° C.) until use.

Purification of HA-CD38 Antigen

Sepharose 4B (Amersham Bioscience, Uppsala, Sweden) was coupled with anti-CD38 antibody (Serotec, Oxford, UK). Column (column tube HR5/20 was packed to 12 cm bedheight, column volume 2.4 ml; maximum flow rate 0.5 ml/min) was equilibrated with at least 5 column volumes (CV) of PBS. Sample was filtrated and loaded to the column. Column was washed with PBS until signal returned to baseline (approximately 3 CV). Elution was carried out with 0.1M glycine at pH 2. Eluted fractions were neutralized with 1% (v/v) 2 M Tris-HCl, pH 9.

Purification of Anti-CD38 Antibodies

Human anti-CD38 antibodies were purified from tissue culture supernatants. First, the supernatants were filtered over 0.20 µM dead-end filter. Then, the supernatant was loaded on a 5 ml Protein A column (rProtein A FF, Amersham Bioscience) and eluted with 0.1 M citric acid-NaOH, pH 3. The eluate was immediately neutralized with 2 M Tris-HCl, pH 9 and dialyzed O/N to 12.6 mM sodium phosphate, 140 mM NaCl, pH 7.4 (B. Braun, Oss, The Netherlands). After dialysis samples were sterile filtered over 0.20 µM dead-end filter.

Purification of His-CD38 Batches

The protein is present in cell culture supernatant of His-CD38-expressing cells, with a DNA construct containing the sequence for the extracellular domain of CD38. An additional poly-His-tag sequence is included in the constructs and present at the N-terminus of the protein. This tag enables purification with immobilized metal affinity chromatography. In this process, a chelator fixed onto the chromatographic resin is charged with $Co^{2+}$ cations. Particularly, a sequence that includes 6 histidine amino acids strongly binds $Co^{2+}$.

Therefore the His-tagged CD38 proteins bind strongly to such a column, while other proteins present in the culture supernatant will flow through the column or will be washed away. The strongly bound His-tagged CD38 proteins are then eluted with a buffer containing imidazole, which competes with the binding of His to $Co^{2+}$. When sufficient His-CD38 is purified, the eluent is removed from the protein by buffer exchange on a desalting column.

Example 4

Binding of -003, -005, and -024 to CD38-Transfected CHO (CHO-CD38) Cells, to Daudi-luc Cells and to Fresh Multiple Myeloma (MM) Tumor Cells After harvesting and counting, Daudi-luc cells, CHO cells transfected with CD38 and control CHO cells were resuspended in PBS ($1\times10^6$ cells/ml). Then, cells were put in 96-well V-bottom plates (100 µl/well) and washed twice in PBS-BSA (PBS supplemented with 0.1% BSA and 0.02% Na-azide). Thereafter, 50 µl antibody solution in PBS-BSA was added to the cells (4° C., 30 min). After washing three times in PBS-BSA, 50 µl (1:400 dilution) of rabbit anti-human IgG-FITC in PBS-BSA was added (4° C. in the dark, 30 min). Cells were washed three times and specific binding of CD38-antibodies to CHO-CD38 and Daudi-luc cells was detected by flow cytometry. HuMab-KLH (a human monoclonal antibody against KLH (keyhole limpet haemocyanin) generated by Genmab B. V., Utrecht, The Netherlands by use of the immunization protocols described elsewhere herein) was used as a control. FIGS. 1 and 2 show that -003, -005, and -024 bind to CHO-CD38 cells and to Daudi-luc cells, albeit with different $EC_{50}$ (Table 1). No binding to control CHO cells is observed (data not shown).

Fresh MM tumor cells were obtained from Dr. Lokhorst (University Medical Center Utrecht, Utrecht, The Netherlands. Tumor cells were isolated from bone marrow of multiple myeloma patients by Ficoll (Bio Whittaker; lymphocyte separation medium, cat 17-829E) gradient centrifugation. After harvesting and counting, MM cells (100,000 cells/well) were resuspended with 25 µl FITC-labeled CD38-specific antibodies and 25 µl CD138. After incubation (4° C., 30 min), cells were washed in PBS-BSA and PE-labeled goat-anti-mouse IgG (1:200; Jackson ImmunoResearch Europe Ltd. Soham, UK) was added. After incubation (4° C., 30 min) and washing of the cells in PBS-BSA, fluorescence was measured by flow cytometry.

FIG. 3 shows that -003, -005 and -024 bind to MM cells.

TABLE 1

$EC_{50}$ values of binding of anti CD38-antibodies on CHO-CD38 cells, Daudi-luc cells and fresh MM tumor cells.

| CD38-specific antibodies | $EC_{50}$ CHO-CD38 (µg/ml) | $EC_{50}$ Daudi-luc (µg/ml) | $EC_{50}$ MM cells (µg/ml) |
|---|---|---|---|
| -003 | 0.54 | 0.26 | 0.56 |
| -005 | 0.23 | 0.09 | 0.04 |
| -024 | 0.08 | 0.05 | 0.02 |

Example 5

Antibody-dependent Cell-mediated Cytotoxicity

Daudi-luc cells, fresh multiple myeloma tumor cells, fresh Plasma Cell Leukemia tumor cells and JK6L and AMO-1 multiple myeloma cells were collected ($5\times10^6$ cells) in $RPMI^{++}$ (RPMI 1640 culture medium supplemented with 10% cosmic calf serum (HyClone, Logan, Utah, USA)), to which 100 µCl $^{51}$Cr (Chromium-51; Amersham Biosciences Europe GmbH, Roosendaal, The Netherlands) was added, and the mixture was incubated in a 37° C. water bath for 1 hr. After washing of the cells (twice in PBS, 1500 rpm, 5 min), the cells were resuspended in $RPMI^{++}$ and counted by trypan blue exclusion. Cells were brought at concentration of $1\times10^5$ cells/ml.

Preparation of Effector Cells

Fresh peripheral blood mononuclear cells (healthy volunteers, UMC Utrecht, Utrecht, The Netherlands) were isolated from 40 ml of heparin blood by Ficoll (Bio Whittaker; lymphocyte separation medium, cat 17-829E) according to the manufacturer's instructions. After resuspension of cells in $RPMI^{++}$, cells were counted by trypan blue exclusion and brought at concentration of $1\times10^7$ cells/ml.

ADCC Set Up

50 µl of $^{51}$Cr-labeled targets cells were pipetted into 96-well plates, and 50 µl of antibody was added, diluted in $RPMI^{++}$ (final concentrations 10, 1, 0.1, 0.01 µg/ml). Cells were incubated (RT, 15 min), and 50 µl effector cells were added, resulting in an effector to target ratio of 100:1 (for determination of maximal lysis, 100 µl 5% Triton-X100 was added instead of effector cells; for determination of spontaneous lysis, 50 µl target cells and 100 µl $RPMI^{++}$ were used). Cells were spun down (500 rpm, 5 min), and incubated (37° C., 5% $CO_2$, 4 hr). After spinning down cells (1500 rpm, 5 min), 100 µl of supernatant was harvested into micronic tubes, and counted in gamma counter. The percentage specific lysis was calculated as follows:

(cpm sample−cpm target cells only)/(cpm maximal lysis−cpm target cells only) wherein cpm is counts per minute.

In Daudi-luc cells (FIG. 4 and Table 2) -003, -005, and -024 induce lysis by ADCC, and -003, and -005 perform slightly better than rituximab (anti-CD20 mAb). Interestingly, also when fresh multiple myeloma tumor cells (obtained from Dr. H. Lokhorst, UMCU, The Netherlands) are used as target cells, ADCC is induced by -003, -005 and -024 (FIG. 5A and Table 2).

TABLE 2

$EC_{50}$ values of CD38-specific antibodies obtained in ADCC

| CD38-specific antibodies | $EC_{50}$ Daudi-luc (ng/ml) | $EC_{50}$ MM cells (ng/ml) |
|---|---|---|
| -003 | 9.0 | 27 |
| -005 | 4.5 | 5.7 |
| -024 | 9.7 | 56 |

Enrichment of Human Peripheral Blood Mononuclear Cells Erlangen

Human blood from human volunteers (University Erlangen, Erlangen, Germany) was diluted twice in RPMI 1640 and blood cells were layered on Ficoll (Lymphocyte Separation Medium 1077 g/ml, 710 g, RT, 20 min; BioWhittaker, Cambrex Bio Science Verviers, Verviers, Belgium, cat. 17-829E, lot no. 0148 32). Peripheral blood mononuclear cells (MNCs) were collected from the interphase, washed and resuspended in RPMI 1640 culture medium supplemented with 10% FCS, 2 mM L-glutamine, 5 U/ml penicillin, 50 µg/ml streptomycin (all derived from BioWhittaker) to which 25 mM HEPES (BioWhittaker) was added.

ADCC Set Up II

Target B-cells (fresh plasma cell leukemia tumor cells, JK6L and AMO-1 B-cell lines, obtained from Dr. T. Valerius, University of Erlangen, Erlangen, Germany) were labeled with 20 µCi $^{51}$Cr (Amersham Biosciences, Uppsala, Sweden) for 2 hours. After extensive washing in RPMI-10, cells were adjusted to $1\times10^5$ cells/ml. MNCs (50 µl), sensitizing antibodies (50 µl), and RPMI-10 (50 µl) were added to round-bottom microtiter plates (Greiner Bio-One GmbH, Frickenhausen, Germany). Assays were started by adding fresh plasma cell leukemia tumor cells, JK6L or AMO-1 cells (50 µl) giving a final volume of 200 µl. An effector to target (E:T) ratio of 40:1 was used. After incubation (3 hr, 37° C.), assays were stopped by centrifugation, and $^{51}$Cr release from triplicates was measured in counts per minute (cpm) in a scintillation counter. Percentage of cellular cytotoxicity was calculated using the following formula:

% specific lysis=(experimental cpm−basal cpm)/
(maximal cpm−basal cpm)×100 with maximal $^{51}$Cr release determined by adding perchloric acid (3% final concentration) to target cells, and basal release was measured in the absence of sensitizing antibodies and effector cells.

Figure 6:
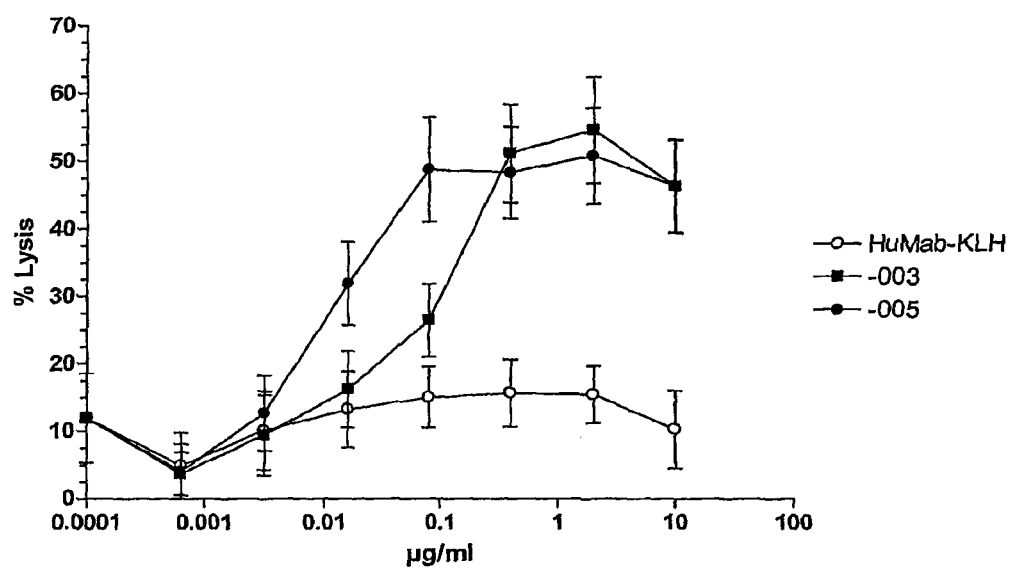
FIG. 6 shows the ability of -003 and -005 to induce lysis of JK6L (a multiple myeloma cell line) by ADCC as compared to HuMab-KLH. The experimental setup is described in Example 5.
Figure 7:
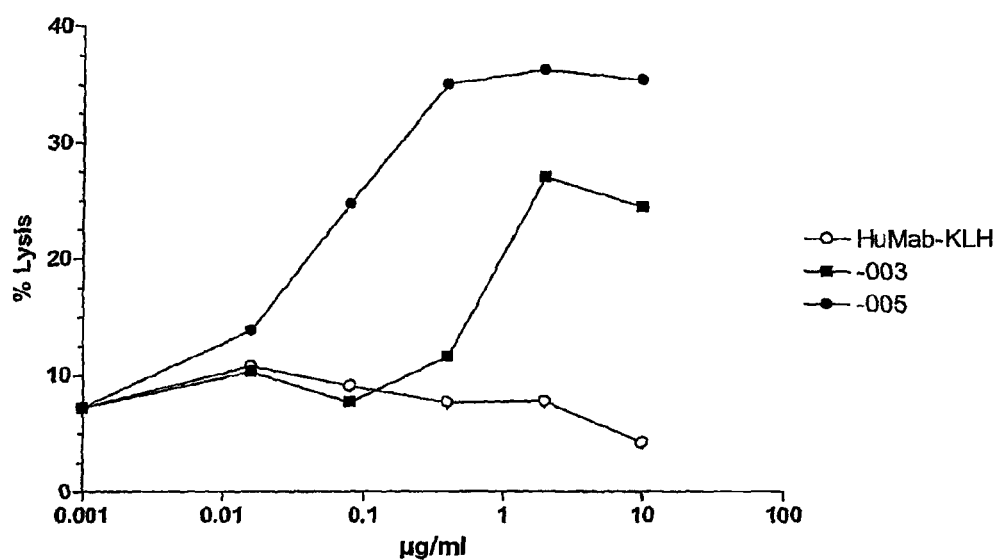
FIG. 7 shows the ability of -003 and -005 to induce lysis of AMO-1 (a multiple myeloma cell line) by ADCC as compared to HuMab-KLH. The experimental setup is described in Example 5.

In both multiple myeloma cell lines (i.e. JK6L and AMO-1), lysis is induced with both -003 and -005 (FIGS. 6 and 7), even when CD38 expression is low (AMO-1 cell line).

-003, -005 and -024 induce ADCC of plasma cell leukemia primary tumor cells (FIG. 5B).

Example 6

Complement-dependent Cytotoxicity

After harvesting and counting of Daudi-luc cells, the viability of the cells should be ≥90%. After washing (PBS), cells are resuspended at 2.0×10$^6$ cells/ml in RPMI-B (RPMI supplemented with 1% BSA). Thereafter, cells are put in 96-well round-bottom plates at 1×10$^5$ cells/well (50 µl/well). Then, 50 µl antibodies is added to the wells (final concentration range between 0-100 µg/ml (three-fold dilutions in RPMI-B)). After incubation (RT, 15 min), 11 µl of pooled human serum (pool of 18 healthy donors) was added to each well (37° C., 45 min). Wells were resuspended once and 120 µl was transferred to FACS tubes (Greiner). Then, 10 µl propidium iodide (PI; Sigma-Aldrich Chemie B. V.) was added (10 µg/ml solution) to this suspension. Lysis was detected by flow cytometry (FACScalibur™, Becton Dickinson, San Diego, Calif., USA) by measurement of the percentage of dead cells (corresponds to PI-positive cells).

Figure 8:
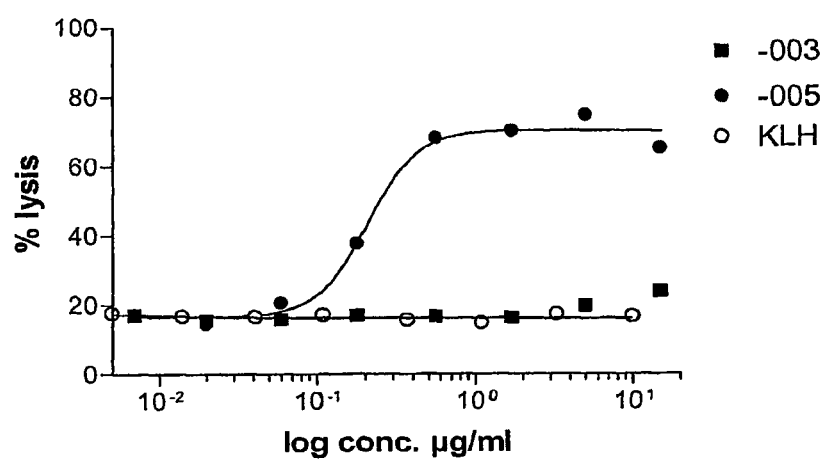
FIG. 8 shows the CDC-mediated lysis of Daudi-luc cells induced by -003 and -005 compared to HuMab-KLH. The experimental setup is described in Example 6.

FIG. 8 and Table 2 show that lysis of Daudi-luc cells is induced by -005 (~60% maximum lysis) and that lysis by -003 is only seen at very high antibody concentrations. -024 does not induce CDC in Daudi cells (data not shown). In CHO-CD38 cells, lysis is induced by both -003, -005, and -024 (FIG. 9 and Table 3). Lysis by -003 is induced at higher concentrations. In tumor cells (all obtained from Dr. Lokhorst and Dr. Bloem, University Medical Center Utrecht, The Netherlands), obtained from different MM patients (A: 3% refractory tumor cells, B: 9% refractory tumor cells, C: 30-40% tumor cells, and D: 70% tumor cells), CDC-mediated lysis is observed in the presence of -005, but not in the presence of -003 (FIG. 10). -024 also induced lysis of MM tumor cells (FIG. 10E).

TABLE 3

EC$_{50}$ values of CD38-specific antibodies obtained in CDC

| CD38-specific antibodies | EC$_{50}$ Daudi-luc (µg/ml) | EC$_{50}$ CD38-CHO (µg/ml) |
| --- | --- | --- |
| -003 | >90 | 3.14 |
| -005 | 0.33 | 0.14 |
| -024 | >90 | 0.24 |

Example 7

Cross-block Studies Using FACS

Figure 11:
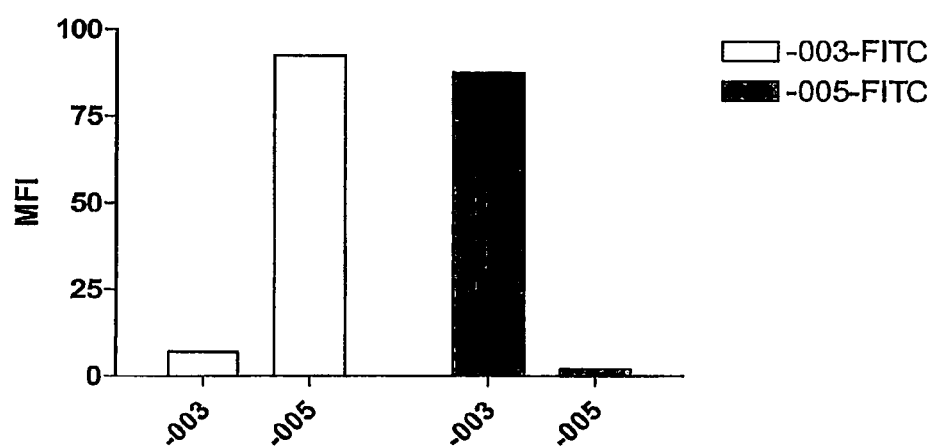
FIG. 11 shows that -003 and -005 do not cross-block binding to CD38. The experimental setup is described in Example 7.

CHO-CD38 cells were incubated with an excess of unlabelled CD38-specific antibody (4° C., 15 min). Then, cells were incubated with FITC-labeled CD38-specific antibodies (concentration approximates EC$_{90}$, 4° C., 45 min). After twice washing the cells with PBS-BSA, fluorescence was measured by flow cytometry. FIG. 11 shows that unlabelled -003 blocks binding of FITC-labeled -003, whereas binding of FITC-labeled -005 is not blocked. Also unlabelled -005 blocks binding of FITC-labeled -005, whereas binding of FITC-labeled -003 is not blocked. -003 and -005 bind to different epitopes, because they do not compete for binding.

Example 8

Cross-blocking Studies Using ELISA

Soluble human CD38 is coated on the surface of an ELISA plate. Coated CD38 is incubated with an excess of unlabelled CD38 specific antibodies for about 15 minutes and subsequently biotinylated CD38-specific antibodies are added (concentration approximates EC$_{90}$, RT, 1 hour). After washing three times with PBS/Tween, horseradish peroxidase (HRP)-conjugated streptavidine is added and the mixture is incubated for 1 hour at RT. The complex can be detected by addition of an ABTS-solution and the HRP mediated substrate conversion is measured using an ELISA reader at OD 405 nm.

Example 9

Cross-blocking Studies Using Sandwich-ELISA

CD38 specific antibodies are coated on the surface of an ELISA plate. Plate-bound antibodies are incubated with biotinylated soluble CD38 in the presence of an excess of CD38 specific antibodies in fluid phase. After washing with PBS/Tween, bound biotinylated CD38 is detected with HRP-conjugated streptavidine for 1 hr at RT. This complex can be detected by addition of an ABTS-solution (after washing with PBS/Tween) and the HRP mediated substrate conversion is measured using an ELISA reader at OD 405 nm.

Example 10

Reactivity with a Panel of Human Tissues and Cross-reactivity with Cynomolgus Tissue by Immunohistochemistry Sections from frozen human tissue (obtained from Dr. H. Niessen, Free University Medical Center, Amsterdam, The Netherlands) or monkey tissue (Inveresk Research, Glasgow, Scotland) were cut at 6 µm and air-dried overnight. These cryostat sections were fixated in acetone (RT, 10 min) and air-dried (approx. 5 min). Thereafter, sections were incubated with 1× citric acid/phosphate buffer containing 0.1% H$_2$O$_2$ (pH 5.8; Sigma), to block endogenous peroxidase. After 20 min at RT, sections were washed twice with PBS and 0.05% Tween-20 (PBST, RT, 5 min; Riedel de-Haen, Germany). Then, sections were incubated with avidin (RT, 15 min; DAKO, Glostrup, Denmark), washed twice with PBST, and incubated with biotin (RT, 15 min; DAKO) to block endogenous biotin. After washing the sections twice with PBST, sections were pre-incubated with PBST$^{++}$ (PBST supplemented with 10% normal human serum (NHS, CLB, Amsterdam, Netherlands) and 10% normal goat serum (NGS; DAKO) (RT, 20 min). After blotting-off of the pre-incubation serum, sections were incubated with FITC-labeled primary antibody diluted in 2% PBST$^{++}$ at the indicated concentrations (RT, 60 min). Thereafter, sections were incubated with rabbit-anti-FITC (1:1000; DAKO) in 2% PBST$^{++}$ (RT, 30 min). After washing the sections with PBST, sections were incubated with goat-anti-rabbit-biotin (1:400; DAKO) in 2% PBST$^{++}$ (RT, 30 min). Then, sections were washed and incubated with SABC-HRP (1:100; DAKO) in 2% PBST$^{++}$ (RT, 30 min). After washing the sections twice in PBST, they were incubated (RT, 10 min) with amino-ethyl-carbazole (AEC)-development solution (50 mM acetate buffer, pH4.9, 0.01%

H₂O₂; Riedel-de-Haen). Finally, sections were washed in millipore H₂O (5 min) and counterstained with hematoxylin (DAKO). By use of glycergel (37° C.), sections were fixed with cover slips, and studied by light microscopy (Axiovision-2; Zeiss, Thornwood, N.Y., USA).

Bronchial epithelium is stained with -003 and -005 (FIGS. 12B and 13B) as well as striated muscle (myocytes, FIGS. 12C and 13C), macrophages, lymphocytes and plasma B cells (FIGS. 12A and 13A). -024 has a similar staining of striated muscle and bronchial epithelium, but staining was less intense. No staining of endothelial cells is observed, neither with -003 (FIG. 14D), -005 (14E) nor -024 (data not shown), whereas clear staining was observed with the positive control antibodies against endothelial cell markers CD31 (FIG. 14A) and vWF (14B). Anti-KLH was used as negative control antibody (FIG. 14C). -003 (FIG. 12D) and -024 (data not shown) but not -005 (FIG. 13D) cross-react with cynomolgus monkey lymphoid tissue.

Example 11

Cross-reactivity with Cynomolgus or Rhesus Monkey Peripheral Blood Mononuclear Cells (PBMCs) by Flow Cytometry 5 ml of cynomolgus monkey peripheral blood (Inveresk Research) were lysed by adding 4.5 ml shock buffer (1.7 mM NH4CL, 1 mM EDTA), 40 ml H₂O and 450 µl 10% KHCO₃. After hemolysis cells were centrifuged (1200 rpm, 10 min) and washed thrice in PBS. After counting cells with trypan blue, cells were resuspended in PBS-BSA (1×10⁶ cell/ml).

17.5 ml of rhesus monkey peripheral blood (BPRC, Rijswijk, The Netherlands) was diluted 1:1 with RPMI 1640 and layered on Ficoll (1.077 g/ml; BioWhittaker, cat. 17-829E, lot no. 0148 32). After centrifugation (710 g, RT, 20 min), the interphase was collected and washed twice in RPMI. After the last wash cells were resuspended in RPMI 1640 at a concentration of 1×10⁵ cells/50 µl.

Cells were transferred to 96-well plate (100,000 PBMCs/well), washed in FACS buffer (PBS, 0.05% BSA, 0.02% NaN₃) and incubated with the primary antibodies (4° C., 30 min). After washing in PBS-BSA, 50 µl FITC-labeled rb-anti-hIgG (DAKO, Glostrup, Denmark) was added (4° C., 30 min). Finally, cells were collected in FACS tubes in a total volume of 150 µl. Samples were measured and analyzed by use of FACScalibur™ (Becton Dickinson, San Diego, Calif., USA).

Figure 15A:
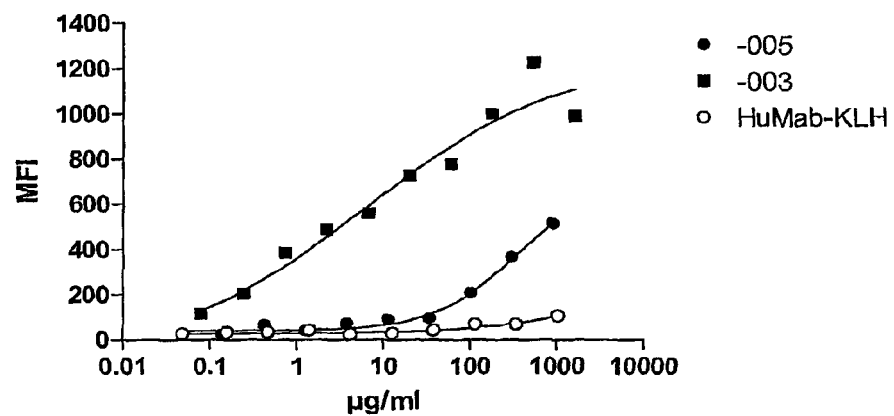
FIG. 15A shows the cross-reactivity of -003 and -005 compared to HuMab-KLH on cynomolgus lymphocytes as measured by flow cytometry. The experimental setup is described in Example 11.
Figure 15B:
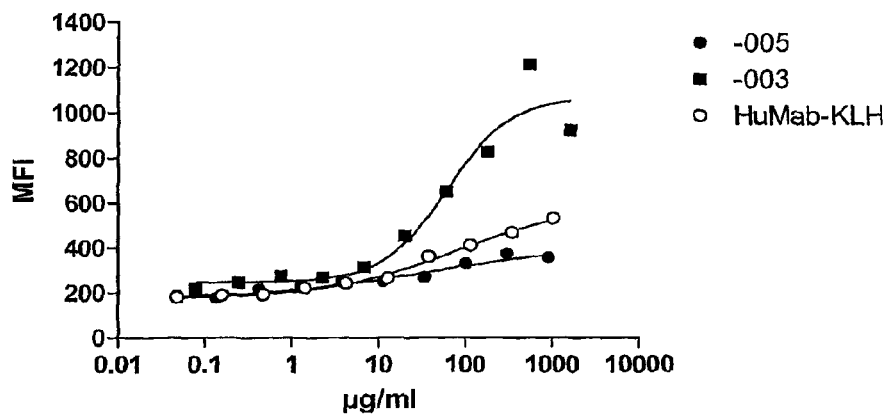
FIG. 15B shows the cross-reactivity of -003 and -005 compared to HuMab-KLH on cynomolgus monocytes as measured by flow cytometry. The experimental setup is described in Example 11.
Figure 15C:
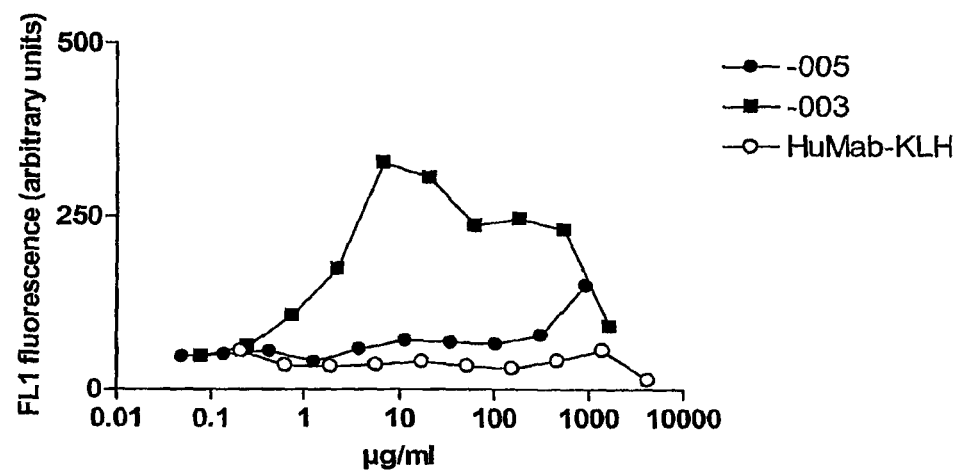
FIG. 15C shows the cross-reactivity of -003 and -005 compared to HuMab-KLH on rhesus monkey PBMCs as measured by flow cytometry. The experimental setup is described in Example 11.

With flow cytometry cross-reactivity of -003 on cynomolgus lymphocytes (FIG. 15A) and monocytes (FIG. 15B) was shown, but not of -005. Also in rhesus monkeys, cross-reactivity of -003 was observed on mononuclear cells, but not of -005 (FIG. 15C).

Example 12

Internalization Experiments

CHO-CD38 cells were stained with a saturating concentration of FITC-labeled CD38-specific antibodies (on ice, 30 min). After washing of cells (in RPMI 1640 supplemented with 10% FCS), one cell pool was warmed up to 37° C. to allow internalization, and the other pool was left on ice. At several time intervals (0-120 min) cell aliquots were taken and transferred to ice-cold PBS-BSA to stop internalization. After washing samples twice with PBS-BSA, EtBr (diluted in PBS-BSA, final concentration 2 mg/ml) was added to the samples to quench membrane-bound FITC. Fluorescence was measured by flow cytometry.

FIGS. 16A and 16B show that -003 and -005 are internalized by CHO-CD38 cells within 5 minutes at 37° C.

Example 13

In Vivo SCID-luciferase Experiments

In this model tumor cells are transfected with firefly luciferase. Upon administration of luciferin (Molecular Probes, Leiden, The Netherlands) to the mice the labeled cells can be detected in vivo by bioluminescent imaging using a highly sensitive CCD camera, cf. Wetterwald et al., American Journal of Pathology 160(3), 1143-1153 (2002).

Daudi cells were transfected with gWIZ luciferase from Gene Therapy Systems (San Diego, Calif.) and cultured in RPMI with 10% FCS, Pen/Strep, Sodium Pyruvate and 1 µg/ml puromycin (Sigma). Cells were analysed for luciferase expression (expressed in RLU/1×105 cells) in a luminometer and for CD38 expression by FACS. 2.5×10⁶ luciferase-transfected Daudi cells/mouse were injected i.v. into SCID mice. Mice were treated with -003, -005, isotype control antibody (HuMab-KLH) or rituximab (anti-CD20 antibody). Antibodies were injected intraperitoneally. Four treatment settings were used (see Table 4). In the preventive setting, antibody (100 µg/mouse) and cells were administered simultaneously. In therapeutic setting I, antibody (300 µg/mouse) was administered 7 days after administration of cells. In therapeutic setting II, antibody (10 µg/mouse) was administered 14 days after administration of cells. In therapeutic setting III, antibody (100 µg/mouse) was administered 7 days after administration of cells. For imaging, mice were anesthetized by i.p. injection of a mixture of ketamine/xylazine/atropine. Synthetic D-Luciferin (sodium salt, Molecular Probes) was given i.p. at a dose of 25 mg/ml. Mice were then placed in a light tight box and after 3 min, imaging was started using a VersArray 1300B liquid nitrogen cooled CCD detector (Roper Scientific). Photons emitted from the luciferase were counted over an exposure period of 5 min. Under illumination black and white images were made for reference. MetaVue software (Universal Imaging Corp) was used for data collection and image analysis. Statistical significance of differences between groups was established using one-way analysis of variance with a Newman-Keuls post test using GraphPad PRISM version 3.02 (Graphpad Software Inc).

TABLE 4

Treatment settings for in vivo luciferase experiments

| Experimental setting | Antibody treatment (days after cell inoculation) | Antibody dose (µg/mouse) |
| --- | --- | --- |
| Preventive setting | 0 | 100 |
| Therapeutic setting | 7 | 300 |
| Therapeutic setting II | 14 | 10 |
| Therapeutic setting III | 7 | 100 |

Figure 17A:
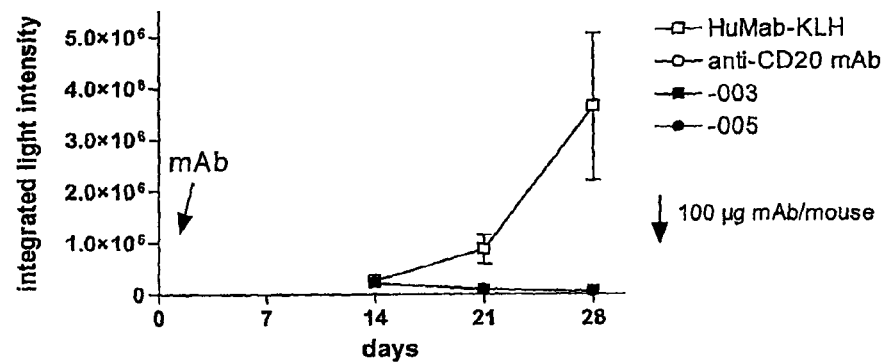
FIG. 17A shows the inhibition caused by -003 and -005 compared to an anti-CD20 monoclonal antibody (rituximab) and HuMab-KLH of the growth of tumor cells in a preventive setting as measured by in vivo SCID luciferase imaging. The experimental setup is described in Example 13.
Figure 17B:
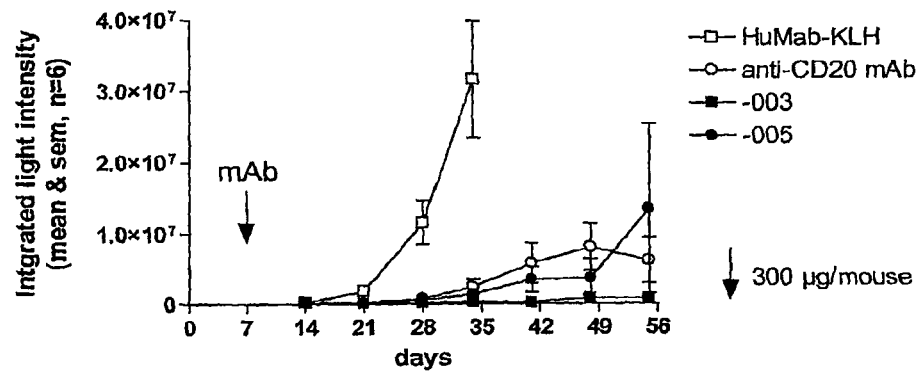
FIG. 17B shows the inhibition caused by -003 and -005 compared to an anti-CD20 monoclonal antibody (rituximab) and HuMab-KLH of the growth of tumor cells in therapeutic setting I as measured by in vivo SCID luciferase imaging. The experimental setup is described in Example 13.
Figure 17C:
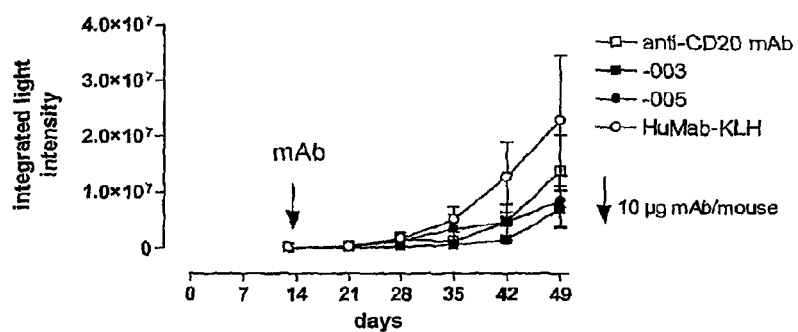
FIG. 17C shows the inhibition caused by -003 and -005 compared to an anti-CD20 monoclonal antibody (rituximab) and HuMab-KLH of the growth of tumor cells in therapeutic setting II as measured by in vivo SCID luciferase imaging. The experimental setup is described in Example 13.
Figure 17D:
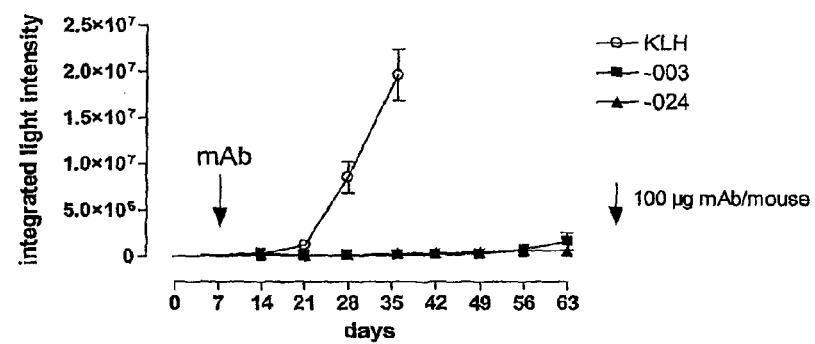
FIG. 17D shows the inhibition of tumor cell growth by -003 and -024 compared to HuMab-KLH in therapeutic setting III as measured by in vivo SCID luciferase imaging. The experimental set up is described in Example 13.

FIGS. 17A and 17B show that -003 and -005 inhibit growth of tumor cells in the preventive setting and in therapeutic setting I, similar to the inhibition observed for the anti-CD20 antibody. Both antibodies perform significantly better than the isotype control antibody. Also in therapeutic setting II CD38-antibodies slow down the growth of Daudi-luc tumor cells (FIG. 17C). In therapeutic setting III, -003 and -024 show a clear inhibition of Daudi-luc tumor cell growth (FIG. 17D).

Example 14

Apoptosis

Apoptosis assay was carried out according to the manufacturer's instructions (Annexin-V Apoptosis kit, BD Biosciences, Alphen a.d. Rijn, Netherlands). In short, CD38 mAbs were added to 2.5×10⁵ cells (luciferase-transfected Daudi cells, in 0.5 ml RPMI⁺⁺ in a 24-wells plate), in a concentration of 5 µg/ml -003 or -005 or an anti-CD20 antibodies alone or in the presence of cross-blocking rb-anti-hIgG (50 µg/ml).

After incubation (37° C., 5% $CO_2$, 20 hr), cells were harvested carefully, and washed with Binding Buffer (1200 rpm, 4° C., 5 min, BD Biosciences). Pellet was resuspended in 100 µl Binding Buffer. Then, 5 µl Annexin-V-FITC (BD Biosciences) and 10 µl PI (BD Biosciences) was added to the suspension and incubated for 15 minutes at RT. 400 µl Binding Buffer was added and the samples were measured (PI readout in FL2). For analysis of apoptotic cells, all Annexin-V-positive cells were counted by flow cytometry using a FACScalibur flow cytometer with CellQuest pro software (BD Biosciences). At least 10,000 events were collected for analysis. This population includes both PI-positive as well as PI-negative cells.

Figure 18:
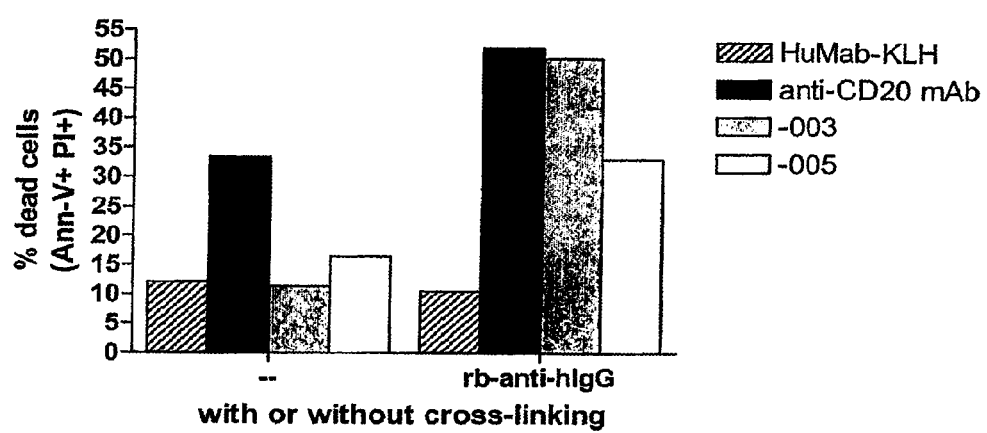
FIG. 18 shows the induction of apoptosis by -003 and -005 compared to an anti-CD20 monoclonal antibody (rituximab) and HuMab-KLH without or with cross-linking. The experimental setup is described in Example 14.

FIG. 18 shows that -003 and -005 do not induce apoptosis. However, after cross-linking, apoptosis of target cells is observed. -003 induced apoptosis after cross-linking that was similar to apoptosis induced by an anti-CD20 antibody (rituximab). -005 was less able to induce apoptosis after cross-linking. Similar results were obtained with RAMOS cells as target cells (data not shown).

Example 15

Effect of -005 on Tissue Graft B Cells in RA-SCID Mouse Model

Implantation of Synovial Tissue

SCID-mice, strain C.B.-17/IcrCrl-SCID-bg, male/female, 4-12 weeks, purchased from Charles River Laboratories Nederland (Maastricht, the Netherlands) were kept in IVC cages under standard conditions of temperature and light, and were fed laboratory chow and water ad libitum. Prior to implantation, mice (three mice in each experimental group, day 0) were anesthetized by intraperitoneal injection of ketamine (NIMATEK, EuroVet) and xylazine (Rompun, Bayer) at ratio 1:1. A small incision of the skin was made using surgical scissors. Inflamed synovial tissue from a patient with rheumatoid arthritis undergoing joint replacement surgery was implanted subcutaneously as a cluster of six small fragments (total 2-3 mm$^3$) on each flank of the mouse. The wound was closed using Permacol cyanoacrylate glue. On day 1 of the experiment, remaining synovial tissue was analyzed in order to check for B cells in the inflamed synovial transplants. -005 (12 mg/kg) or control antibody (anti-KLH, 30 mg/kg) was injected (i.v.), in a volume of 200 µl on day 8 of the experiment. At the end of the experiment (day 14) mice were sacrificed by $CO_2$ inhalation and the synovial grafts were explanted. One of the grafts was snap-frozen in OCT compound (TissueTek, Sacura Finetek Europe) for further immunhistochemical analysis, and another one was frozen by immersion in liquid nitrogen for further RNA analysis.

Immunohistochemistry

5 µM cryosections on SuperFrost (Menzel GmbH, Braunschweig) slides were prepared using LEICA CM1900 cryostate and stored at −80° C. Thawed sections were fixed in acetone for 10 min, dried at room temperature and washed 3×5 min in PBS. All steps were performed at room temperature. Endogenous peroxidase activity was blocked by incubation with PBS supplemented with 0.3% hydrogen peroxide and 0.1% sodium azide for 20 min. Slides were washed 3×5 min in PBS and incubated with 10% normal human serum (NHS)/10% normal rabbit serum (NRbS) in PBS/1% BSA for 30 min. Next, primary antibody (mouse mAb) diluted in PBS supplemented with 1% BSA/10% NHS/10% NRbS was incubated for 60 min. After 3×2 min washes in PBS, HRP-conjugate (goat anti-mouse Ig-HRP; DAKO P0447) diluted 1:50 in PBS (supplemented with 1% BSA/10% NHS/10% NRbS) was added for 30 min. Peroxidase signal was enhanced using TSA™ Biotin system (Perkin Elmer Life Sciences, NEL700). Slides were washed 3×2 min in PBS and incubated with biotinyl tyramide diluted 1:1600 in amplification buffer for 30 min. After 3×2 min washes in PBS, streptavidin-HRP diluted 1:400 in PBS (supplemented with 1% BSA) was added for 30 min. Slides were washed 3×2 min in PBS and incubated with DAB solution (DAKO Cytomation K3465) for 5 min. Color reaction was stopped with distilled water. Finally, slides were counterstained with hematoxyline (MERCK), washed with running water and covered with Kaiser's glycerin and cover slips.

Scoring of Staining Intensity

Scoring of stained synovial tissue xenografts was performed in a blinded fashion by two trained persons. First the strongest section was selected from a series of sections and this reference section was awarded the maximum score 8. The staining intensity in the other sections was then scored on a scale of 0 to 8, relative to the reference section.

Statistical Analysis

Scoring of staining intensity was analyzed by Kruskal-Wallis one-way ANOVA followed by Dunn's multiple comparison test using Graph Pad Prism version 4.01 (Graph Pad software, Inc., San Diego, Calif., USA).

Figure 19:
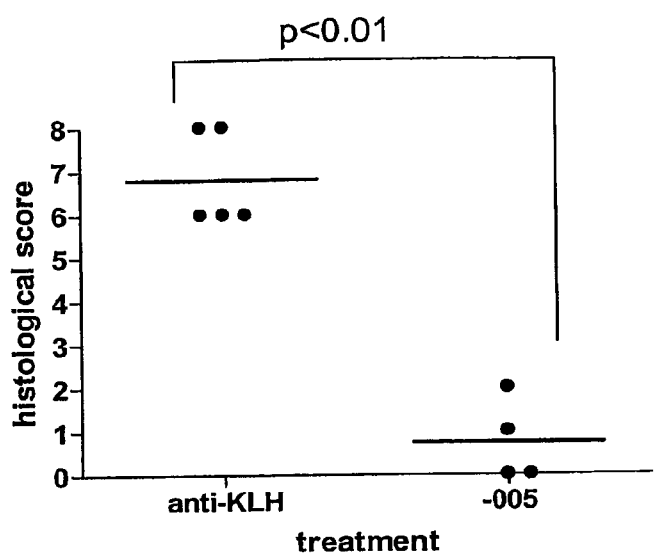
FIG. 19 shows the histological score for CD38-positive cells in implanted RA-SCID mouse xenografts on day 14, after treatment with anti-KLH (HuMab-KLH) or -005. Methods are described in Example 15.
Figure 20:
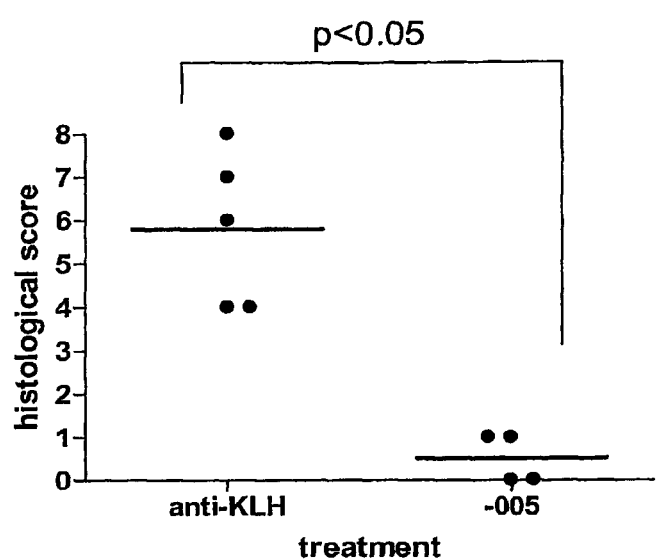
FIG. 20 shows the histological score for CD138-positive cells in implanted RA-SCID mouse xenografts on day 14, after treatment with anti-KLH or -005. Methods are described in Example 15.

FIG. 19 and FIG. 21 show that the numbers of anti-CD38-positive plasma cells are reduced after treatment with -005. Staining of plasma cells with anti-CD138 confirms that -005 results in reduced numbers of plasma cells (FIGS. 20 and 22).

Example 16

Sequencing of the Coding Sequence of Human Antibodies Against CD38

RNA Preparation

Total RNA was prepared from 5×10$^6$ cells of the hybridoma cell lines expressing the monoclonal antibody -003, -005 and -024, respectively, with the RNeasy kit (Qiagen, Westburg, Leusden, Netherlands) according to the manufacturer's protocol.

cDNA Preparation of -003, -005 and -024

5'-RACE-Complementary DNA (cDNA) of RNA was prepared from 100 ng total RNA, using the SMART RACE cDNA Amplification kit (Clontech), following the manufacturer's protocol.

Oligonucleotide primers were synthesized and quantified by Isogen Bioscience (Maarssen, The Netherlands). Primers were dissolved in $H_2O$ to 100 pmol/µl and stored at −20° C. A summary of all PCR and sequencing primers is tabulated (Table 5). For PCR, PfuTurbo® Hotstart DNA polymerase (Stratagene, Amsterdam, The Netherlands; product #600322) was used according to the manufacturer's instructions. Each reaction mix contained 200 µM mixed dNTPs (Roche Diagnostics, Almere, The Netherlands; product #1814362), 12 pmol of the reverse primer (RACEG1A1 for $V_H$3003-005, RACEV$_H$ApaI for $V_H$3003-003 and RACEV$_L$BsiWI for $V_L$3003-003 and 005), 7.2 pmol UPM-Mix (UPM-Mix: 2 µM ShortUPMH3 and 0.4 µM LongUPMH3), 0.6 µl of the 5'RACE cDNA template, and 1.5 unit of PfuTurbo® Hotstart DNA polymerase in PCR reaction buffer (supplied with polymerase) in a total volume of 30 µl. PCR reactions were carried out with a TGradient Thermocycler 96 (Whatman Biometra, Goettingen, Germany; product #050-801) using a 35-cycle program: denaturing at 95° C. for 2 min; 35 cycles of 95° C. for 30 sec, a 55° C. for 30 sec, and 72° C. for 1.5 min; final extension at 72° C. for 10 min. If appropriate, the PCR mixes were stored at 4° C. until further analysis or processing.

TABLE 5

Primers

| Name | Sequence |
|---|---|
| ShortUPMH3 | TGAAAGCTTCTAATACGACTCACTATAGGGC (SEQ ID NO: 35) |
| RACEV$_L$BsiWi | GAAGATGAAGACAGATGGTGCAGCCACCGTACG (SEQ ID NO: 36) |
| RACEV$_H$ApaI | GGAGGGTGCCAGGGGGAAGACCGATGGGCCCTT (SEQ ID NO: 37) |
| RACEG1A1 | GGGAGTAGAGTCCTGAGGACTG (SEQ ID NO: 38) |
| M13reverse | GGATAACAATTTCACACAGG (SEQ ID NO: 39) |
| LongUPMH3 | TGAAAGCTTCTAATACGACTCACTATAGGGCAAG CAGTGGTATCAACGCAGAGT (SEQ ID NO: 40) |
| HCseq5 | GGTCAGGGCGCCTGAGTTCCACG (SEQ ID NO: 41) |
| VH3003-003for | GATAAGCTTGCCGCCACCATGGACTGGACCTGGA GGTTCCTC (SEQ ID NO: 42) |
| VH3003-5for | GATAAGCTTGCCGCCACCATGGAGTTTGGGCTGA GCTGGCTT (SEQ ID NO: 43) |
| VL3003-5exfor | GATAAGCTTGCCGCCACCATGGAAGCCCCAGCTC AGCTTCTC (SEQ ID NO: 44) |
| VL3003-003for | GATAAGCTTGCCGCCACCATGAGGGTCCTCGCTC AGCTCCTG (SEQ ID NO: 45) |
| VH300324exfor | GATAAGCTTGCCGCCACCATGGGGTCAACCGCCA TCCTCGCC (SEQ ID NO: 46) |
| VL3003-24-5exfor | GATAAGCTTGCCGCCACCATGGAAGCCCCAGCTC AGCTTCTC (SEQ ID NO: 47) |

Cloning of -003-2F5 V$_H$ and V$_L$ and -005 V$_L$ and -024 V$_H$ and V$_L$ in pGEMT-Vector System II The reaction products were separated by electrophoresis on a 1% TAE agarose gel and stained with ethidium bromide. Bands of the correct size were cut from the gels and the DNA was isolated from the agarose using the QiaexII gel extraction kit (Qiagen, cat no 20021).

Gel isolated PCR fragments were A tailed by a 10 min 72° C. incubation with 200 µM dATP and 2.5 units Amplitaq (Perkin Elmer) and purified using minielute columns (Qiagen). A-tailed PCR fragments were cloned into the pGEMTeasy vector (Promega) using the pGEMT easy vector system II kit and protocol (LJ270, page 3/4). 2 µl of the ligation mixture was transformed into OneShot DH5αT1R competent *E. Coli* (Invitrogen) and plated on LB/Amp/IPTG/Xgal plates.

Sequencing

The V-regions -003 and -024 and the -005 V$_L$ region were sequenced by AGOWA (Berlin, Germany) after picking respectively 20 (V$_H$-003), 16 (V$_L$-003), 15 (V$_L$-005) and 6 (VH and VL -024) white colonies, isolating plasmid and sequencing with the M13 reverse primer. The -005 V$_H$ region was sequenced directly on the PCR product by using primer HCseq5. Sequences were analyzed using the Vector NTI advanced suite (Invitrogen).

Generation of Expression Vectors for Antibody -003, -005, -024 and Morphosys Antibody 3079

The V$_H$ coding region of -003 was amplified by PCR from a pGemT plasmid clone containing the V$_H$ region of -003, using the primers VH3003-003for and RACEVHApaI, introducing suitable restriction sites (HindIII and ApaI) for cloning into pConG1f0.4 (Lonza Biologics, Slough, UK) and an ideal Kozak sequence (GCCGCCACC). The pConG1f0.4 vector contains the heavy chain constant region of human IgG1. The V$_H$ PCR fragment was inserted, in frame, into the pConG1f0.4 vector using HindIII and ApaI. The construct was checked by sequence analysis.

The V$_H$ coding region of -005 was amplified by PCR from a pGemT plasmid clone containing the V$_H$ region of -005, using the primers VH3003-5for and RACEVHApaI, introducing suitable restriction sites (HindIII and ApaI) for cloning into pConG1f0.4 and an ideal Kozak sequence. The V$_H$ PCR fragment was inserted, in frame, into the pConG1f0.4 vector using HindIII and ApaI. The construct was checked by sequence analysis.

The V$_H$ coding region of -024 was amplified by PCR from a pGemT plasmid clone containing the V$_H$ region of -024, using the primers VH300324exfor and RACEVHApaI, introducing suitable restriction sites (HindIII and ApaI) for cloning into pConG1f0.4 and an ideal Kozak sequence. The V$_H$ PCR fragment was inserted, in frame, into the pConG1f0.4 vector using HindIII and ApaI. The construct was checked by sequence analysis.

The V$_H$ coding region of Morphosys antibody 3079 was synthesized by GeneArt (Regensburg, Germany), based on the data published in patent WO 2005/103083 A2. The coding region was codon optimized for expression in HEK cells to enhance expression levels and suitable restriction sites (HindIII and ApaI) for cloning into pConG1f0.4 and an ideal Kozak sequence were introduced. The plasmid containing the synthetic VH region was digested with ApaI and HindIII and the VH fragment was inserted, in frame, into the pConG1f0.4 vector.

The V$_L$ coding region of -005 was amplified by PCR from a pGemT plasmid clone containing the V$_L$ region of -005, using the primers VL3003-5exfor and RACEVLBsiWI, introducing suitable restriction sites (HindIII and Pfl23II) for cloning into pConKappa0.4 (Lonza Biologics) and an ideal Kozak sequence. The pConKappa0.4 vector contains the kappa light chain constant region. The V$_L$ PCR fragment was inserted, in frame, into the pConKappa0.4 vector using HindIII and Pfl23II. The construct was checked by sequence analysis.

The V$_L$ coding region of -003 was amplified by PCR from a pGemT plasmid clone containing the V$_L$ region of -003, using the primers VL3003-003for and RACEVLBsiWI, introducing suitable restriction sites (HindIII and Pfl23II) for cloning into pConKappa0.4 and an ideal Kozak sequence. The V$_L$ PCR fragment was inserted, in frame, into the pConKappa0.4 vector using HindIII and Pfl123II. The construct was checked by sequence analysis.

The V$_L$ coding region of -024 was amplified by PCR from a pGemT plasmid clone containing the V$_L$ region of -024, using the primers VL3003-24-5exfor and RACEVLBsiWI, introducing suitable restriction sites (HindIII and Pfl23II) for cloning into pConKappa0.4 and an ideal Kozak sequence. The V$_L$ PCR fragment was inserted, in frame, into the pConKappa0.4 vector using HindIII and Pfl23II. The construct was checked by sequence analysis.

The V$_L$ coding region of Morphosys antibody 3079 was synthesized by GeneArt, based on the data published in WO 2005/103083. The coding region was codon optimized for expression in HEK cells; to enhance expression levels and suitable restriction sites (HindIII and Pfl23II) for cloning into pConKappa0.4 and an ideal Kozak sequence were introduced. The plasmid, containing the synthetic V$_L$ region, was digested with Pfl23II and HindIII and the VH fragment was inserted, in frame, into the pConKappa0.4 vector.

Antibodies were transiently expressed in HEK-293F cells, as described in Example 17, by cotransfecting their heavy chain and light chain vectors.

Generation of Stable Cell Lines in CHO-K1SV Cells

For generation of stable cell lines, the heavy and light chain vectors of -003 or -005 were combined in a single double gene vector by standard cloning techniques.

The double gene vectors of -003 or -005 were linearized and transfected into CHO-K1SV (Lonza Biologics) cells, essentially as described by the manufacturer. Stable cell lines were selected by selection with 25 μM L-Methionine sulphoximine (MSX) as described by Lonza Biologics. Top producing clones were selected and propagated in CD-CHO (Invitrogen) medium and antibodies were purified from cell culture supernatant as described in Example 3.

Example 17

Epitope Mapping Using Site Directed Mutagenesis

Oligonucleotide primers were synthesized and quantified by Isogen Bioscience (Maarssen, The Netherlands). Primers were dissolved in $H_2O$ to 100 pmol/μl and stored at −20° C. A summary of all PCR and sequencing primers is shown in Table 6. For PCR, PfuTurbo® Hotstart DNA polymerase (Stratagene, Amsterdam, The Netherlands) was used according to the manufacturer's instructions. Each reaction mix contained 200 μM mixed dNTPs (Roche Diagnostics, Almere, The Netherlands), 10 pmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 μl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Agarose gel electrophoresis was performed according to Sambrook (Sambrook, Russell et al. 2000) using gels of 50 ml, in 1× Tris Acetate EDTA buffer. DNA was visualized by the inclusion of ethidium bromide in the gel and observation under UV light. Gel images were recorded by a CCD camera and an image analysis system (GeneGnome; Syngene, via Westburg B. V., Leusden, The Netherlands).

Purification of desired PCR fragments was carried out using a MinElute PCR Purification Kit (Qiagen, via Westburg, Leusden, The Netherlands; product #28006), according to the manufacturer's instructions. Isolated DNA was quantified by UV spectroscopy (see below) and the quality was assessed by agarose gel electrophoresis.

Alternatively, PCR or digestion products were separated by agarose gel electrophoresis (for instance when multiple fragments were present) using a 1% Tris Acetate EDTA agarose gel. The desired fragment was excised from the gel and recovered using the QIAEX II Gel Extraction Kit (Qiagen; product #20051), according to the manufacturer's instructions.

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one $OD_{260\,nm}$ unit=50 μg/ml). For all samples, the buffer in which the nucleic acids were dissolved was used as a reference.

Restriction enzymes and supplements were obtained from New England Biolabs (Beverly, Mass., USA) or Fermetas (Vilnius, Lithuania) and used according to the manufacturer's instructions. DNA (100 ng) was digested with 5 units of enzyme(s) in the appropriate buffer in a final volume of 10 μl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Ligations of DNA fragments were performed with the Quick Ligation Kit (New England Biolabs) according to the manufacturer's instructions. For each ligation, vector DNA was mixed with approximately three-fold molar excess of insert DNA.

Plasmid DNA (1-5 μl of DNA solution, typically 2 μl of DNA ligation mix) was transformed into One Shot DH5α-T1$^R$ E. coli cells (Invitrogen, Breda, The Netherlands; product #12297-016) using the heat-shock method, according to the manufacturer's instructions. Next, cells were plated on Luria-Bertani (LB) agar plates containing 50 μg/ml ampicillin. Plates were incubated for 16-18 h at 37° C. until bacterial colonies became evident.

Bacterial colonies were screened for the presence of vectors containing the desired sequences via colony PCR using the ThermoStart PCR Master Mix (Abgene, via Wetsburg, Leusden, The Netherlands; product #AB-938-DC15/b) and primers pConG1seq1 and pEE13.4seqrev2 (Table 6). Selected colonies were lightly touched with a 20 μl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Plasmid DNA was isolated from E. coli cultures using the following kits from Qiagen (via Westburg, Leusden, The Netherlands), according to the manufacturer's instructions. For bulk plasmid preparation (50-150 ml culture), either a HiSpeed Plasmid Maxi Kit (product #12663) or a HiSpeed Plasmid Midi Kit (product #12643) was used. For small scale plasmid preparation (±2 ml culture) a Qiaprep Spin Miniprep Kit (product #27106) was used and DNA was eluted in 50 μl elution buffer (supplied with kit).

Construction of HA-CD38 Expression Vector pEE13.4HACD38

The extracellular domain of human CD38 was amplified from plasmid pCIpuroCD38 (obtained from Prof. M. Glennie, Tenovus Research Laboratory, Southampton General Hospital, Southampton, UK) using primers cd38forha and cd38exrev. By this PCR reaction an HA-tag was introduced. This PCR product was used as template for a second PCR reaction with primers SPHMM38ex and cd38exrev. By this PCR reaction, signal peptide SPHMM, restriction sites and an ideal Kozak sequence (GCCGCCACC) for optimal expression were introduced. After purification, this PCR fragment was cloned into expression vector pEE13.4 (Lonza Biologics) and the complete coding sequence was confirmed by sequencing with primers pConKseq1, pEE13.4seqrev, cd38seq1for and cd38seq2rev (Table 6). This construct was named pEE13.4HACD38

Site-directed Mutagenesis

Three single mutant proteins of huCD38 was constructed, in which T was mutated to A at position 237 (T237A, SEQ ID No:32), Q was mutated to R at position 272 (Q272R, SEQ ID No:33), or S was mutated to F at position 274 (S274F, SEQ ID No:34). Site-directed mutagenesis was performed using the QuickChange II XL Site-Directed Mutagenesis Kit (Stratagene, Amsterdam, The Netherlands) according to the manufacturer's instructions. This method included the introduction of a silent extra restriction site or loss of a restriction site to screen for successful mutagenesis (extra Xba1 site for T237A mutant, extra Bcg1 site for Q272R mutant and loss of Ssp1 site for S274F mutant). Briefly, 5 μl 10× reaction buffer, 1 μl oligonucleotide HACD38T237Afor2, HACD38Q272Rfor or HACD38S274Ffor (100 pmol/µl), 1 µl oligonucleotide HACD38T237Arev2, HACD38Q272Rrev or HACD38S274Frev (100 pmol/µl), 1 µl dNTP mix, 3 µl Quicksolution, 1 µl plasmid pEE13.4HACD38 (50 ng/µl) and 1 µl PfuUltra HF DNA polymerase were mixed in a total volume of 50 µl and amplified with a TGradient Thermocycler 96 (Whatman Biometra, Goettingen, Germany; product #050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 µl DpnI for 60 min at 37° C. to digest the pEE13.4HACD38 WT vector and stored at 4° C. until further processing. The reaction mixture was precipitated with 5 µl 3 M NaAc and 125 µl ethanol, incubated for 20 minutes at –20° C. and spun down for 20 minutes at 4° C. at 14000×g. The DNA pellet was washed with 70% ethanol, dried and dissolved in 4 µl water. The total 4 µl reaction volume was transformed in One Shot Top 10DH5α T1$^R$ competent *E. coli* cells (Invitrogen, Breda, The Netherlands) according to the manufacturer's instructions (Invitrogen). Next, cells were plated on Luria-Bertani (LB) agar plates containing 50 µg/ml ampicillin. Plates were incubated for 16-18 h at 37° C. until bacterial colonies became evident. Colonies were screened by colony PCR using primers pConG1seq1 and pEE13.4seqrev2 (Table 5) and digested with the relevant restriction enzymes to screen for incorporation of the mutagenic oligonucleotide. 2 positive clones for each mutant were grown and plasmid DNA was isolated. The complete HACD38 coding sequence was determined using primers cd38seq1for, pConG1seq1 and pEE13.4seqrev2 to confirm the presence of the mutations and the absence of additional undesirable mutations.

DNA Sequencing

Plasmid DNA samples were sent to AGOWA (Berlin, Germany) for sequence analysis. Sequences were analyzed using Vector NTI advanced software (Informax, Oxford, UK).

Transient Expression in HEK-293F Cells

Freestyle™ 293-F (a HEK-293 subclone adapted to suspension growth and chemically defined Freestyle medium, (HEK-293F)) cells were obtained from Invitrogen and transfected with pEE13.4HACD38 and with the three constructs carrying the mutations T237A, Q272R and S274F, according to the manufacturer's protocol using 293fectin (Invitrogen). Culture supernatants of transfected cells were used in ELISA for anti-CD38 binding studies.

Anti-CD38 Antibody Binding

ELISA plates (Greiner, #655092) were coated O/N at 4° C. with 1 µg anti-HA antibody (Sigma, #H-9658) and subsequently blocked with 2% chicken serum. Culture supernatants of transfected HEK293F cells were diluted, applied to the ELISA plates and incubated for 1 hr at RT. After washing, serial dilutions of HuMabs -003 and -005 were added and incubated for 1 hr at RT. Bound antibodies were detected with HRP-conjugated goat-anti-human IgG antibodies. The assay was developed with ABTS (Roche, #1112597) and the absorbance was measured at 405 nm using a spectrophotometer.

As can been seen from FIGS. 23A-23C, both -003 and -005 bind to wt human CD38. The binding of -003 was not affected by the introduction of mutations T237A (FIG. 23A), Q272R (FIG. 23B) or S274F (FIG. 23C). -005 was able to bind CD38 harboring mutation T237A (FIG. 23A). Binding of -005 to CD38 with mutation Q272R was severely affected (FIG. 23B), both with respect to $EC_{50}$ and maximum binding capacity. -005 was not able to bind to mutant CD38 wherein serine at position 274 was replaced by phenylalanine (FIG. 23C).

These data shows that -003 and -005 bind to different epitopes. Furthermore these studies revealed that binding of -005 to CD38 is sensitive to mutations at positions 272 and 274. Particularly S274 is essential for -005 binding to CD38.

TABLE 6

| Primers | |
|---|---|
| Name | Sequence |
| cd38forha | CTGCTGTGGCCCATGGTGTGGGCCTACCCTTACG ACGTGCCTGACTACGCCAGGTGGCGCCAGACGTG GAGC (SEQ ID NO: 48) |
| cd38exrev | AGGTCAGGTACCTCAGATCTCAGATGTGCAAG (SEQ ID NO: 49) |
| SPHMM38ex | TATAGCCCGGGGCCGCCACCATGTGGTGGCGCCT GTGGTGGCTGCTGCTGCTGCTGCTGCTGCTGTGG CCCATGGTGTGGGCC (SEQ ID NO: 50) |
| pConG1seq1 | GAAGACTTAAGGCAGCGGCAGAA (SEQ ID NO: 51) |
| pConKseq1 | GTAGTCTGAGCAGTACTCGTTGC (SEQ ID NO: 52) |
| pEE13.4seqrev | TGCATTCATTTTATGTTTCAGGT (SEQ ID NO: 53) |
| pEE13.4seqrev2 | TCGGACATCTCATGACTTTCTTT (SEQ ID NO: 54) |
| cd38seq1for | AGGACACGCTGCTAGGCTACCTT (SEQ ID NO: 55) |
| cd38seq2rev | GTCCTTTCTCCAGTCTGGGCAAG (SEQ ID NO: 56) |
| HACD38T237Arev2 | TCCACCATGTATCACCCAGGCCTCTAGAGCCTGA ACCTTCTCTGGTTG (SEQ ID NO: 57) |
| HACD38T237Afor2 | CAACCAGAGAAGGTTCAGGCTCTAGAGGCCTGGG TGATACATGGTGGA (SEQ ID NO: 58) |
| HACD38Q272Rrev | GATATTCTTGCAGGAAAATCGAATATTCCTTTTG CTTAT (SEQ ID NO: 59) |
| HACD38Q272Rfor | ATAAGCAAAAGGAATATTCGATTTTCCTGCAAGA ATATC (SEQ ID NO: 60) |
| HACD38S274Frev | TCTGTAGATATTCTTGCAGAAAAATTGAATGTTC CTTTTGCTTATA (SEQ ID NO: 61) |
| HACD38S274Ffor | TATAAGCAAAAGGAACATTCAATTTTTCTGCAAG AATATCTACAGA (SEQ ID NO: 62) |

Example 18

Induction of Proliferation of PBMC

-003, -005 and -024 were tested in an assay essentially as described in Ausiello et al., Tissue antigens 56, 538-547 (2000). Briefly, PBMCs from healthy donors were cultured at $1\times10^5$ cells/well in flat bottom 96-well plates in the presence of antibodies (final concentration: 1.1-3.3-10-30 μg/ml) in 200 μl $RPMI^{++}$. Stimulation of cells with IL-15 (at 333 ng/ml; Amgen Inc., Thousand Oaks, Calif., USA) was used as positive control. After a 4 day incubation at 37° C., 30 μl $^3$H-thymidine (16.7 μCi/ml) was added, and culture was continued O/N. $^3$H-thymidine incorporation was assessed using a Packard Cobra gamma counter (Packard Instruments, Meriden, DT, USA), according to the manufacturer's instructions. Data are shown as the mean cpm (±SEM) of PBMCs obtained from 10 donors. The results show that -003 and -005 do not induce significant proliferation of PBMCs (FIG. 24A). Also -024 did not induce significant proliferation of PBMCs (data not shown).

Example 19

Induction of IL-6

-003, -005 and -024 were tested in an assay as described in Ausiello et al., Tissue antigens 56, 538-547 (2000). Briefly, PBMCs were cultured at 1×10⁶ cells/well in 48-well plates in the presence of 20 µg/ml of antibodies and 10 ng/ml LPS (Sigma-Aldrich Chemie, Zwijndrecht, The Netherlands) in 500 µl RPMI⁺⁺. After an O/N incubation at 37° C., supernatant was harvested and stored at −20° C. The IL-6 concentration was assessed by ELISA (IL-6 ELISA kit, U-CyTech Biosciences, Utrecht, The Netherlands) according to the manufacturer's instructions. Data are shown mean concentration in pg/ml (±SEM) from 7 donors. The results show that -003 and -005 does not induce release of significant IL-6 levels (FIG. 24B). Also -024 did not induce release of significant IL-6 levels (data not shown).

Example 20

Induction of Release of IFN-γ

-003, -005 and -024 were tested in an assay as described in Ausiello et al., Tissue antigens 56, 538-547 (2000). Briefly, PBMCs were cultured at 1×10⁶ cells/well in 48-well plates in the presence of 20 µg/ml of antibodies and 1 µg/ml OKT-3 (Sanquin, Amsterdam, The Netherlands) in 500 µl RPMI⁺⁺. After an O/N incubation at 37° C., supernatant was harvested and stored at −20° C. The IFN-γ concentration was assessed by ELISA (IFN-γ ELISA kit, U-CyTech Biosciences, Utrecht, The Netherlands) according to the manufacturer's instructions. Data are shown mean concentration in pg/ml (±SEM) from 9 donors. The results show that -003 and -005 does not induce release of detectable IFN-γ levels (FIG. 24C). Also -024 did not induce release of significant IFN-γ levels (data not shown).

Example 21

Affinity of Binding of -003 and -005 to Recombinant CD38

Binding of -003 and -005 to CD38 was tested using surface plasmon resonance. Briefly, purified antibodies were immobilized on a CM-5 sensor chip (Biacore, Uppsala, Sweden) via anime coupling. HA-tagged CD38 (see Example 3) was flowed over, and the binding of antigen to mAb was detected by a change in refractive index at the surface of the chip using a Biacore 3000 (Biacore). The associated and rate constants for -003 (Table 7) and -005 (Table 8) are summarized below, mean of 3 experiments±SD, and show that both -003 and -005 have a high affinity for CD38.

TABLE 7

Association and rate constants at 25° C.

| | -003 |
|---|---|
| $k_a$ (1/Ms) | $2.17 \times 10^5 \pm 2.65 \times 10^4$ |
| $k_d$ (1/s) | $1.9 \times 10^{-4} \pm 4.51 \times 10^{-6}$ |
| $K_A$ (1/M) | $1.14 \times 10^9 \pm 1.58 \times 10^8$ |
| $K_D$ (M) | $8.85 \times 10^{-10} \pm 1.2 \times 10^{-10}$ |

TABLE 8

Association and rate constants at 25° C.

| | -005 |
|---|---|
| $k_a$ (1/Ms) | $8.88 \times 10^4 \pm 1.95 \times 10^4$ |
| $k_d$ (1/s) | $5.22 \times 10^{-4} \pm 1.16 \times 10^{-5}$ |

TABLE 8-continued

Association and rate constants at 25° C.

| | -005 |
|---|---|
| $K_A$ (1/M) | $1.7 \times 10^8 \pm 3.68 \times 10^7$ |
| $K_D$ (M) | $6.06 \times 10^{-9} \pm 1.21 \times 10^{-9}$ |

Example 22

Epitope Mapping

Epitope Mapping Using PEPSCAN Method

According to known procedures (Geysen et al. 1984. Use of peptide synthesis to probe viral antigens for epitopes to a resolution of a single amino acid. Proc Natl Acad Sci USA 81:3998; Slootstra et al. 1996. Structural aspects of antibody-antigen interaction revealed through small random peptide libraries. Mol Divers 1:87; Puijk et al. 2001. Segment synthesis. In PCT, The Netherlands, p. 1.), overlapping 20-mer linear and 15-mer looped peptides were synthesized covering 138 amino acids at the C-terminus of human CD38. Furthermore, based on the sequence at the C-terminus single-looped peptides of different size were made covering region KNIYR-PDKFLQCVKNPEDSSCTSEI (SEQ ID NO: 63), region CVHNLQPEKVQTLEAWVIHGG (SEQ ID NO: 64), and region CLESIISKRNIQFSAKNIYRC (SEQ ID NO: 65). In addition, extra sets were designed to reconstruct double-looped regions that were composed of SKRNIQFSCKNIYR (SEQ ID NO: 66) and EKVQTLEAWVIHGG (SEQ ID NO: 67). Native cysteines were replaced by alanines. Peptides were screened in an ELISA-assay using credit-card format mini-PEPSCAN cards.

Synthesis of Peptides

The peptides were synthesized using standard Fmoc-chemistry and deprotected using TFA with scavengers. Subsequently, the deprotected peptides were reacted on the microarray with an 0.5 mM solution of 2,6-bis(bromomethyl) pyridine or 2,4,6-tris(bromomethyl)mesitylene in ammonium bicarbonate (20 mM, pH 7.9), supplemented with acetonitrile (1:1 [volume/volume]). The microarrays were gently shaken in the solution for 30-60 min, while completely covered in the solution. Finally, the microarrays were washed extensively with excess of Millipore $H_2O$ and sonicated in disrupt-buffer containing 1% sodium dodecylsulfate, 0.1% β-mercaptoethanol, in PBS (pH 7.2) at 70° C. for 30 min, followed by sonication in millipore $H_2O$ for another 45 min.

PEPSCAN ELISA-Assay

The 455-well credit card-format polyethylene cards, containing the covalently linked peptides, were incubated with serum (e.g. diluted 1:1000 in blocking solution which contains 5% horse serum [volume/volume] and 5% ovalbumin [weight/volume]) (4° C., overnight). After washing, the peptides were incubated with rabbit-anti-human Ig peroxidase (dilution 1:1000, 25° C., 1 hour), and after washing the peroxidase substrate (2,2'-azino-di-3-ethylbenzthiazoline sulfonate and 2 µl/ml 3% $H_2O_2$) was added. After one hour, the color development was measured with a CCD-camera and an image processing system. The set up consists of a CCD-camera with a 55 mm lens (Sony CCD Video Camera XC-77RR, Nikon micro-nikkor 55 mm f/2.8 lens), a camera adaptor (Sony Camera adaptor DC-77RR) and the Image Processing Software package Optimas, version 6.5 (Media Cybernetics, Silver Spring, Md. 20910, U.S.A.; Optimas runs on a pentium II computer system).

Method for Epitope Representation

Individual amino acids were identified by dipeptide motifs which represent the smallest unique units in the human CD38 amino acid sequence. All dipeptide motifs present in each of the 1164 peptides tested were awarded the ELISA value obtained for the respective whole peptide. To rank the dipeptide motifs from strong to poor binding, a relative signal was calculated by dividing the ELISA value obtained for each individual motif by the average ELISA value from all 1164 tested linear and looped peptides, and these were sorted for decreasing values. In this manner, amino acid contributions to conformational epitopes were considered. For each of the mAb tested, all dipeptide motifs scoring above 2.5 (i.e. ELISA values of peptides containing these motifs were at least 2.5 times the average ELISA value of those obtained with all 1164 peptides) were selected. The data were deconvoluted into single amino acid contributions represented on the linear CD38 sequence by a scoring system. By walking along the linear CD38 sequence and by using the unique dipeptide units as a reference point, one point was awarded each time a CD38 amino acid was present in this set of high scoring peptides.

-003, -005 and -024 were all found to bind to the regions SKRNIQFSCKNIYR and EKVQTLEAWVIHGG of human CD38. -003 especially recognized the motifs RNIQF (SEQ ID NO: 68) and WVIH (SEQ ID NO: 69), -005 especially recognized the motifs KRN (SEQ ID NO: 70) and VQTL (SEQ ID NO: 71).

Example 23

Enzymatic Activity

The enzymatic activity of human CD38 was measured in an assay essentially as described in Graeff et al., J. Biol. Chem. 269, 30260-30267 (1994). Briefly, substrate NGD$^+$ (80 µM) was incubated with CD38 (0.6 µg/ml His-tagged extracellular domain of human CD38, see Example 3 regarding purification of His-CD38) in a buffer containing 20 mM Tris-HCl, pH 7.0. The production of cGDPR can be monitored spectrophotometrically at the emission wavelength of 410 nm (excitation at 300 nm). In this example an excitation filter of 340±60 nm and an emission filter of 430±8 nm was used.

To test the effect of -003, -005 and -024 on the enzymatic activity of CD38, recombinant His-CD38 protein was pre-incubated for 15 min at room temperature with various concentrations (30, 3, 0.3 and 0.03 µg/ml) of the different antibodies before adding the substrate NGD$^+$. The production of cyclic GDP-ribose (cGDPR) was recorded at different time points after addition of antibodies (3, 6, 9, 12, 30, 45, 60, 75 and 90 min).

FIG. 25B shows that -005 has a pronounced inhibitory effect on the production of cGDPR. After 90 minutes, addition of 30 and 3 µg/ml -005 resulted in a 32% and 34% reduced production of cGDPR (Table 9). Similar results were observed in independent experiments using different batches of -005.

No inhibitory effect on cGPDR production was observed after addition of -003 (FIG. 25B, Table 9), -024 (FIG. 25D, Table 9) or anti-KLH (FIG. 25A, Table 9).

Based on these findings -005 is also expected to inhibit the synthesis of Cyclic ADP-ribose (cADPR) from NAD$^+$. Inhibition of the synthesis of cADPR can be determined according to the HPLC method described in Munshi et al., J. Biol. Chem. 275, 21566-21571 (2000).

TABLE 9 cGDPribose production in presence of CD38-specific antibodies or anti-KLH.

| | Production (% of NGD control) | | | |
|---|---|---|---|---|
| | 30 µg/ml | 3 µg/ml | 0.3 µg/ml | 0.03 µg/ml |
| KLH | 110 | 99 | 108 | 111 |
| -003 | 99 | 100 | 107 | 107 |

TABLE 9-continued cGDPribose production in presence of CD38-specific antibodies or anti-KLH.

| | Production (% of NGD control) | | | |
|---|---|---|---|---|
| | 30 µg/ml | 3 µg/ml | 0.3 µg/ml | 0.03 µg/ml |
| -005 | 68 | 66 | 98 | 102 |
| -024 | 99 | 100 | 104 | 105 |

Example 24

Comparison of -003 and -005 with Morphosys Antibody 3079.

Antibodies -003 and -005 were functionally compared to Morphosys antibody 3079 (TH-3079). Methods for cloning and expression of Morphosys antibody TH-3079 are described in Example 16. Methods for CDC are described in Example 6. Methods for ADCC are described in Example 5. FIG. 26A shows that -005 and -003 and TH-3079 induce CDC-mediated lysis of CD38-transfected CHO cells, with similar maximal lysis. When $EC_{50}$ values are compared, -005 antibody is better than TH3079 in inducing lysis of CHO-CD38 cells, with 2-times lower $EC_{50}$ (see Table 10).

FIG. 26B shows that -005 is superior to TH-3079 in inducing CDC-mediated lysis of Daudi-luciferase cells, with maximal lysis by -005 being 2-3 times higher than by TH3079. When $EC_{50}$ values are compared, -005 antibody is similar to TH-3079 in inducing lysis of Daudi-luciferase cells (see Table 10). -003 does not induce significant CDC-mediated lysis of Daudi-luciferase cells.

FIG. 26C shows that in this experiment -005, -003 and TH-3079 mediate lysis of Daudi target cells via ADCC. No difference was found in (log) $EC_{50}$ and maximal lysis (Table 11, n=5).

TABLE 10

Maximal lysis and EC50 values of CD38-specific antibodies in CDC.

| | CHO-CD38 cells (n = 2) | | Daudi-luc cells (n = 2) | |
|---|---|---|---|---|
| | EC50 µg/ml | % Max. lysis | EC50 µg/ml | % Max. lysis |
| -005 | 0.15 ± 0.007 | 76.5 ± 3.54 | 0.39 ± 0.00 | 70.5 ± 7.78 |
| TH-3079 | 0.31 ± 0.021 | 81.5 ± 7.78 | 0.34 ± 0.26 | 25.5 ± 12.02 |
| -003 | 4.5 ± 0.933 | 62.0 ± 16.79 | nc | 12 ± 8.49 |

TABLE 11

Maximal lysis and $EC_{50}$ values of CD38 specific antibodies in ADCC.

| | Log EC50 | STD log EC50 | Maximal lysis (%) | STD max. lysis |
|---|---|---|---|---|
| -005 | 0.76 | 0.18 | 49.2 | 12.8 |
| -003 | 1.17 | 0.23 | 64 | 14.2 |
| TH3079 | 0.96 | 0.10 | 43.8 | 12.0 |

Example 25

Inhibition of Cellular Expressed CD38 Enzymatic Activity

The enzymatic activity of cellular expressed human CD38 was measured in an assay essentially as described in Graeff et al., J. Biol. Chem. 269, 30260-30267 (1994). Briefly, substrate NGD (80 µM) was incubated with 10$^5$ CHO cells transfected with human CD38 (CHO-CD38 cells) in a buffer containing 20 mM Tris-HCl, pH 7.0 supplemented with 30 µg/ml IgG1. The production of cGDPR can be monitored spectrophotometrically at the emission wavelength of 410 nm (excitation at 300 nm). In this example an excitation filter of 340±60 nm and an emission filter of 430±8 nm was used.

To test the effect of -005 and -003 on the enzymatic activity of cellular expressed CD38, CHO-CD38 cells were pre-incubated for 15' at room temp. with various concentrations (30, 3, 0.3 and 0.03 μg/ml) of the different antibodies before adding the substrate NGD. The production of cGDPR was recorded at different time points after addition of substrate NGD (3, 6, 9, 12, 30, 45, 60, 112 and 156 min).

After 156 minutes, addition of 30 and 3 μg/ml -005 resulted in a 21% and 18% reduced production of cGDPR. No inhibitory effect on cGPDR production was observed after addition of -003 or IgG1 control antibody (Table 12).

TABLE 12 cGDPribose production in presence of CD38-specific antibodies or IgG1 control.

| | Production (% of NGD control) | | | |
|---|---|---|---|---|
| | 30 μg/ml | 3 μg/ml | 0.3 μg/ml | 0.03 μg/ml |
| IgG1 control | 104 | 105 | 103 | 104 |
| −003 | 107 | 106 | 107 | 105 |
| −005 | 79 | 82 | 100 | 104 |

Example 26

Binding of Antibody -005 to EBV Transformed Chimpanzee B Cells

Figure 27:
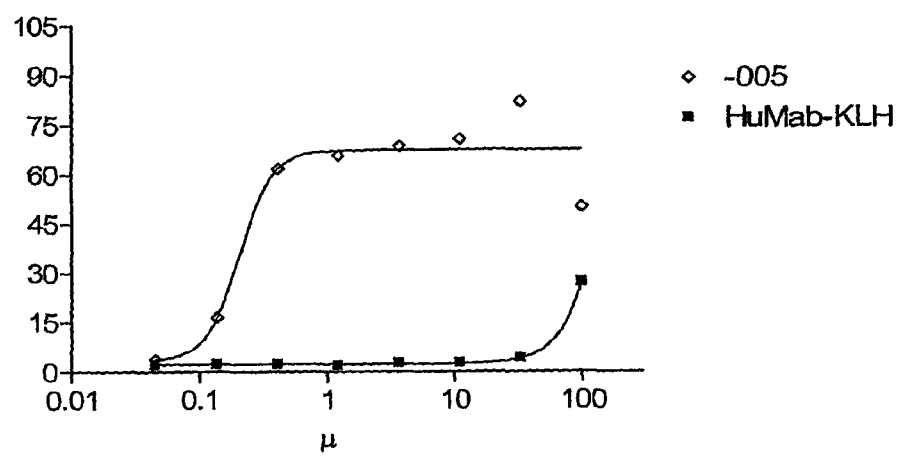
FIG. 27 shows the binding of -005 and the isotype control antibody HuMab-KLH to EBV transformed chimpanzee B cells as measured by flow cytometry. The experimental setup is described in Example 26.

After harvesting and counting, EBV transformed chimpanzee B cells (received from Biomedical Primate Research Centre, Department Immunobiology, Rijswijk, The Netherlands) were resuspended ($1 \times 10^6$ cells/ml) in PBS-BSA (PBS supplemented with 0.1% BSA and 0.02% Na-azide). Then, cells were put in 96-well V-bottom plates (100 μl/well) and washed twice in PBS-BSA. Thereafter, 50 μl FITC-labeled -005 antibody solution in PBS-BSA was added to the cells (4° C., 30 min). Cells were washed three times and specific binding of -005 to EBV transformed chimpanzee B cells was detected by flow cytometry. FITC labeled HuMab-KLH (a human monoclonal antibody against KLH (keyhole limpet haemocyanin) generated by Genmab B. V., Utrecht, The Netherlands by use of the immunization protocols described elsewhere herein) was used as a control. FIG. 27 shows dose dependent binding of -005 to EBV transformed chimpanzee B cells. No dose dependent binding to EBV transformed chimpanzee B cells was observed with the control antibody HuMab-KLH.

Example 27

In Vitro Combination Therapy of Antibody -005 with Dexamethasone and Bortezomib

Antibody -005 was tested for its capacity to induce cell death of the multiple myeloma cell line UM6 in vitro in a triple combination setting with Dexamethasone (Dex) and Bortezomib (Bor; Velcade®). Outcome of the triple treatment was compared to single drug treatments and double combo treatments.

$3 \times 10^5$ UM6 cells were incubated overnight at 37° C. with medium alone, with Dex (20 μM), with Bor (15 pM) or with the combination of Bor and Dex. After 23 hours, -005 (10 μg/ml) was added; and 15 minutes after that, normal human serum was added and samples were incubated for another 45 minutes at 37° C. Finally, 10 μl propidium iodide (PI; Sigma-Aldrich Chemie B.V.; 10 μg/ml) was added, and cell lysis was detected by flow cytometry using a FACS Calibur™ (Becton Dickinson) by measurement of the percentage of PI-positive cells.

Figure 28:
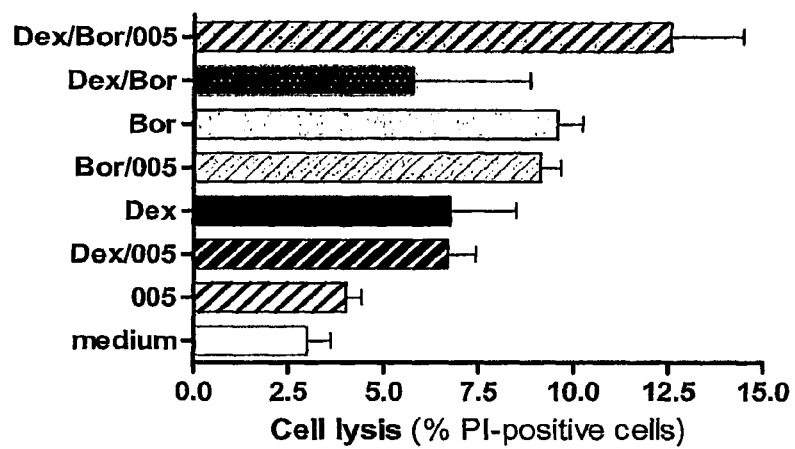
FIG. 28 shows the capacity of -005 alone and in combination with other compounds (Dexamethasone (Dex) and Bortezomib (Bor)) to induce cell death of the multiple myeloma cell line UM6 in vitro.

As can be seen in FIG. 28, the triple treatment exceeded lysis observed with any of the single or double combination treatments. This effect was observed in two independent experiments.

Example 28

Patients with a clinical diagnosis of multiple myeloma are treated with a combination of anti-CD38 antibody -005, melphalan and prednisone.

The compounds are administered to the patients according to the following dosing schedule:

| | |
|---|---|
| antibody −005: | 8 mg/kg administered once weekly for 4 weeks (IV) |
| melphalan: | 0.2 mg/kg per day IV for 4 days every 4-6 weeks |
| prednisone: | 2 mg/kg PO for 4 days every 4-6 weeks |

Response is determined by decrease in M-protein in serum, decrease in number of plasma cells in bone marrow and decrease in Benze-Jones protein in urine and reduction of/absence of new osteolytic bone lesions.

Example 29

Patients with a clinical diagnosis of multiple myeloma are treated with a combination of anti-CD38 antibody -005, thalidomide and dexamethasone.

The compounds are administered to the patients according to the following dosing schedule:

| | |
|---|---|
| antibody −005: | 8 mg/kg administered once weekly for 4 weeks (IV) |
| thalidomide: | 200 mg/day (PO) |
| dexamethasone: | 40 mg/day on day 1-4, 9-12 and 17-20 of each 28 day cycle (PO) |

Response is determined by decrease in M-protein in serum, decrease in number of plasma cells in bone marrow and decrease in Benze-Jones protein in urine and reduction of/absence of new osteolytic bone lesions.

Example 30

Patients with a clinical diagnosis of multiple myeloma are treated with a combination of anti-CD38 antibody -005, lenalidomide and dexamethasone.

The compounds are administered to the patients according to the following dosing schedule:

| | |
|---|---|
| antibody −005: | 8 mg/kg administered once weekly for 4 weeks (IV) |
| lenalidomide: | 25 mg/day (PO) |
| dexamethasone: | 40 mg/day on day 1-4, 9-12 and 17-20 of each 28 day cycle (PO) |

Response is determined by decrease in M-protein in serum, decrease in number of plasma cells in bone marrow and decrease in Benze-Jones protein in urine and reduction of/absence of new osteolytic bone lesions.

Example 31

Patients with a clinical diagnosis of multiple myeloma are treated with a combination of anti-CD38 antibody -005, bortezomib and dexamethasone.

The compounds are administered to the patients according to the following dosing schedule:

| | |
|---|---|
| antibody –005: | 8 mg/kg administered once weekly for 4 weeks (IV) |
| bortezomib: | 1.3 mg/m2 on days 1, 4, 6 and 11, every 21 day cycle (IV) |
| dexamethasone: | 40 mg/day on day 1-4, 9-12 and 17-20 of each 28 day cycle (PO) |

Response is determined by decrease in M-protein in serum, decrease in number of plasma cells in bone marrow and decrease in Benze-Jones protein in urine and reduction of/absence of new osteolytic bone lesions.

The invention claimed is:

1. A method for inhibiting growth and/or proliferation of multiple myeloma cells in an individual in need thereof, comprising administering to the individual i) an antibody that binds to residues KRN (SEQ ID NO: 70), corresponding to amino acid residues 268-270 of human CD38 (SEQ ID NO: 31), and residues VQTL (SEQ ID NO: 71), corresponding to amino acid residues 235-238 of human CD38 (SEQ ID NO: 31), ii) at least one corticosteroid, and iii) at least one non-corticosteroid chemotherapeutic agent.

2. The method of claim 1, further comprising administering autologous peripheral stem cells or bone marrow to the patient.

3. The method of claim 1, wherein said at least one non-corticosteroid chemotherapeutic agent comprises a cytotoxic agent or an angiogenesis inhibitor.

4. The method of claim 1, wherein said at least one non-corticosteroid chemotherapeutic agent comprises an alkylating agent.

5. The method of claim 1, wherein said at least one non-corticosteroid chemotherapeutic agent comprises one or more agents selected from the group consisting of: melphalan, mechlorethamine, thioepa, chlorambucil, carmustine (BSNU), lomustine (CCNU), cyclophosphamide, busulfan, dibromomannitol, streptozotocin, dacarbazine (DTIC), procarbazine, mitomycin C, cisplatin and other platinum derivatives.

6. The method of claim 1, wherein said at least one non-corticosteroid chemotherapeutic agent comprises a glutamic acid derivative.

7. The method of claim 1, wherein said at least one non-corticosteroid chemotherapeutic agent comprises a proteasome inhibitor.

8. The method of claim 1, wherein said at least one non-corticosteroid chemotherapeutic agent comprises a vinca alkaloid.

9. The method of claim 1 wherein said at least one non-corticosteroid chemotherapeutic agent comprises an anthracycline.

10. The method of claim 1, wherein said at least one corticosteroid comprises a glucocorticoid.

11. The method of claim 1, wherein said at least one corticosteroid comprises prednisone.

12. The method of claim 1, wherein said at least one corticosteroid comprises prednisone and said at least one non-corticosteroid chemotherapeutic agent comprises melphalan.

13. The method of claim 1, wherein said at least one corticosteroid comprises prednisone and said at least one non-corticosteroid chemotherapeutic agent comprises thalidomide.

14. The method of claim 1, wherein said at least one corticosteroid comprises prednisone and said at least one non-corticosteroid chemotherapeutic agent comprises melphalan and thalidomide.

15. The method of claim 1, wherein said at least one corticosteroid comprises dexamethasone.

16. The method of claim 1, wherein said at least one corticosteroid comprises dexamethasone and said at least one non-corticosteroid chemotherapeutic agent comprises thalidomide or lenalidomide.

17. The method of claim 1, wherein said at least one corticosteroid comprises dexamethasone and said at least one non-corticosteroid chemotherapeutic agent comprises vincristine or doxorubicin.

18. The method of claim 1, comprising the further administration of interferon-alpha.

19. The method of claim 1, wherein said antibody is a monoclonal antibody.

20. The method of claim 1, wherein said antibody is a human monoclonal antibody.

21. The method of claim 1, wherein said antibody does not induce release of significant IL-6 by human monocytes or peripheral blood mononuclear cells.

22. The method of claim 1, wherein said antibody does not induce release of detectable IFN-γ by human T cells or peripheral blood mononuclear cells.

23. The method of claim 1, wherein said antibody is internalized by CD38 expressing cells.

24. The method of claim 1, wherein said antibody induces ADCC of CD38 expressing cells.

25. The method of claim 1, wherein said antibody induces CDC of CD38 expressing cells in the presence of complement.

26. The method of claim 1, wherein said antibody inhibits the synthesis of cGDPR.

27. The method of claim 1, wherein said antibody inhibits the synthesis of cADPR.

28. The method of claim 1, wherein said antibody comprises heavy and light chain CDR sequences set forth in SEQ ID NOs: 13-15 and 18-20, respectively.

29. The method of claim 28, wherein said antibody comprises heavy and light chain variable regions having the amino acid sequences set forth in SEQ ID No:12 and 17, respectively.

30. The method of claim 1, wherein said antibody is a full length IgG1, IgG2, IgG3, IgG4, IgD, IgA, IgE, or IgM antibody.

31. The method of claim 1, wherein said antibody is an antibody fragment or a single-chain antibody.

32. The method of claim 1, wherein said antibody is conjugated to a cytotoxic agent, a radioisotope, or a drug.

33. The method of claim 1, wherein said antibody is a bispecific or multispecific molecule comprising a binding specificity for a human effector cell.

34. The method of claim 1, wherein said antibody is a bispecific or multispecific molecule comprising a binding specificity for CD3, CD4, CD138, IL-15R, membrane bound or receptor bound TNF-γ, a human Fc receptor, or membrane bound or receptor bound IL-15.

35. The method of claim 1, wherein said tumor cells are recurrent or refractory tumor cells.

36. The method of claim 1, wherein said individual has not responded to a previous anti-cancer treatment for the same cancer.

37. The method of claim 1, wherein said individual is enrolled to undergo subsequent autologous peripheral stem cell or bone marrow transplantation.

38. The method of claim 1, wherein the antibody, at least one corticosteroid and at least one non-corticosteroid chemotherapeutic agent are administered simultaneously.

39. The method of claim 1, wherein the antibody, at least one corticosteroid and at least one non-corticosteroid chemotherapeutic agent are administered sequentially.

40. The method of claim 1, wherein the antibody, at least one corticosteroid and at least one non-corticosteroid chemotherapeutic agent are all administered separately.

41. The method of claim 1, wherein the antibody, at least one corticosteroid and at least one non-corticosteroid chemotherapeutic agent are co-administered in one or two pharmaceutical compositions.

42. The method of claim 39, wherein the antibody is administered at least 1 day, before administration of said at least one corticosteroid and said at least one non-corticosteroid chemotherapeutic agent.

43. The method of claim 1, wherein the antibody is administered in a dose of 1 mg/kg or more.

44. The method of claim 1, wherein the antibody is administered once weekly for 2 to 12 weeks.

45. The method of claim 1 comprising administering a combination of corticosteroids.

46. The method of claim 1 comprising administering a combination of non-corticosteroid chemotherapeutic agents.

47. The method of claim 1, wherein said at least one corticosteroid comprises dexamethasone and said at least one non-corticosteroid chemotherapeutic agent comprises lenalidomide and bortezomib.

48. The method of claim 1, wherein said at least one corticosteroid comprises prednisone and said at least one non-corticosteroid chemotherapeutic agent comprises melphalan and bortezomib.

49. The method of claim 1, wherein the at least one corticosteroid comprises dexamethasone and said at least one non-corticosteroid chemotherapeutic agent comprises bortezomib.

50. The method of claim 6, wherein said glutamic acid derivative is thalidomide or a thalidomide analog.

51. The method of claim 7, wherein said proteasome inhibitor is bortezomib.

52. The method of claim 8, wherein said vinca alkaloid is vincristine.

53. The method of claim 9 wherein said anthracycline is doxorubicin.

54. The method of claim 1, wherein said at least one corticosteroid comprises dexamethasone and said at least one non-corticosteroid chemotherapeutic agent comprises thalidomide and lenalidomide.

55. The method of claim 1, wherein said at least one corticosteroid comprises dexamethasone and said at least one non-corticosteroid chemotherapeutic agent comprises vincristine and doxorubicin.

56. A method for inhibiting growth and/or proliferation of tumor cells expressing CD38 in an individual in need thereof, comprising administering to the individual i) an antibody that specifically binds CD38, wherein the antibody comprises heavy and light chain variable region CDRs set forth in SEQ ID NOs: 13, 14, and 15 and SEQ ID NOs: 18, 19, and 20, respectively, ii) at least one corticosteroid, and iii) at least one non-corticosteroid chemotherapeutic agent.

57. The method of claim 56, wherein said antibody comprises heavy and light chain variable regions having the amino acid sequences set forth in SEQ ID No:12 and 17, respectively.

58. The method of claim 56, wherein said at least one non-corticosteroid chemotherapeutic agent comprises an alkylating agent.

59. The method of claim 56, wherein said at least one non-corticosteroid chemotherapeutic agent comprises one or more agents selected from the group consisting of: melphalan, mechlorethamine, thioepa, chlorambucil, carmustine (BSNU), lomustine (CCNU), cyclophosphamide, busulfan, dibromomannitol, streptozotocin, dacarbazine (DTIC), procarbazine, mitomycin C, cisplatin and other platinum derivatives.

60. The method of claim 56, wherein said at least one non-corticosteroid chemotherapeutic agent comprises a glutamic acid derivative.

61. The method of claim 56, wherein said at least one non-corticosteroid chemotherapeutic agent comprises a proteasome inhibitor.

62. The method of claim 56, wherein said at least one non-corticosteroid chemotherapeutic agent comprises a vinca alkaloid.

63. The method of claim 56 wherein said at least one non-corticosteroid chemotherapeutic agent comprises an anthracycline.

64. The method of claim 56, wherein said at least one corticosteroid comprises a glucocorticoid.

65. The method of claim 56, wherein said at least one corticosteroid comprises prednisone.

66. The method of claim 56, wherein said at least one corticosteroid comprises dexamethasone and said at least one non-corticosteroid chemotherapeutic agent comprises lenalidomide and bortezomib.

67. The method of claim 56, wherein said at least one corticosteroid comprises prednisone and said at least one non-corticosteroid chemotherapeutic agent comprises melphalan and bortezomib.

68. The method of claim 56, wherein the at least one corticosteroid comprises dexamethasone and said at least one non-corticosteroid chemotherapeutic agent comprises bortezomib.

* * * * *

SEQUENCE LISTING

```
<160> NUMBER OF SEQ ID NOS: 71

<210> SEQ ID NO 1
<211> LENGTH: 321
<212> TYPE: DNA
<213> ORGANISM: Homo sapiens

<400> SEQUENCE: 1
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcttccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt accctcggac gttcggccaa     300
gggaccaagg tggaaatcaa a                                                321

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 3
<211> LENGTH: 11
<212> TYPE: PRT
<213> ORGANISM: Homo sapiens

<400> SEQUENCE: 3

Arg Ala Ser Gln Gly Ile Ser Ser Trp Leu Ala
1               5                   10

<210> SEQ ID NO 4
<211> LENGTH: 7
<212> TYPE: PRT
```

<213> ORGANISM: Homo sapiens

<400> SEQUENCE: 4

Ala Ala Ser Ser Leu Gln Ser
1               5

<210> SEQ ID NO 5
<211> LENGTH: 9
<212> TYPE: PRT
<213> ORGANISM: Homo sapiens

<400> SEQUENCE: 5

Gln Gln Tyr Asn Ser Tyr Pro Arg Thr
1               5

<210> SEQ ID NO 6
<211> LENGTH: 366
<212> TYPE: DNA
<213> ORGANISM: Homo sapiens

<400> SEQUENCE: 6

```
caggtccagc tggtgcagtc tggggctgag gtgaagaagc ctgggtcctc ggtgaaggtc    60
tcctgcaagg cttctggagg caccttcagc agctatgctt tcagctgggt gcgacaggcc   120
cctggacaag gacttgagtg gatgggaagg gtcatccctt ccttggtat agcaaactcc   180
gcacagaaat tccagggcag agtcacaatt accgcggaca atccacgag cacagcctac   240
atggacctga gcagcctgag atctgaggac acggccgtat attactgtgc gagagatgat   300
atagcagcac ttggtccttt tgactactgg ggccagggaa ccctggtcac cgtctcctca   360
gcctcc                                                              366
```

<210> SEQ ID NO 7
<211> LENGTH: 122
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
        115                 120

<210> SEQ ID NO 8
<211> LENGTH: 5
<212> TYPE: PRT
<213> ORGANISM: Homo sapiens

<400> SEQUENCE: 8

```
Ser Tyr Ala Phe Ser
 1               5

<210> SEQ ID NO 9
<211> LENGTH: 17
<212> TYPE: PRT
<213> ORGANISM: Homo sapiens

<400> SEQUENCE: 9

Arg Val Ile Pro Phe Leu Gly Ile Ala Asn Ser Ala Gln Lys Phe Gln
 1               5                  10                  15

Gly

<210> SEQ ID NO 10
<211> LENGTH: 11
<212> TYPE: PRT
<213> ORGANISM: Homo sapiens

<400> SEQUENCE: 10

Asp Asp Ile Ala Ala Leu Gly Pro Phe Asp Tyr
 1               5                  10

<210> SEQ ID NO 11
<211> LENGTH: 321
<212> TYPE: DNA
<213> ORGANISM: Homo sapiens

<400> SEQUENCE: 11
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgac gttcggccaa     300
gggaccaagg tggaaatcaa a                                                321

<210> SEQ ID NO 12
<211> LENGTH: 107
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 13
```

<210> SEQ ID NO 13
<211> LENGTH: 11
<212> TYPE: PRT
<213> ORGANISM: Homo sapiens

<400> SEQUENCE: 13

Arg Ala Ser Gln Ser Val Ser Ser Tyr Leu Ala
1               5                   10

<210> SEQ ID NO 14
<211> LENGTH: 7
<212> TYPE: PRT
<213> ORGANISM: Homo sapiens

<400> SEQUENCE: 14

Asp Ala Ser Asn Arg Ala Thr
1               5

<210> SEQ ID NO 15
<211> LENGTH: 10
<212> TYPE: PRT
<213> ORGANISM: Homo sapiens

<400> SEQUENCE: 15

Gln Gln Arg Ser Asn Trp Pro Pro Thr Phe
1               5                   10

<210> SEQ ID NO 16
<211> LENGTH: 372
<212> TYPE: DNA
<213> ORGANISM: Homo sapiens

<400> SEQUENCE: 16

```
gaggtgcagc tgttggagtc tgggggaggc ttggtacagc ctgggggtc cctgagactc      60
tcatgtgcag tctctggatt cacctttaac agctttgcca tgagctgggt ccgccaggct     120
ccagggaagg ggctggagtg ggtctcagct attagtggta gtggtggtgg cacatactac     180
gcagactccg tgaagggccg gttcaccatc tccagagaca attccaagaa cacgctgtat     240
ctgcaaatga acagcctgag agccgaggac acggccgtat atttctgtgc gaaagataag     300
attctctggt tcggggagcc cgtctttgac tactggggcc agggaaccct ggtcaccgtc     360
tcctcagcct cc                                                         372
```

<210> SEQ ID NO 17
<211> LENGTH: 124
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

```
Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser
        115                 120
```

<210> SEQ ID NO 18
<211> LENGTH: 5
<212> TYPE: PRT
<213> ORGANISM: Homo sapiens

<400> SEQUENCE: 18

```
Ser Phe Ala Met Ser
1               5
```

<210> SEQ ID NO 19
<211> LENGTH: 17
<212> TYPE: PRT
<213> ORGANISM: Homo sapiens

<400> SEQUENCE: 19

```
Ala Ile Ser Gly Ser Gly Gly Gly Thr Tyr Tyr Ala Asp Ser Val Lys
1               5                   10                  15

Gly
```

<210> SEQ ID NO 20
<211> LENGTH: 13
<212> TYPE: PRT
<213> ORGANISM: Homo sapiens

<400> SEQUENCE: 20

```
Asp Lys Ile Leu Trp Phe Gly Glu Pro Val Phe Asp Tyr
1               5                   10
```

<210> SEQ ID NO 21
<211> LENGTH: 321
<212> TYPE: DNA
<213> ORGANISM: Homo sapiens

<400> SEQUENCE: 21

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccgggctcct catctatgat gcttccaaca gggcctctgg catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa a                                             321
```

<210> SEQ ID NO 22
<211> LENGTH: 107
<212> TYPE: PRT
<213> ORGANISM: Homo sapiens

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Gly Leu Leu Ile
        35                  40                  45

Tyr Asp Ala Ser Asn Arg Ala Ser Gly Ile Pro Ala Arg Phe Ser Gly
```

```
              50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

<210> SEQ ID NO 23
<211> LENGTH: 11
<212> TYPE: PRT
<213> ORGANISM: Homo sapiens

<400> SEQUENCE: 23

```
Arg Ala Ser Gln Ser Val Ser Ser Tyr Leu Ala
 1               5                  10
```

<210> SEQ ID NO 24
<211> LENGTH: 7
<212> TYPE: PRT
<213> ORGANISM: Homo sapiens

<400> SEQUENCE: 24

```
Asp Ala Ser Asn Arg Ala Ser
 1               5
```

<210> SEQ ID NO 25
<211> LENGTH: 9
<212> TYPE: PRT
<213> ORGANISM: Homo sapiens

<400> SEQUENCE: 25

```
Gln Gln Arg Ser Asn Trp Pro Leu Thr
 1               5
```

<210> SEQ ID NO 26
<211> LENGTH: 366
<212> TYPE: DNA
<213> ORGANISM: Homo sapiens

<400> SEQUENCE: 26

```
gaggtgcagc tggtgcagtc tggagcagag gtgaaaaagc ccggggagtc tctgaagatc     60
tcctgtaagg gttctggata cagcttttcc aactactgga tcggctgggt gcgccagatg    120
cccgggaaag gcctggagtg gatggggatc atctatcctc atgactctga tgccagatac    180
agcccgtcct tccaaggcca ggtcaccttc tcagccgaca gtccatcagc accgcctac    240
ctgcagtgga gcagcctgaa ggcctcggac accgccatgt attactgtgc gagacatgta    300
gggtggggat cgcggtactg gtacttcgat ctctggggcc gtggcaccct ggtcactgtc    360
tcctca                                                               366
```

<210> SEQ ID NO 27
<211> LENGTH: 122
<212> TYPE: PRT
<213> ORGANISM: Homo sapiens

<400> SEQUENCE: 27

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Tyr
             20                  25                  30
```

```
Trp Ile Gly Trp Val Arg Gln Met Pro Gly Lys Gly Leu Glu Trp Met
            35                  40                  45

Gly Ile Ile Tyr Pro His Asp Ser Asp Ala Arg Tyr Ser Pro Ser Phe
        50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
                100                 105                 110

Gly Arg Gly Thr Leu Val Thr Val Ser Ser
            115                 120
```

<210> SEQ ID NO 28
<211> LENGTH: 5
<212> TYPE: PRT
<213> ORGANISM: Homo sapiens

<400> SEQUENCE: 28

```
Asn Tyr Trp Ile Gly
1               5
```

<210> SEQ ID NO 29
<211> LENGTH: 17
<212> TYPE: PRT
<213> ORGANISM: Homo sapiens

<400> SEQUENCE: 29

```
Ile Ile Tyr Pro His Asp Ser Asp Ala Arg Tyr Ser Pro Ser Phe Gln
1               5                   10                  15

Gly
```

<210> SEQ ID NO 30
<211> LENGTH: 13
<212> TYPE: PRT
<213> ORGANISM: Homo sapiens

<400> SEQUENCE: 30

```
His Val Gly Trp Gly Ser Arg Tyr Trp Tyr Phe Asp Leu
1               5                   10
```

<210> SEQ ID NO 31
<211> LENGTH: 300
<212> TYPE: PRT
<213> ORGANISM: Homo sapiens

<400> SEQUENCE: 31

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
                20                  25                  30

Leu Ile Leu Val Val Val Leu Ala Val Val Val Pro Arg Trp Arg Gln
            35                  40                  45

Gln Trp Ser Gly Pro Gly Thr Thr Lys Arg Phe Pro Glu Thr Val Leu
        50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95
```

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
        130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 32
<211> LENGTH: 300
<212> TYPE: PRT
<213> ORGANISM: Homo sapiens

<400> SEQUENCE: 32

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
        130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp

```
                    165                 170                 175
Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Ala Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 33
<211> LENGTH: 300
<212> TYPE: PRT
<213> ORGANISM: Homo sapiens

<400> SEQUENCE: 33

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Ala Leu Glu Ala
225                 230                 235                 240
```

Trp Val Ile His Gly Gly Arg Glu Asp Ser Arg Asp Leu Cys Gln Asp
            245                 250                 255

Pro Thr Ile Lys Glu Leu Glu Ser Ile Ile Ser Lys Arg Asn Ile Arg
        260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
        290                 295                 300

<210> SEQ ID NO 34
<211> LENGTH: 300
<212> TYPE: PRT
<213> ORGANISM: Homo sapiens

<400> SEQUENCE: 34

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Phe Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 35

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgaaagcttc taatacgact cactataggg c                              31

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaagatgaag acagatggtg cagccaccgt acg                            33

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggagggtgcc aggggaaga ccgatgggcc ctt                             33

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggagtagag tcctgaggac tg                                        22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggataacaat ttcacacagg                                           20

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgaaagcttc taatacgact cactataggg caagcagtgg tatcaacgca gagt     54

<210> SEQ ID NO 41
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggtcagggcg cctgagttcc acg                                             23

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gataagcttg ccgccaccat ggactggacc tggaggttcc tc                        42

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gataagcttg ccgccaccat ggagtttggg ctgagctggc tt                        42

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gataagcttg ccgccaccat ggaagcccca gctcagcttc tc                        42

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gataagcttg ccgccaccat gagggtcctc gctcagctcc tg                        42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gataagcttg ccgccaccat ggggtcaacc gccatcctcg cc                        42

<210> SEQ ID NO 47
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 47
gataagcttg ccgccaccat ggaagcccca gctcagcttc tc                         42

<210> SEQ ID NO 48
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctgctgtggc ccatggtgtg ggcctaccct tacgacgtgc ctgactacgc caggtggcgc      60
cagacgtgga gc                                                         72

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aggtcaggta cctcagatct cagatgtgca ag                                   32

<210> SEQ ID NO 50
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tatagcccgg ggccgccacc atgtggtggc gcctgtggtg gctgctgctg ctgctgctgc      60
tgctgtggcc catggtgtgg gcc                                             83

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaagacttaa ggcagcggca gaa                                             23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtagtctgag cagtactcgt tgc                                             23
```

```
<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgcattcatt ttatgtttca ggt                                             23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcggacatct catgactttc ttt                                             23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aggacacgct gctaggctac ctt                                             23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtcctttctc cagtctgggc aag                                             23

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tccaccatgt atcacccagg cctctagagc ctgaaccttc tctggttg                  48

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caaccagaga aggttcaggc tctagaggcc tgggtgatac atggtgga                  48

<210> SEQ ID NO 59
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gatattcttg caggaaaatc gaatattcct tttgcttat                           39

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ataagcaaaa ggaatattcg atttccctgc aagaatatc                           39

<210> SEQ ID NO 61
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tctgtagata ttcttgcaga aaaattgaat gttccttttg cttata                   46

<210> SEQ ID NO 62
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tataagcaaa aggaacattc aattttttctg caagaatatc tacaga                  46

<210> SEQ ID NO 63
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Asn Ile Tyr Arg Pro Asp Lys Phe Leu Gln Cys Val Lys Asn Pro
1               5                   10                  15

Glu Asp Ser Ser Cys Thr Ser Glu Ile
            20                  25

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Val His Asn Leu Gln Pro Glu Lys Val Gln Thr Leu Glu Ala Trp
```

```
1               5                   10                  15

Val Ile His Gly Gly
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Leu Glu Ser Ile Ile Ser Lys Arg Asn Ile Gln Phe Ser Ala Lys
1               5                   10                  15

Asn Ile Tyr Arg Cys
            20

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Lys Arg Asn Ile Gln Phe Ser Cys Lys Asn Ile Tyr Arg
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Lys Val Gln Thr Leu Glu Ala Trp Val Ile His Gly Gly
1               5                   10

<210> SEQ ID NO 68
<211> LENGTH: 5
<212> TYPE: PRT
<213> ORGANISM: Homo sapiens

<400> SEQUENCE: 68

Arg Asn Ile Gln Phe
1               5

<210> SEQ ID NO 69
<211> LENGTH: 4
<212> TYPE: PRT
<213> ORGANISM: Homo sapiens

<400> SEQUENCE: 69

Trp Val Ile His
1

<210> SEQ ID NO 70
<211> LENGTH: 3
<212> TYPE: PRT
<213> ORGANISM: Homo sapiens

<400> SEQUENCE: 70
```

```
Lys Arg Asn
1

<210> SEQ ID NO 71
<211> LENGTH: 4
<212> TYPE: PRT
<213> ORGANISM: Homo sapiens

<400> SEQUENCE: 71

Val Gln Thr Leu
1
```